US012245846B2

(12) United States Patent
Wakita

(10) Patent No.: US 12,245,846 B2
(45) Date of Patent: Mar. 11, 2025

(54) SCATTERED LIGHT SIGNAL MEASURING APPARATUS AND INFORMATION PROCESSING APPARATUS

(71) Applicant: SONY CORPORATION, Tokyo (JP)

(72) Inventor: Yoshihiro Wakita, Tokyo (JP)

(73) Assignee: SONY CORPORATION, Tokyo (JP)

( * ) Notice: Subject to any disclaimer, the term of this patent is extended or adjusted under 35 U.S.C. 154(b) by 904 days.

(21) Appl. No.: 17/048,433

(22) PCT Filed: Apr. 5, 2019

(86) PCT No.: PCT/JP2019/015112
§ 371 (c)(1),
(2) Date: Oct. 16, 2020

(87) PCT Pub. No.: WO2019/208165
PCT Pub. Date: Oct. 31, 2019

(65) Prior Publication Data
US 2021/0161408 A1 Jun. 3, 2021

(30) Foreign Application Priority Data

Apr. 24, 2018 (JP) .................................. 2018-083222
Oct. 22, 2018 (JP) .................................. 2018-198647

(51) Int. Cl.
*G01N 21/47* (2006.01)
*A61B 5/026* (2006.01)
(Continued)

(52) U.S. Cl.
CPC ............ *A61B 5/0261* (2013.01); *G01N 21/47* (2013.01); *G01P 3/366* (2013.01); *G01P 5/26* (2013.01)

(58) Field of Classification Search
CPC ......... A61B 5/0261; G01N 2/47; G01P 3/366; G01P 5/26
See application file for complete search history.

(56) References Cited

U.S. PATENT DOCUMENTS 6,037,579 A * 3/2000 Chan .................. G01N 21/4795
250/576
2008/0097172 A1 4/2008 Sawada et al.
(Continued)

FOREIGN PATENT DOCUMENTS

CN 1591020 A 3/2005
CN 1950027 A 4/2007
(Continued)

OTHER PUBLICATIONS

Jacques Duparré et al., Novel Optics/Micro-Optics for Miniature Imaging Systems, Proceedings of SPIE vol. 6196, Photonics in Multimedia, Apr. 21, 2006, pp. 1-15, SPIE.

*Primary Examiner* — Daniel L Cerioni
(74) *Attorney, Agent, or Firm* — Paratus Law Group, PLLC

(57) ABSTRACT

There is provided a scattered light signal measurement apparatus and an information processing apparatus that are capable of performing accurate measurement while preventing noise due to changes in relative velocity and relative position caused between a sensor and an observation target. The scattered light signal measurement apparatus includes a light receiving element and an incident angle limiting unit. The light receiving element receives scattered light obtained when coherent light emitted to a measurement target is scattered by the measurement target. The incident angle limiting unit limits an incident angle of the scattered light that is incident on a single point of the light receiving element to be equal to or smaller than a predetermined angle and controls the single light receiving element to increase an aperture ratio.

17 Claims, 73 Drawing Sheets

(51) Int. Cl.
*G01P 3/36* (2006.01)
*G01P 5/26* (2006.01)

(56) References Cited

U.S. PATENT DOCUMENTS

| | | |
|---|---|---|
| 2009/0202251 A1 | 8/2009 | Shibayama |
| 2011/0087108 A1 | 4/2011 | Onoe et al. |
| 2013/0137994 A1* | 5/2013 | Sawada ................ A61B 5/0261 |
| | | 600/479 |
| 2013/0222786 A1 | 8/2013 | Hanson et al. |
| 2017/0007138 A1 | 1/2017 | Kim |
| 2017/0188851 A1 | 7/2017 | Leboeuf |
| 2017/0251926 A1 | 9/2017 | Yoon et al. |
| 2018/0203242 A1* | 7/2018 | Takeuchi ............. G02B 3/0056 |

FOREIGN PATENT DOCUMENTS

| | | | |
|---|---|---|---|
| CN | 104729602 A | | 6/2015 |
| EP | 0472959 A | | 3/1992 |
| EP | 0284248 B1 | | 12/1993 |
| JP | H05-273225 A | | 10/1993 |
| JP | H11-337475 A | | 12/1999 |
| JP | 2005-72662 A | * | 3/2005 |
| JP | 2008128744 A | * | 6/2008 |
| JP | 2008-181220 A | | 8/2008 |
| JP | 2017-192629 A | | 10/2017 |
| WO | WO 2006/051726 A1 | | 5/2006 |
| WO | WO-2017027551 A1 | | 2/2017 |
| WO | WO-2017033553 A1 | * | 3/2017 ................ F21V 5/04 |

* cited by examiner (a)

(b)

(c)

(a)

(b)

(a)

(b)

SCATTERED LIGHT SIGNAL MEASURING APPARATUS AND INFORMATION PROCESSING APPARATUS

CROSS REFERENCE TO PRIOR APPLICATION

This application is a National Stage Patent Application of PCT International Patent Application No. PCT/JP2019/015112 (filed on Apr. 5, 2019) under 35 U.S.C. § 371, which claims priority to Japanese Patent Application Nos. 2018-083222 (filed on Apr. 24, 2018) and 2018-198647 (filed on Oct. 22, 2018), which are all hereby incorporated by reference in their entirety.

TECHNICAL FIELD

The present technology relates to a scattered light signal measurement apparatus and an information processing apparatus that are capable of measuring information related to the velocity of a group of particles such as red blood cells in blood.

BACKGROUND ART

Various systems have been developed for a blood flow velocity sensor that measures the velocity of a blood flow flowing through a blood vessel. For example, Patent Literature 1 has disclosed a laser Doppler blood flow meter.

The laser Doppler blood flow meter emits laser light to a living body. The laser light is scattered by biological tissues. Scattering by particles such as red blood cells that move in a blood flow causes a shift (Doppler shift) of a wavelength due to the Doppler effect as compared to scattering by other tissues that do not move.

Therefore, it is possible to measure a motion velocity of particles in blood such as red blood cells, i.e., a blood flow velocity by detecting scattered light to obtain a signal change related to such a Doppler shift. Further, it is also possible to measure a velocity of a group of particles that move in a measurement target object other than the particles in blood by using this measurement principle.

CITATION LIST

Patent Literature

Patent Literature 1: Japanese Patent Application Laid-open No. 2017-192629

DISCLOSURE OF INVENTION

Technical Problem

However, in the laser Doppler blood flow meter as described in Patent Literature 1, a body motion (motion of a living body to which a sensor is attached) may cause a position shift or a relative velocity between the living body and the sensor. Since the Doppler shift caused by the motion of the particles in blood as described above is used for measurement in the laser Doppler blood flow meter, if a position shift or a relative velocity is caused between the living body and the sensor, this Doppler shift is affected and noise is generated in the measurement result.

In view of the above-mentioned circumstances, it is an object of the present technology to provide a scattered light signal measurement apparatus and an information processing apparatus that are capable of performing accurate measurement while preventing noise due to changes in relative velocity and relative position caused between a sensor and an observation target.

Solution to Problem

In order to accomplish the above-mentioned object, a scattered light signal measurement apparatus according to the present technology includes a light receiving element and an incident angle limiting unit.

The light receiving element receives scattered light obtained when coherent light emitted to a measurement target is scattered by the measurement target.

The incident angle limiting unit limits an incident angle of the scattered light that is incident on a single point of the light receiving element to be equal to or smaller than a predetermined angle and controls the single light receiving element to increase an aperture ratio.

In accordance with this configuration, the incident angle of scattered light of the scattered light scattered by the measurement target, which is incident on the single point of the light receiving element, is limited to be equal to or smaller than the predetermined angle. If a relative velocity caused by the body motion between the light receiving element and the measurement target is caused, noise can be generated due to the Doppler beat caused between scattered light beams having different incident angles on the light receiving element. However, since the incident angle of the scattered light that is incident on the single point of the light receiving element is limited to be equal to or smaller than the predetermined angle in the above-mentioned configuration, and thus the frequency of the Doppler beat between the scattered light beams having the incident angles different from each other is reduced. Accordingly, it is possible to detect only the Doppler beat caused by the motion of particles at the measurement target and to correctly calculate the motion of the particles at the measurement target.

The incident angle limiting unit may limit a light beam diameter of the scattered light that is incident on the single point of the light receiving element to be smaller than an entire light beam diameter that is incident on the light receiving element.

The incident angle limiting unit may concentrate the scattered light at a different point of the light receiving element in accordance with an incident angle.

The incident angle limiting unit may be a lens array in which a plurality of lenses is arranged.

The light receiving element may be at least one, and the plurality of lenses may concentrate scattered light at an incident angle limited by each of a plurality of lenses to the single light receiving element.

It may further include a light shield that shields light incident on a portion between the plurality of lenses.

The incident angle limiting unit is a lens, and the scattered light signal measurement apparatus may further include a light shield that prevents mixing of light incident on the lens and light incident on a portion other than the lens.

The light receiving element may be at least one, and the incident angle limiting unit that sets a plurality of pin holes with respect to the single light receiving element, limits the incident angle of the scattered light that is incident on the single point of the light receiving element to be equal to or smaller than the predetermined angle, and concentrates scattered light having an amount larger than an amount of scattered light, which is concentrated by a single pin hole, to the light receiving element.

The scattered light signal measurement apparatus may further include: a coherent light source that emits the coherent light; and an irradiation light control unit that controls an irradiation diameter of the coherent light emitted from the coherent light source.

The irradiation light control unit may make the coherent light collimated, the coherent light being emitted from the light source.

The irradiation diameter may be 0.5 mm or more and 2 mm or less.

The scattered light signal measurement apparatus may further include: a first coherent light source that emits first coherent light having a first wavelength range to the measurement target; and a second coherent light source that emits second coherent light having a second wavelength range different from the first wavelength range to the measurement target.

The scattered light signal measurement apparatus may further include a light receiving element array in which a plurality of light receiving elements is arranged.

The incident angle limiting unit may include one louver layer or a plurality of louver layers, the louver layer may include a plurality of louvers extending in parallel to each other, and in a case of including the plurality of louver layers, the incident angle limiting unit may be an optical path limiting filter in which directions in which the respective louvers of the layers extend cross each other.

The scattered light signal measurement apparatus may further include a polarization filter disposed in any optical path between the measurement target and the light receiving element.

The coherent light source and the irradiation light control unit may make the coherent light incident on the measurement target in a direction inclined with respect to an optical path of scattered light travelling toward the light receiving surface from the measurement target.

The irradiation light control unit may shape the coherent light into an elliptical shape and emits the shaped coherent light such that an irradiation spot of the coherent light at the measurement target has a circular shape.

In order to accomplish the above-mentioned object, an information processing apparatus according to the present technology includes: a light receiving element that receives scattered light obtained when coherent light emitted to a measurement target is scattered by the measurement target; an incident angle limiting unit that limits an incident angle of the scattered light that is incident on a single point of the light receiving element to be equal to or smaller than a predetermined angle and controls the single light receiving element to increase an aperture ratio; and a particle velocity information calculation unit.

The particle velocity information calculation unit calculates particle velocity information that is information regarding velocity of a particle inside the measurement target on the basis of a signal output from the light receiving element.

The information processing apparatus may further include a noise cancellation unit that detects a relative motion between the sensor and the measurement target on the basis of an output of a light receiving element array in which a plurality of light receiving elements provided in the sensor is arranged, and cancels noise caused by the relative motion between the sensor and the measurement target on the basis of the particle velocity information.

The measurement target may be blood, and the particle velocity information calculation unit may calculate blood flow velocity information that is information regarding velocity of a red blood cell inside the measurement target.

The information processing apparatus may include a wearable device.

Advantageous Effects of Invention

As described above, in accordance with the present technology, it is possible to provide a scattered light signal measurement apparatus and an information processing apparatus that are capable of performing accurate measurement while preventing noise due to changes in relative velocity and relative position caused between a sensor and an observation target.

MODE(S) FOR CARRYING OUT THE INVENTION

The scattered light signal measurement apparatus according to the present technology is an apparatus that detects a velocity of a group of particles and a beat signal caused by interference between coherent light beams by using the laser Doppler phenomenon and measures a flow rate per unit volume of the group of particles and a velocity distribution by using the laser Doppler phenomenon. The measurement target particles are typically particles in blood, such as red blood cells flowing through a blood vessel. In a case where the scattered light signal measurement apparatus according to the present technology is used for observation of motions of particles in blood, an amount of moving particles in blood in an observation region proportional to the blood flow rate per hour of a tissue and a velocity distribution of particles in blood in the observation region (only a velocity along an observation direction axis) can be measured. Hereinafter, a blood flow measurement apparatus according to an embodiment of the present technology will be described. It should be noted that in this specification, red blood cells are used as a generic term for particles in blood that scatter laser light, the particles in blood including red blood cells.

[Regarding Principle of Laser Doppler Blood Flow Measurement Apparatus]

Figure 1:
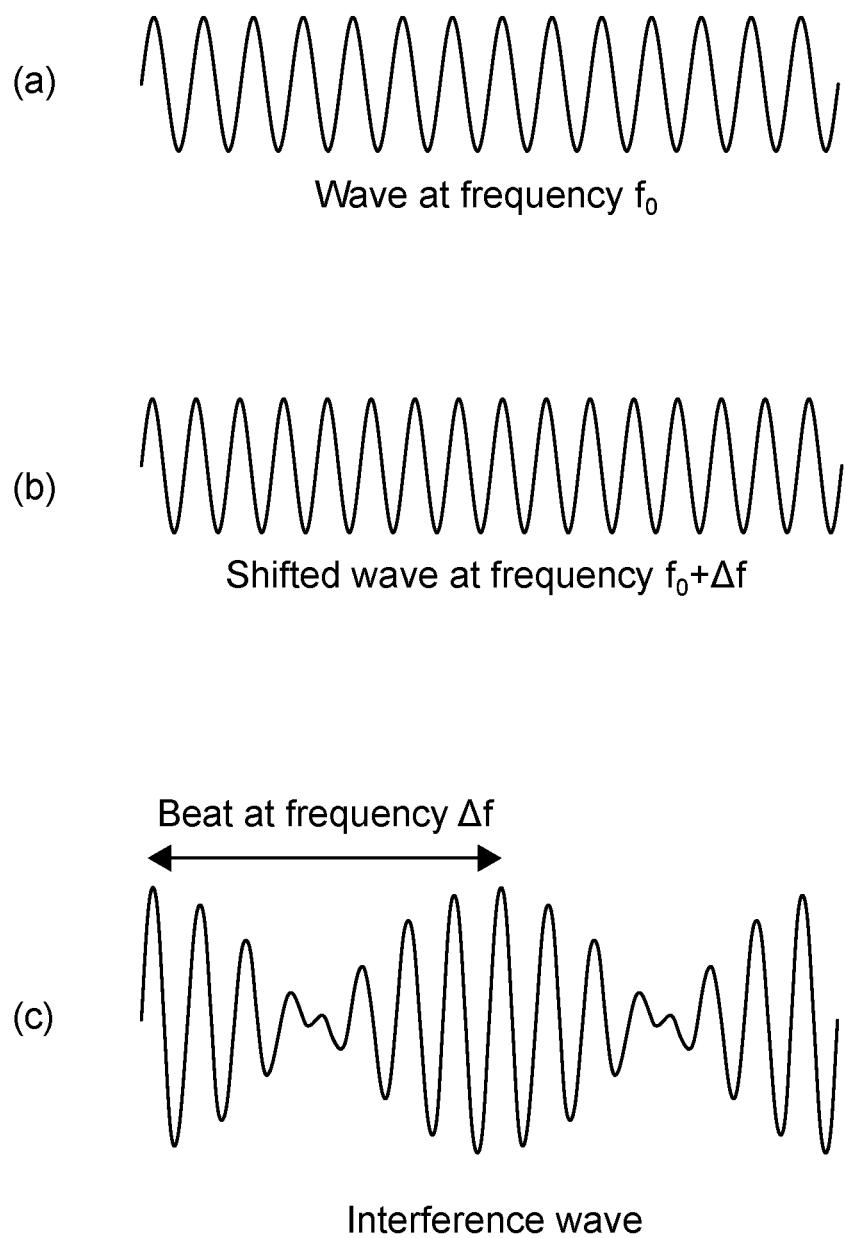
FIG. 1 A schematic diagram showing a Doppler shift and a beat phenomenon caused by the Doppler shift.

The laser Doppler blood flow measurement apparatus is a measurement apparatus using a Doppler shift of light. Hereinafter, the principle of the laser Doppler blood flow measurement apparatus will be described. It should be noted that regarding the Doppler shift phenomenon dealt with in the present invention, the relativistic effect is negligibly small because a relative velocity between target objects is sufficiently small with respect to a light velocity. Therefore, the relativistic effect is omitted from this principle description. Further, in reality, the refractive index differs from the refractive index of the sensor portion inside the human body. Therefore, a light velocity c, which determines an amount of Doppler shift, is different (or a wavelength A is different). However, the difference in refractive index has little effect on the principle of the present invention. Therefore, the effect of the refractive index is omitted from this principle description. FIG. 1 is a schematic diagram showing a Doppler shift and a Doppler beat that is a phenomenon that occurs due to interference between Doppler-shifted waves and original waves.

It is assumed that after a wave at a frequency $f_0$ reaches a measurement point as shown in FIG. 1(a), the frequency shifts due to the Doppler phenomenon and the frequency of the wave becomes $f_0 + \Delta f$ as shown in FIG. 1(b).

It is known that in this case, both the interfering waves have a beat at a frequency $\Delta f$ as shown in FIG. 1(c). This wave at the frequency $\Delta f$ is referred to as a Doppler beat. Using such a beat phenomenon, a velocity of a movable object, which causes a Doppler shift, relative to a measurement point can be obtained by measuring a frequency $\Delta f$ of a Doppler beat even without measuring a frequency $f_0 + \Delta f$ at which the Doppler shift is caused.

Figure 2:
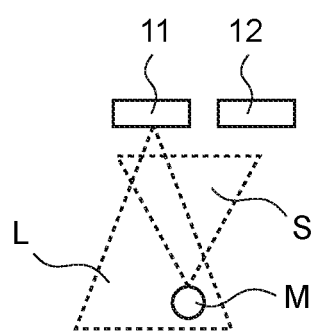
FIG. 2 A schematic diagram showing the principle of a laser Doppler blood flow measurement apparatus.

FIG. 2 is a schematic diagram showing the principle of the laser Doppler blood flow measurement apparatus. As shown in the figure, laser light L is emitted from a light emitting unit 11. When the laser light L is incident on a scatterer M, the laser light L is reflected by the scatterer M and scattered light S is generated. The scattered light S is incident on a light receiving unit 12 and is detected.

Figure 3:
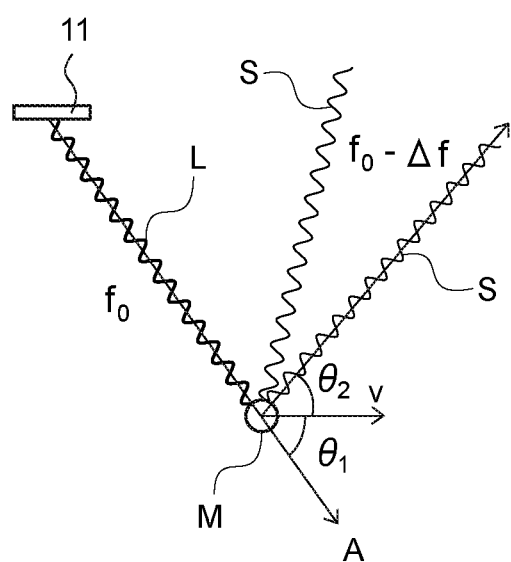
FIG. 3 A schematic diagram showing a Doppler shift due to a relative motion between a light emitting unit of the laser Doppler blood flow measurement apparatus and a scatterer.

FIG. 3 is a schematic diagram showing a Doppler shift due to a relative motion between the light emitting unit 11 and the scatterer M. As shown in the figure, the scatterer M is irradiated with laser light L at a frequency $f_0$ from the light emitting unit 11. The scatterer M moves at a velocity v in a direction to form an angle $\theta_1$ with respect to an optical axis A of the laser light L.

FIG. 3 is a diagram in which the scatterer M is moving relative to the light emitting unit 11 that is stationary. In this case, irradiation light received by the moving scatterer M causes a Doppler shift to the scatterer M. In addition, when the scattered light emitted by the moving scatterer M is observed at a stationary measurement point, a Doppler shift occurs. In this case, a Doppler shift $\Delta f_1$ viewed from the scatterer M is expressed by (Expression 1-1) below.

[Formula 1]

$$\alpha_0 = \frac{1}{\lambda_0} \quad \text{(Expression 1-1)}$$

$$\Delta f_1 = -\frac{v}{c} f_0 \cos\theta_1 = -\frac{v\cos\theta_1}{\lambda_0} = -\alpha_0 \, v\cos\theta_1$$

In addition, assuming that an angle formed by a direction to observe the scattered light emitted and the velocity v is $\theta_2$, a Doppler shift $\Delta f_2$ of the light observed by an observer with respect to the light emitted by the scatterer M is expressed by (Expression 1-2).

[Formula 2]

$$\Delta f_2 = \frac{v}{c}(f_0 + \Delta f_1)\cos\theta_2 \quad \text{(Expression 1-1)}$$
$$\simeq \frac{v\cos\theta_2}{\lambda_0}$$
$$= \alpha_0 \, v\cos\theta_2$$

In a case where the emission direction and the observation direction of light are exactly opposite like a velocity gun, $\theta_1 + \theta_2 = 180°$. Therefore, $\cos\theta_2 = -\cos\theta_1$ is established. A Doppler shift $\Delta f$ of the observed light is expressed by (Expression 1-3).

[Formula 3]

$$\Delta f = \Delta f_1 + \Delta f_2 \quad \text{(Expression 1-3)}$$
$$= -\alpha_0 \, v\cos\theta_1 + \alpha_0 \, v\cos\theta_2$$
$$= -2\alpha_0 \, v\cos\theta_1$$

In (Expression 1-1), (Expression 1-2), and (Expression 1-3), c is a light velocity, $\lambda_0$ is a wavelength of the laser light L, and $\alpha_0$ is a proportional constant depending on the wavelength ($\lambda_0$) of the laser light L. As shown in Expression 1-1, the Doppler shift $\Delta f$ is proportional to the relative velocity between the light emitting unit 11 and the scatterer M and varies in a manner that depends on the angle $\theta_1$.

Further, the Doppler shift $\Delta f$ viewed from stationary coordinates depends on the emission direction of the scattered light S and varies in a manner that depends on an angle $\theta_2$.

Figure 4:
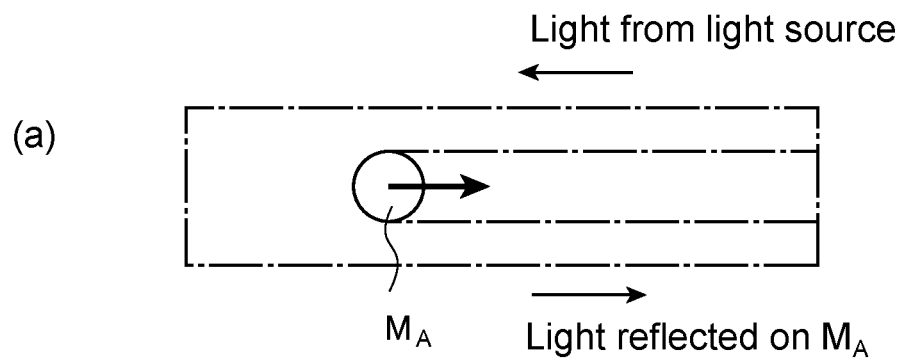
FIG. 4 A schematic diagram showing a Doppler shift due to a motion of the scatterer and a beat signal caused by it.
Figure 4:
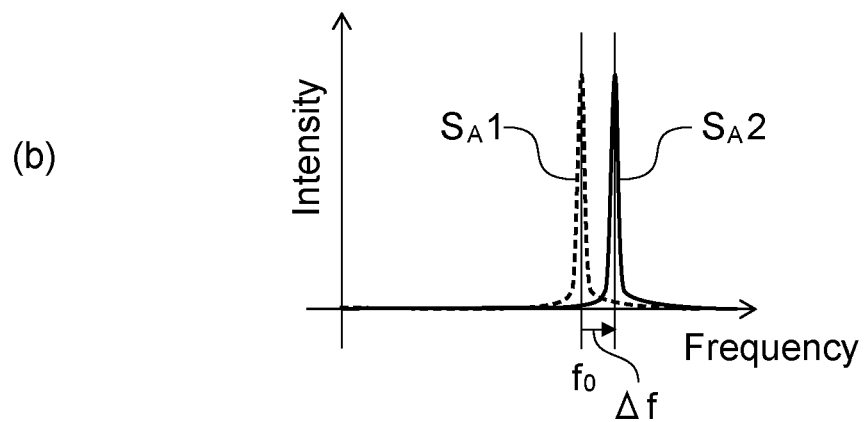
Figure 4:
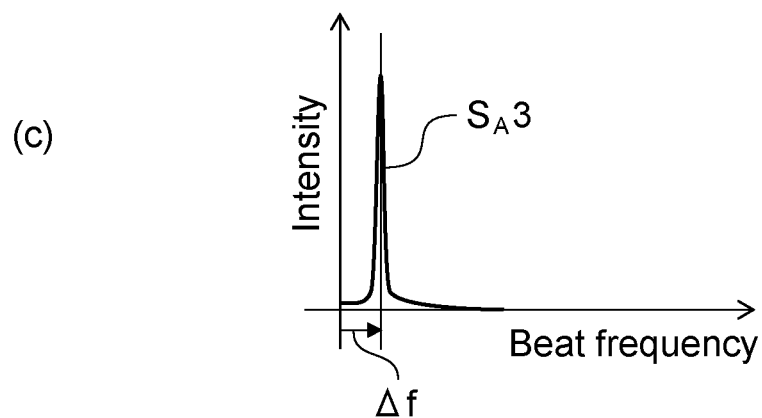
Figure 5:
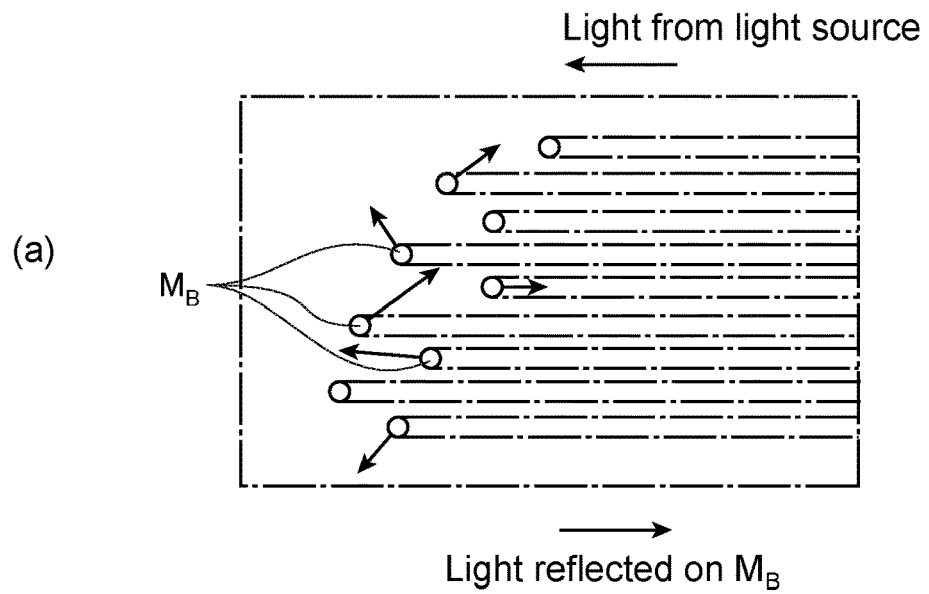
FIG. 5 A schematic diagram showing a Doppler shift due to a motion of the scatterer and a beat signal caused by it.
Figure 5:
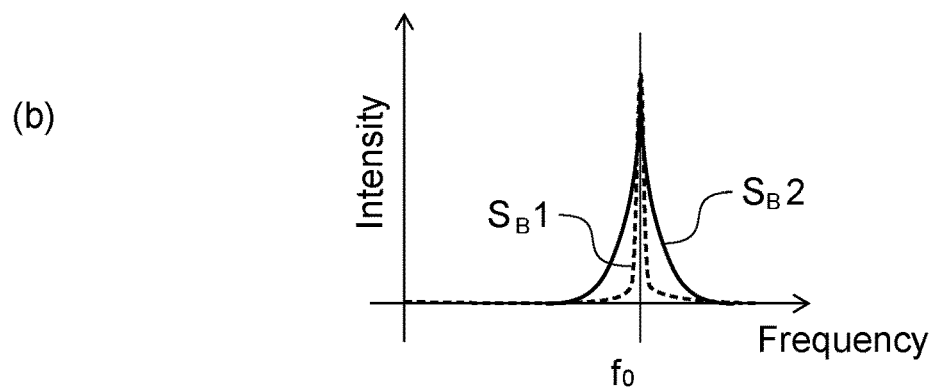
Figure 5:
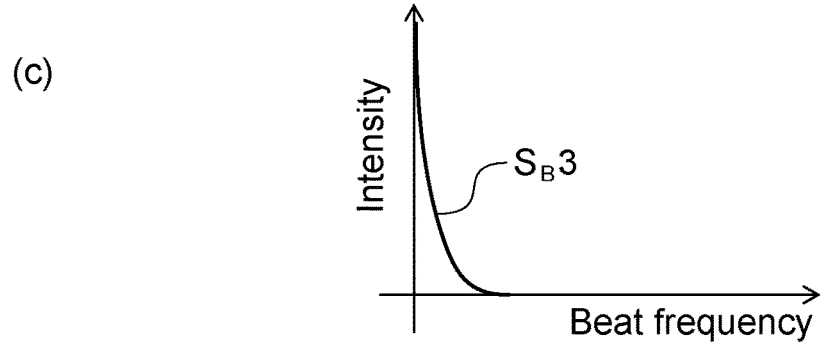

FIGS. 4 and 5 are schematic diagrams each showing a Doppler shift due to a motion of a scatterer. As shown in FIG. 4(a), it is assumed that a scatterer $M_A$ is moving in light emitted from a light source. In the figure, a velocity vector of the scatterer $M_A$ is shown as the arrow extended from the scatterer $M_A$.

FIG. 4(b) shows a power spectrum $S_A2$ of the light scattered by the moving scatterer $M_A$ and a power spectrum $S_A1$ of the light scattered by the stationary scatterer $M_A$.

As shown in the figure, the Doppler effect due to a motion of the scatterer $M_A$ results in a Doppler shift $\Delta f$, and the frequency of the scattered light $S_A2$ increases from the original frequency $f_0$. Further, when the scatterer $M_A$ moves away from the light source, a Doppler shift occurs such that the frequency of the scattered light $S_A2$ decreases.

FIG. 4(c) is a power spectrum $S_A3$ of a Doppler beat caused by interference between scattered light $S_A1$ and scattered light $S_A2$. A frequency of $S_A3$ is an absolute value of a difference between the frequency of $S_A1$ and the frequency of $S_A2$. A motion velocity of the scatterer $M_A$ can be determined on the basis of a peak frequency or mean frequency of this power spectrum $S_A3$. It should be noted that in order to simultaneously receive the scattered light $S_A1$ and the scattered light $S_A2$ for generating a Doppler beat, it is sufficient that a fixed scatterer is additionally prepared in order to direct the light from the light source to the light receiving unit.

Next, as shown in FIG. 5(a), it is assumed that many scatterers $M_B$ are moving in various directions in the light emitted from the light source. In the figure, velocity vectors of the scatterers $M_B$ are shown as the arrows extended from the scatterers $M_B$. The scatterers $M_B$ with no arrows indicate that they are stationary.

FIG. 5(b) shows a power spectrum $S_B1$ of light scattered by the scatterer $M_B$ that is stationary and a power spectrum $S_B2$ of light scattered by the moving scatterer $M_B$. For a blood flow measurement example, the stationary scatterer $M_B$ is a body tissue or the like. The moving scatterer $M_B$ is a red cell or the like.

In this case, a motion velocity of the respective scatterers $M_B$ relative to the light source is different. Therefore, as shown in FIG. 5(b), the power spectrum $S_B2$ of the scattered light is a composite wave of the Doppler shift due to the many scatterers $M_B$. In a case where the ratio of the amount of stationary scatterers is much higher than the ratio of the amount of moving scatterers, the scattered light of the stationary scatterers $M_B$ has much higher intensity than that of the scattered light of the moving scatterers $M_B$. In this case, most of the interference between the scattered light causing the Doppler beat is interference between the scattered light of the stationary scatterers $M_B$ and the scattered light of the moving scatterers $M_B$.

FIG. 5(c) is a power spectrum $S_B3$ of a Doppler beat caused by interference between scattered light $S_B1$ and scattered light $S_B2$. A frequency of $S_B3$ is an absolute value of a difference between the frequency of $S_B1$ and the frequency of $S_B2$. The shape of this power spectrum shows a velocity distribution of the scatterers $M_B$ relative to the light source. Therefore, an actual velocity distribution of the scatterers $M_B$ can be determined by considering a decrease in Doppler shift amount in a moving direction of each scatterer $M_B$.

It should be noted that a technique of measuring this Doppler shift due to the many observed objects moving in the respective directions is called dynamic light scattering (DLS).

In the description so far, the Doppler shift caused by the relative motion of the scatterer M relative to the light emitting unit 11 has been described. Next, a Doppler shift caused by a relative motion of the light receiving unit 12 relative to the scatterer M will be described.

Figure 6:
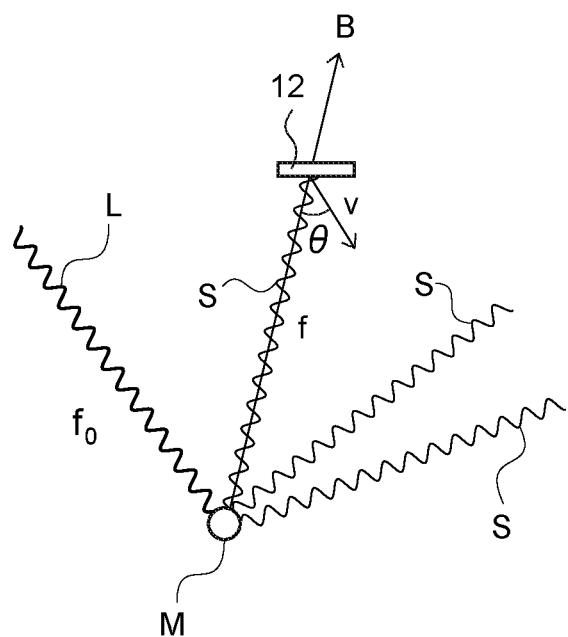
FIG. 6 A schematic diagram showing a Doppler shift due to a relative motion between the light receiving unit of the laser Doppler blood flow measurement apparatus and the scatterer.

FIG. 6 is a schematic diagram showing a Doppler shift due to the relative motion of the scatterer M relative to the light receiving unit 12. As shown in the figure, the scatterer M is irradiated with the laser light L at a frequency $f_0$ from the light emitting unit 11. The light receiving unit 12 is moving at the velocity v in a direction to form an angle $\theta$ with respect to an optical axis B of the scattered light S.

A Doppler shift $\Delta f$ caused in the scattered light S incident on the light receiving unit 12 in this case is expressed by (Expression 2) below.

[Formula 4]

$$\Delta f = \frac{v}{c} f \cos\theta \quad \text{(Expression 2)}$$
$$\simeq \frac{v}{c} f_0 \cos\theta \text{ (small quadratic term is ignored)}$$
$$= \frac{v \cos\theta}{\lambda_0}$$
$$= \alpha_0 v \cos\theta$$

In Expression 2, c is a light velocity, $\lambda_0$ is a wavelength of the laser light L, f is a frequency of scattered light emitted in a direction of the optical axis B, and $\alpha_0$ is a proportional constant depending on the wavelength ($\lambda_0$) of laser light L. The scattered light S is emitted in all directions. The scattered light S along a straight line connecting the scatterer M and the light receiving unit 12 reaches the light receiving unit 12.

The Doppler shift $\Delta f$ is proportional to the relative velocity between the scatterer M and the light receiving unit 12 and varies in a manner that depends on the angle $\theta$ with respect to the optical axis B.

Figure 7:
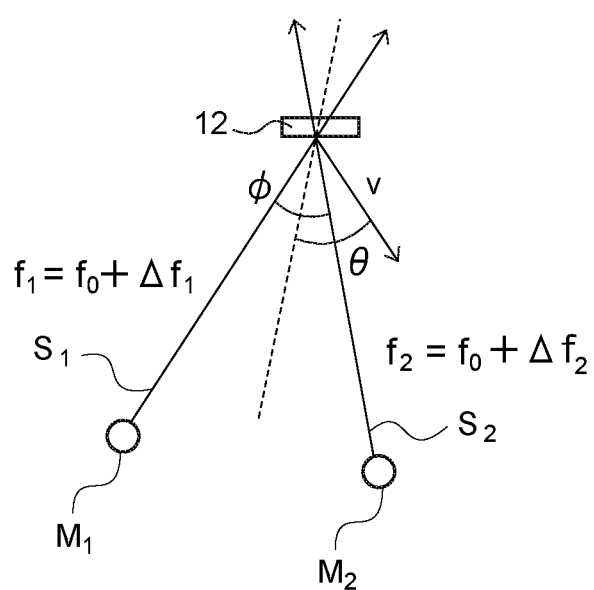
FIG. 7 A schematic diagram showing a Doppler shift due to a relative motion between the light receiving unit of the laser Doppler blood flow measurement apparatus and two scatterers.

Next, a Doppler shift due to relative motions of two scatterers relative to the light receiving unit 12 will be described. FIG. 7 is a schematic diagram showing a Doppler shift due to a relative pair motion the scatterer $M_1$ and the scatterer $M_2$ relative to the light receiving unit 12.

It is assumed that the laser light L having the frequency $f_0$ from the light emitting unit 11 is emitted to the scatterer $M_1$ and the scatterer $M_2$ and the light receiving unit 12 is moving at the velocity v in a direction to form the angle $\theta$ with respect to a center axis (dashed line) of an incident angle difference $\phi$ between scattered light $S_1$ and scattered light S2 on the light receiving unit 12. It is assumed that the frequency of light of the scattered light emitted from the scatterer $M_1$, which is emitted in the direction of the light receiving unit 12, is $f_1$ and the Doppler shift amount is $\Delta f_1$ and the frequency of light of the scattered light emitted from the scatterer $M_2$, which is emitted in the direction of the light receiving unit 12, is $f_2$ and the Doppler shift amount is $\Delta f_2$.

In this case, a frequency $F_1$ of the scattered light $S_1$ incident on the light receiving unit 12 from the scatterer $M_1$ is expressed by the following (Expression 3).

[Formula 5]

$$\left(\lambda_0 = \frac{c}{f_0}\right) \quad \text{(Expression 3)}$$
$$\left(\alpha_0 = \frac{1}{\lambda_0}\right)$$
$$F_1 = f_1\left\{1 + \frac{v}{c}\cos\left(\theta + \frac{1}{2}\phi\right)\right\}$$
$$= (f_0 + \Delta f_1)\left\{1 + \frac{v}{c}\cos\left(\theta + \frac{1}{2}\phi\right)\right\}$$
$$\simeq f_0 + \Delta f_1 + \frac{v}{c} f_0 \cos\left(\theta + \frac{1}{2}\phi\right) \text{ (quadratic term is ignored)}$$
$$= f_0 + \Delta f_1 + \alpha_0 v \cos\left(\theta + \frac{1}{2}\phi\right)$$

In (Expression 3), $\Delta f_1$ is a Doppler shift caused in the scattered light $S_1$ travelling toward to the light receiving unit 12 and a is a proportional constant depending on the wavelength of the light source. (Expression 3) ignores the small quadratic term "$\Delta f_1(v/c)\cos(\theta+(\frac{1}{2}))$" in the middle.

Further, a frequency $F_2$ of scattered light $S_2$ incident on the light receiving unit 12 from the scatterer $M_2$ is expressed by the following (Expression 4).

[Formula 6]

$$F_2 \simeq f_0 + \Delta f_2 + \alpha_0 v \cos\left(\theta - \frac{1}{2}\phi\right) \quad \text{(Expression 4)}$$

In (Expression 4), $\Delta f_2$ is a Doppler shift caused in the scattered light S2 travelling toward the light receiving unit 12 and $\alpha_0$ is a proportional constant depending on the wavelength $\lambda_0$ of the light source.

From the above, a Doppler shift $\Delta F$ of the scattered light $S_1$ and the scattered light $S_2$ is expressed by (Expression 5) below.

[Formula 7]

$$\beta = \sin\left(\frac{1}{2}\phi\right) \quad \text{(Expression 5)}$$
$$\Delta f_3 = -\beta \, 2\alpha_0 v \sin\theta$$
$$\Delta F = F_1 - F_2$$
$$\simeq \Delta f_1 - \Delta f_2 + \alpha_0 v \left\{\cos\left(\theta + \frac{1}{2}\phi\right) - \cos\left(\theta - \frac{1}{2}\phi\right)\right\}$$
$$= \Delta f_1 - \Delta f_2 + \alpha_0 v \left\{-2\sin\theta \sin\left(\frac{1}{2}\phi\right)\right\}$$
$$= \Delta f_1 - \Delta f_2 - 2\alpha_0 v \sin\theta \sin\left(\frac{1}{2}\phi\right)$$
$$= (\Delta f_1 - \Delta f_2) + \Delta f_3$$

In (Expression 5), $\Delta f_1-\Delta f_2$ is a frequency observed when the light receiving unit 12 is stationary and $\Delta f_3$ is a frequency that is added due to a motion of the light receiving unit 12. In the expression showing $\Delta f_3$, $\alpha_0 v$ is a fundamental frequency of the Doppler beat due to the relative motion velocity vector and $\beta$ is a relative-velocity beat-frequency decrease factor determined in a manner that depends on an incident angle difference $\varphi$ between the scattered light $S_1$ and the scattered light $S_2$ on the light receiving unit 12.

In a case where the incident angle difference $\varphi$ is sufficiently small, $\beta$ is close to 0 and $\Delta f_3$ is sufficiently small as compared to $(\Delta f_1-\Delta f_2)$. At this time, a distribution of the frequency difference $\Delta f_1-\Delta f_2$ caused by the blood flow velocity can be accurately measured. On the other hand, as the incident angle difference $\varphi$ is larger, $\beta$ is further from 0 and $\Delta f_3$ can include a frequency that cannot be distinguished from the frequency $(\Delta f_1-\Delta f_2)$. In particular, in interference between many stationary scatterers, $(©f_1-\Delta f_2)$ is 0. Therefore, when the light receiving unit is stationary, $\Delta f_3$ is 0 and thus no Doppler beat is caused. However, when the light receiving unit moves and $\varphi$ is large, $\Delta f_3$ can take a value similar to the blood flow velocity. Therefore, when the light receiving unit moves and $\varphi$ is large, the distribution of the frequency difference $\Delta f_1-\Delta f_2$ caused by the blood flow velocity cannot be accurately measured.

[Regarding Velocity Distribution of Red Blood Cells]

Figure 8:
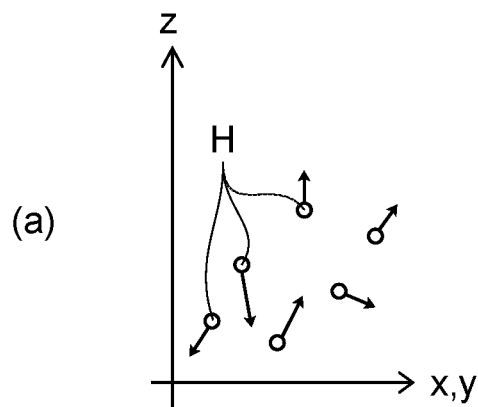
FIG. 8 A diagram showing a velocity distribution of red blood cells set by the laser Doppler blood flow measurement apparatus as a measurement target.
Figure 8:
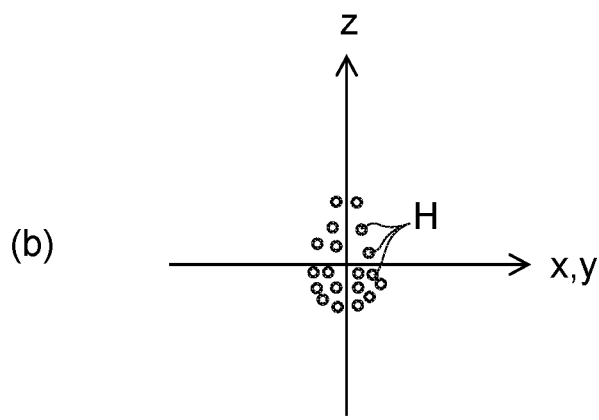
Figure 8:
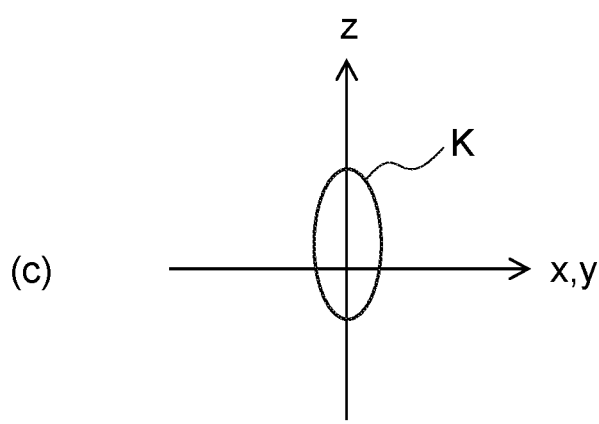

FIG. 8 is a diagram showing a velocity distribution of red blood cells. In FIG. 8(a), assuming that a direction perpendicular to the skin of a living body is a z direction and directions parallel to the skin are an x direction and a y direction, red blood cells H move in various directions at various velocities in a manner that depends on the direction of the blood vessel. In the figure, velocity vectors of the red blood cells H are shown as the arrows.

FIG. 8(b) schematically shows a velocity distribution of red blood cells H at a particular moment. As shown in the figure, the velocity distribution of the red blood cells H spreads in various directions around the origin. A closed region K shown as the ellipse in FIG. 8(c) indicates the range of the velocity distribution of the red blood cells H described above. In the following description, the velocity distribution of the red blood cells H is indicated by such a closed region K. It should be noted that the velocity distribution of the red blood cells H increases/decreases in accordance with a change in pressure inside the blood vessel, which is caused by beating of the heart. Therefore, the elliptical shape K shown in FIG. 8(c) expands/contracts in accordance with beating of the heart.

[Regarding Configuration of General Laser Doppler Blood Flow Measurement Apparatus]

Figure 9:
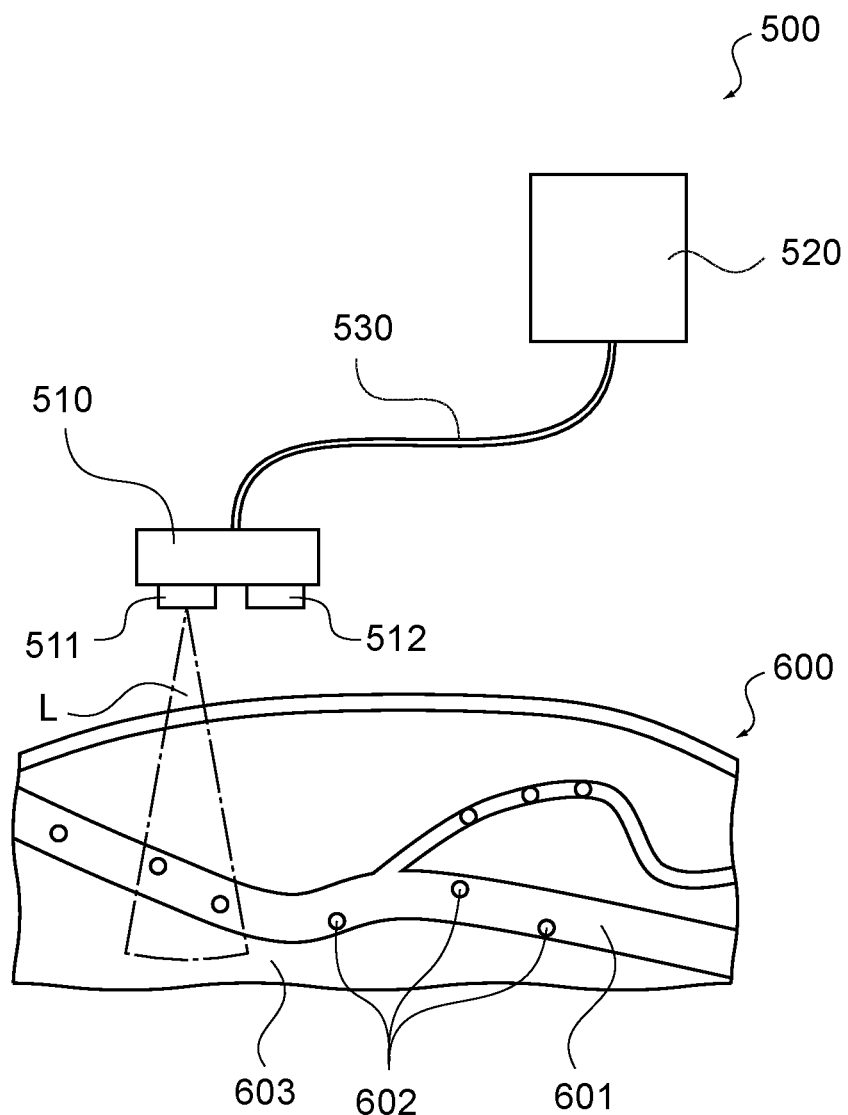
FIG. 9 A schematic diagram of a laser Doppler blood flow measurement apparatus having a general configuration.

A configuration of a laser Doppler blood flow measurement apparatus having a general configuration will be described as a comparative of the laser Doppler blood flow measurement apparatus according to the present embodiment. FIG. 9 is a schematic diagram of a laser Doppler blood flow measurement apparatus 500 having a general configuration.

As shown in FIG. 5, the laser Doppler blood flow measurement apparatus 500 (hereinafter, referred to as blood flow measurement apparatus 500) includes a sensor head 510 and an information processing apparatus 520. The sensor head 510 and the information processing apparatus 520 are connected through a signal line 530.

The sensor head 510 includes a light emitting unit 511 that emits laser light and a light receiving unit 512 that receives scattered light. The light emitting unit 511 is a laser light source, for example. The light receiving unit 512 is a photodiode, for example. The sensor head 510 is disposed close to or in close contact with a living body 600 that is a measurement target. The living body 600 has red blood cells 602 flowing through a blood vessel 601, and a stationary tissue 603. The stationary tissue 603 is a stationary living tissue other than blood.

In the blood flow measurement apparatus 500, a laser beam (in the figure, L) is emitted to the living body 600 from the light emitting unit 511. The laser light L is scattered by the red blood cells 602 and the stationary tissue 603. The scattered laser light L is received by the light receiving unit 512 and is converted into an electrical signal.

Figure 10:
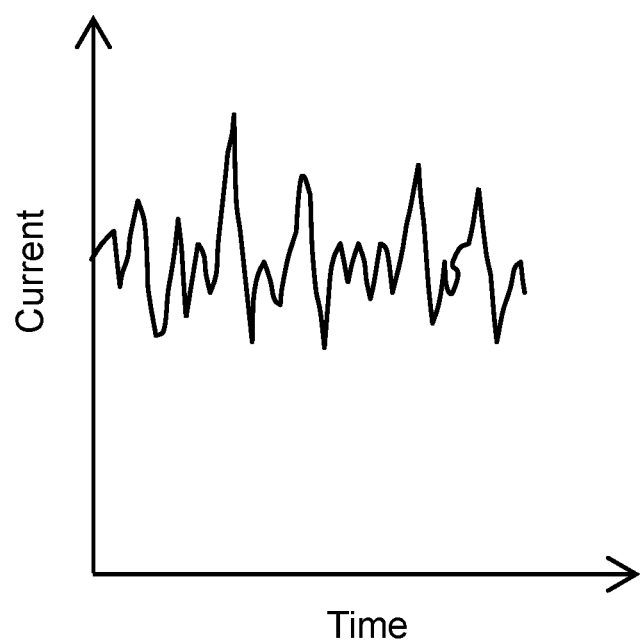
FIG. 10 An example of a beat signal output from a light receiving unit of the blood flow measurement apparatus.

FIG. 10 is an example of the electrical signal output from the light receiving unit 512. The scattered light incident on the light receiving unit 512 is light scattered by the red blood cells 602 moving through the blood flow and light scattered by the stationary tissue 603 that does not move. Therefore, the signal shown in FIG. 10 is an aggregate of many Doppler beats caused by the interference between both the scattered light beams. In this specification, a signal including such an aggregate of Doppler beats is referred to as a beat signal.

Figure 11:
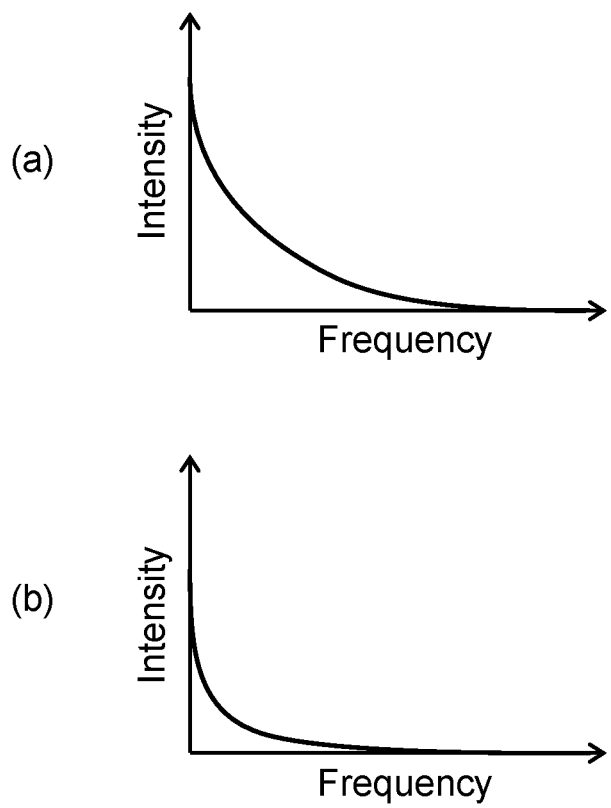
FIG. 11 An example of a signal processing result of the beat signal output from the light receiving unit of the blood flow measurement apparatus.

The information processing apparatus 520 obtains a beat signal from the sensor head 510 via the signal line 530 and performs signal processing such as Fourier transform. FIG. 11 shows an example of the signal processing result. FIG. 11(a) is a graph obtained by converting a beat signal measured at a fingertip into a frequency domain. FIG. 11(b) is a graph obtained by converting a beat signal measured at a wrist into a frequency domain.

The power spectra shown in these graphs correspond to intensity for each beat frequency, i.e., distribution density of red blood cells moving at a velocity corresponding to the frequency.

For example, the flow rate of the blood flow at the fingertip is higher than the flow rate of the blood flow at the wrist. In FIG. 11(a), the attenuation rate of the intensity with respect to the increase in beat frequency is lower than that in FIG. 11(b). As a result, it can be seen that the ratio of red blood cells at a higher motion velocity in FIG. 11(a) is higher than in FIG. 11(b). Further, the total area of the spectrum in FIG. 11(a) is wider than in FIG. 11(b). Thus, it can be seen that the number of red blood cells moving within an observation area is larger at the fingertip.

The information processing apparatus 520 is further capable of calculating higher-order blood flow-related information such as a time change (pulse) of the mean velocity of the blood flow, a pulse rate, and a flow velocity of the blood flow on the basis of a time-series change of the power spectrum of this beat signal.

[Regarding Disturbance Noise Caused by Body Motion]

The disturbance noise caused by the body motion, which can be generated in the blood flow measurement apparatus 500, will be described.

Figure 12:
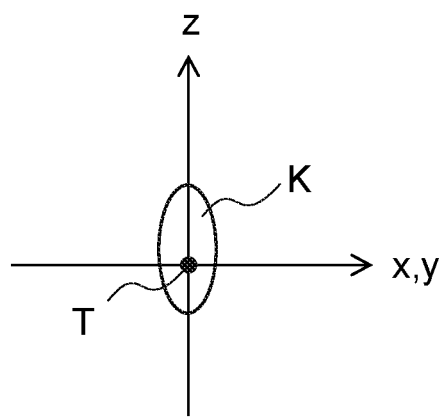
FIG. 12 A schematic diagram of the velocity distribution observed in a case where disturbance noise due to the body motion is not generated in the blood flow measurement apparatus.

FIG. 12 shows a velocity distribution observed in the living body 600 when disturbance noise due to body motion is not generated in the blood flow measurement apparatus 500.

As described above, the velocities of the red blood cells 602 spread around the origin inside the closed region K (see FIG. 4(c)) in accordance with the direction and the flow velocity of the blood flow.

At the origin, the motion velocity is 0 with respect to each of the x, y, and z directions. This is a velocity distribution of the stationary tissue 603. Here, the number of cells in the stationary tissue 603 is much greater than the number of red blood cells 602. Therefore, light scattered by the stationary tissue is greater than light scattered by the red blood cells. The velocity distribution of zero velocity caused by the stationary tissue 603 is significantly greater than the velocity distribution of the red blood cells 602. Therefore, a singular point T of the velocity distribution is formed at the origin.

When disturbance noise due to a body motion is not generated, the velocity distribution as shown in FIG. 12 is obtained. When disturbance noise due to a body motion is generated, the velocity distribution of the living body 600 apparently changes from the state shown in FIG. 12.

The disturbance noise due to the body motion can be classified into the following three categories.

1. Change in Blood Flow due to Body Motion
2. Shift of Sensor Head due to Body Motion
3. Relative Velocity between Sensor Head and Living Body due to Body Motion <1. Change in Blood Flow Due to Body Motion>

For example, when jogging is done in a state in which the sensor head 510 is mounted on the wrist, the blood flow is increased in velocity by centrifugal force of arm swing. Therefore, even if the measurement by the blood flow measurement apparatus 500 is correct, a measurement result that differs from the original blood flow velocity can be obtained.

This noise is overcome by the use of a low-pass filter that performs smoothing in a period longer than the frequency of the body motion or by a technique of obtaining the acceleration of the body motion through an acceleration sensor and eliminating components correlated to the acceleration, for example.

<2. Shift of Sensor Head Due to Body Motion>

When the mounting position of the sensor head 510 moves relative to the living body 600, noise is generated due to a difference in blood flow velocity between the mounting positions, a difference in luminance distribution which is caused by spatial speckles due to interference of laser light, a difference in epidermis property, a difference in laser irradiation angle with respect to the blood vessel, and the like.

This noise can be overcome by increasing the size of the light receiving unit 512 or devising a method of fixing the sensor head 510 to the living body, for example.

<3. Relative Velocity Between Sensor Head and Living Body Due to Body Motion>

Regarding the relative velocity between the sensor head 510 and the living body due to the body motion, more specifically the following four points can be mentioned.

3a. Doppler Beat Due to Relative Velocity Between Light Emitting Unit and Living Body 3b. Doppler Beat Due to Relative Velocity between Light Receiving Unit and Living Body 3c. Doppler Beat Due to Relative Angular Velocity between Light Emitting Unit and Living Body 3d. Doppler Beat Due to Relative Angular Velocity between Light Receiving Unit and Living Body {3a. Doppler Beat Due to Relative Velocity Between Light Emitting Unit and Living Body}

Figure 13:
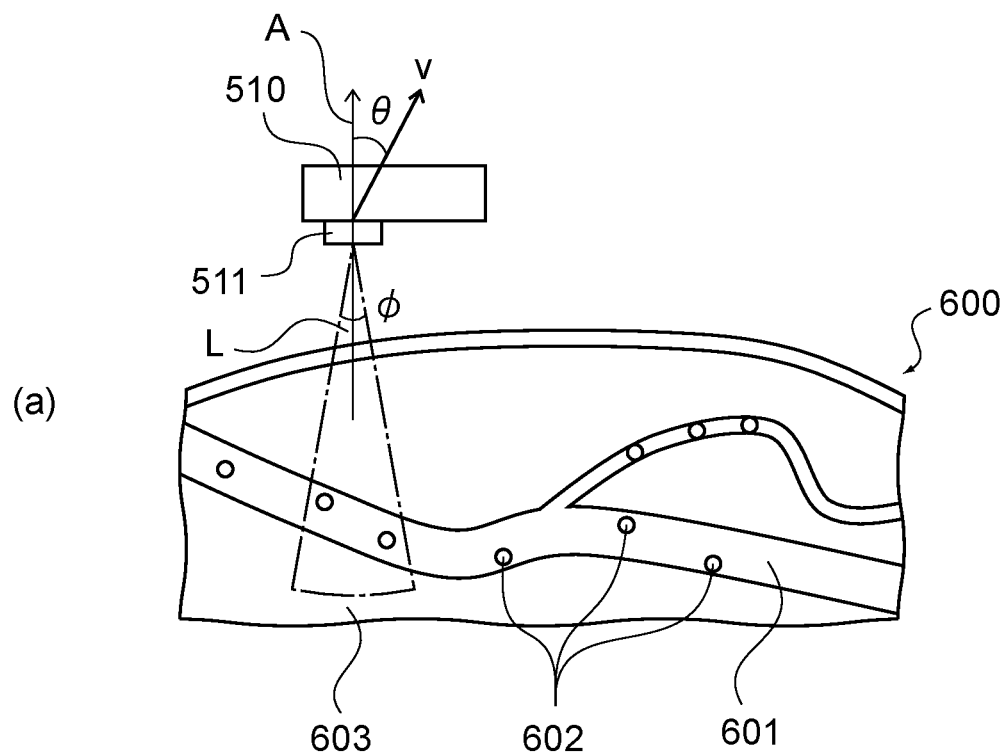
FIG. 13 A schematic diagram showing a Doppler beat due to a relative velocity between a light emitting unit of the blood flow measurement apparatus and a living body.
Figure 13:
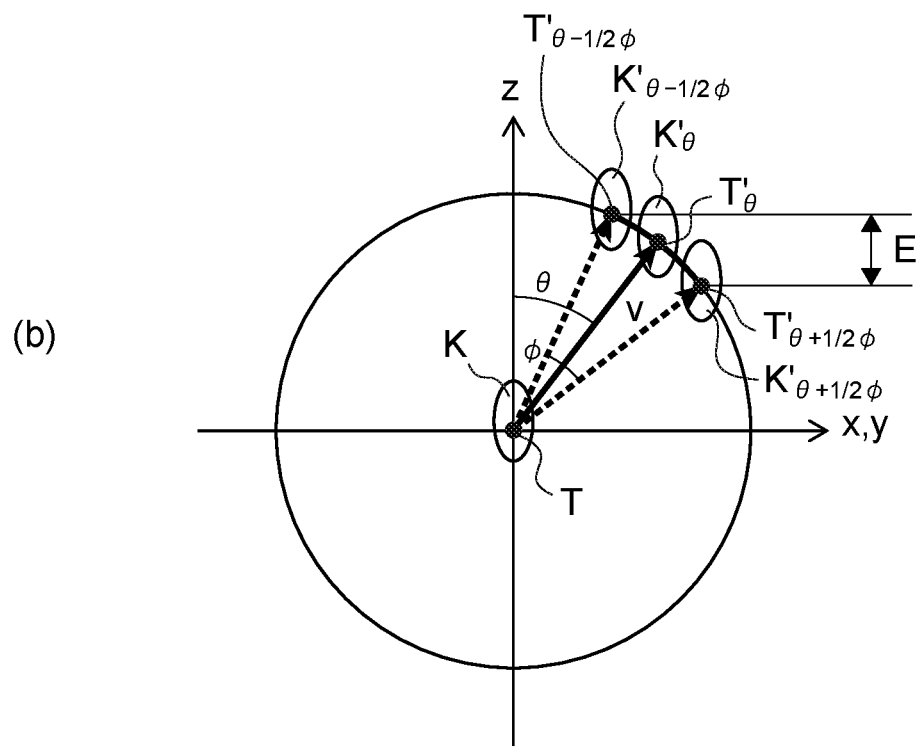

FIG. 13 is a schematic diagram showing a Doppler beat due to the relative velocity between the light emitting unit 511 and the living body 600. As shown in FIG. 13($a$), it is assumed that the light emitting unit 511 moves at the angle $\theta$ and the velocity v with respect to the optical axis A of the laser light L. It should be noted that the irradiation angle of the laser light L is defined as an angle $\phi$.

FIG. 13($b$) is a schematic diagram showing a velocity distribution of red blood cells in this case. When the light emitting unit 511 moves in a manner as described above, the relative velocity between the red blood cells and the light emitting unit 511 apparently moves to a closed region K' at a position deviated from the closed region K by a velocity vector v. Further, the singular point T moves to a point T' in a circle having a radius v. The angle formed by the optical axis of the laser light L and the velocity vector is distributed in a range of $\pm\frac{1}{2}\phi$ having $\beta$ as the center. Therefore, as shown in FIG. 13($b$), the closed region K' and the singular point T' of the red blood cell 602 and the stationary tissue 603 on each optical axis also move in the range of $\pm\frac{1}{2}\phi$ in the circle having the radius v. For example, the singular point T of the stationary tissue 603 on the optical axis moves to T'$_\theta$. The singular point T of the stationary tissue 603, which is positioned on a line at an angle $+\frac{1}{2}\phi$ from the optical axis, moves to T'$_{\theta+(\frac{1}{2})\phi}$. The singular point T of the stationary tissue 603, which is positioned on a line at an angle $-\frac{1}{2}\phi$ from the optical axis, moves to T'$_{\theta-(\frac{1}{2})\phi}$.

As described above, regarding the velocity of the stationary tissue 603 within the range of the angle $\phi$, the singular point T moves to the singular point T' having a spread at the angle $\theta$. The stationary tissue 603 is irradiated with the laser light L from the light emitting unit 511. The stationary tissue 603 at each location causes a Doppler shift corresponding to a different velocity. When they interfere upon light reception, they cause a Doppler beat, even though they are scattered light of the stationary tissues 603. In FIG. 13($b$), a maximum velocity difference that causes a Doppler beat at the singular point T is denoted by E. Base on (Expression 5) above, a frequency corresponding to the velocity difference E is at most $2\alpha_0 v \sin \theta((\frac{1}{2})\phi)$.

Therefore, the scattered light of the stationary tissue 603 which should not originally generate a beat signal generates a large beat signal caused by a motion of the light emitting unit 511, and the beat signal generated by a motion of a red blood cell cannot be detected.

{3b. Doppler Beat Due to Relative Velocity Between Light Receiving Unit and Living Body}

Figure 14:
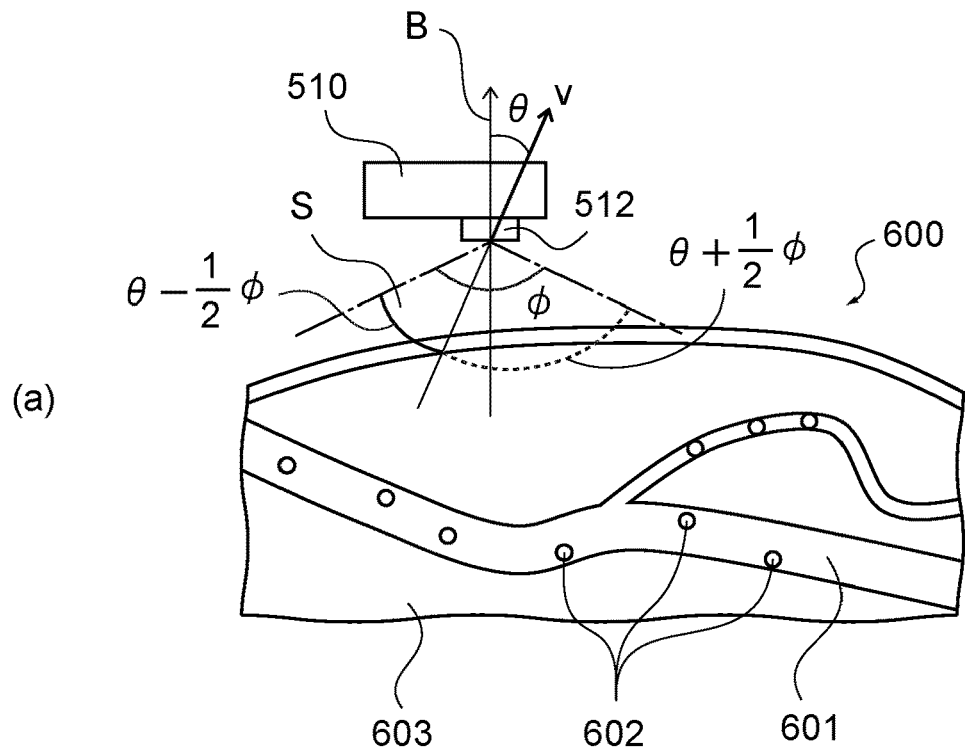
FIG. 14 A schematic diagram showing the Doppler beat the relative velocity between the light receiving unit of the blood flow measurement apparatus and the living body.
Figure 14:
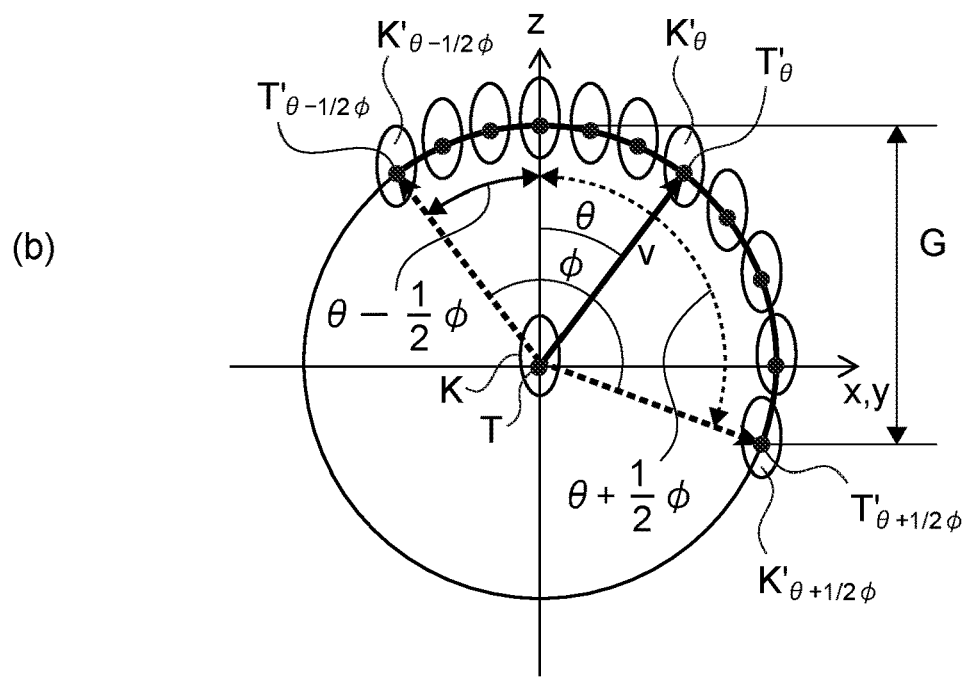

FIG. 14 is a schematic diagram showing a Doppler beat due to the relative velocity between the light receiving unit 512 and the living body 600. As shown in FIG. 14($a$), it is assumed that the light receiving unit 512 moves at the angle $\theta$ and the velocity v with respect to the optical axis B of the scattered light S. It should be noted that the incident angle of the scattered light S received by the light receiving unit 512 is an angle $\theta$.

FIG. 14($b$) is a schematic diagram showing a velocity distribution of red blood cells in this case. Scattering by the living body 600 is highly uniform scattering close to Lambertian scattering. Therefore, scattering by the living body 600 is performed in a wide range of irradiation angles. Therefore, scattered light S emitted from the wide range of the living body 600 is incident on a single point of the light receiving unit 512. That is, the angle $\theta$ formed by the scattered light S incident on the single point of the light receiving unit 512 is a large angle close to 180°.

Therefore, when the sensor head 510 moves in the manner as described above, cos $\theta$ in (Expression 2) above largely differs at each position of the stationary tissue 603, and the apparent closed area moves to a wide area as shown as K' in FIG. 14($b$).

Accordingly, the singular points T' at the respective moving destinations, that is, scattered light beams of the stationary tissue 603 cause Doppler beats each having a higher frequency. In FIG. 14($b$), a maximum width of the velocity difference between the singular points T° is denoted by G. Based on (Expression 5) above, a frequency of a beat G ranges from 0 to $\alpha_0 v\{1-\sin(\theta+(\frac{1}{2})\phi)\}$.

Therefore, the scattered light of stationary tissue 603, which should not originally generate a beat signal, generates a large beat signal due to a motion of the light receiving unit 512, and a beat signal generated by a motion of a red blood cell cannot be detected.

{3c. Doppler Beat Due to Relative Angular Velocity between Light Emitting Unit and Living Body/3d. Doppler Beat Due to Relative Angular Velocity between Light Receiving Unit and Living Body}

Figure 15:
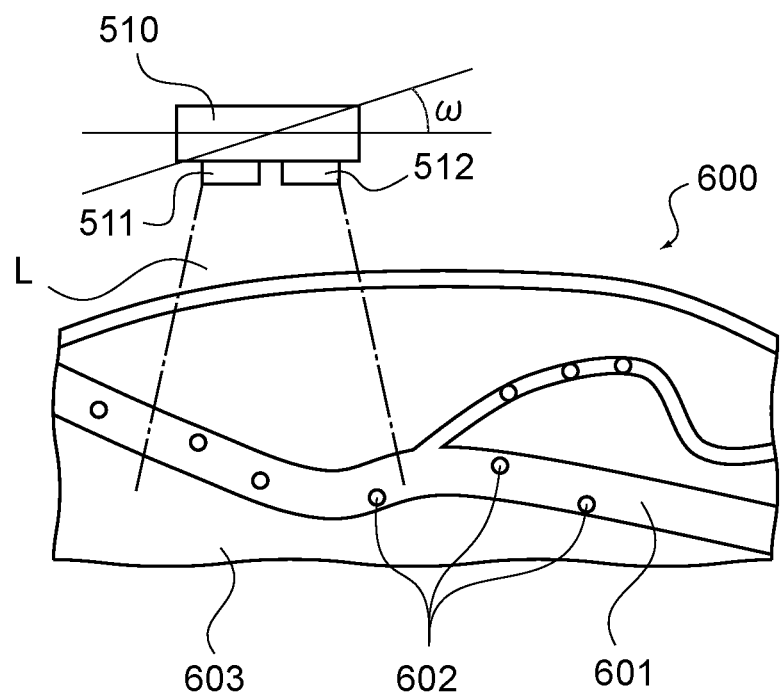
FIG. 15 A schematic diagram showing a Doppler beat due to an angular velocity between the light emitting unit and the light receiving unit of the blood flow measurement apparatus and the living body.

FIG. 15 is a schematic diagram showing a Doppler beat due to the angular velocity between the light emitting unit 511 and the light receiving unit 512 and the living body 600.

As shown in FIG. 15, when an angular velocity indicated by an angle $\omega$ is generated in the sensor head 510, a relative velocity is generated at one end of the irradiation spot of the laser light L such that the light emitting unit 511 and the light receiving unit 512 approach the living body 600. A relative velocity is generated at the other end of the irradiation spot such that the light emitting unit 511 and the light receiving unit 512 moves away from the living body 600.

Therefore, as in "3a. Doppler Beat Due to Relative Velocity Between Light Emitting Unit and Living Body" and "3b. Doppler Beat Due to Relative Velocity between Light Receiving Unit and Living Body" above, the scattered light of the stationary tissue 603 which should not originally generate a beat signal generates a large beat signal, and a beat signal generated by a motion of a red blood cell cannot be detected.

The blood flow measurement apparatus according to the present technology can prevent disturbance noise due to "3. Relative Velocity between Sensor Head and Living Body due to Body Motion".

First Embodiment

[Configuration of Blood Flow Measurement Apparatus According to First Embodiment]

Figure 16:
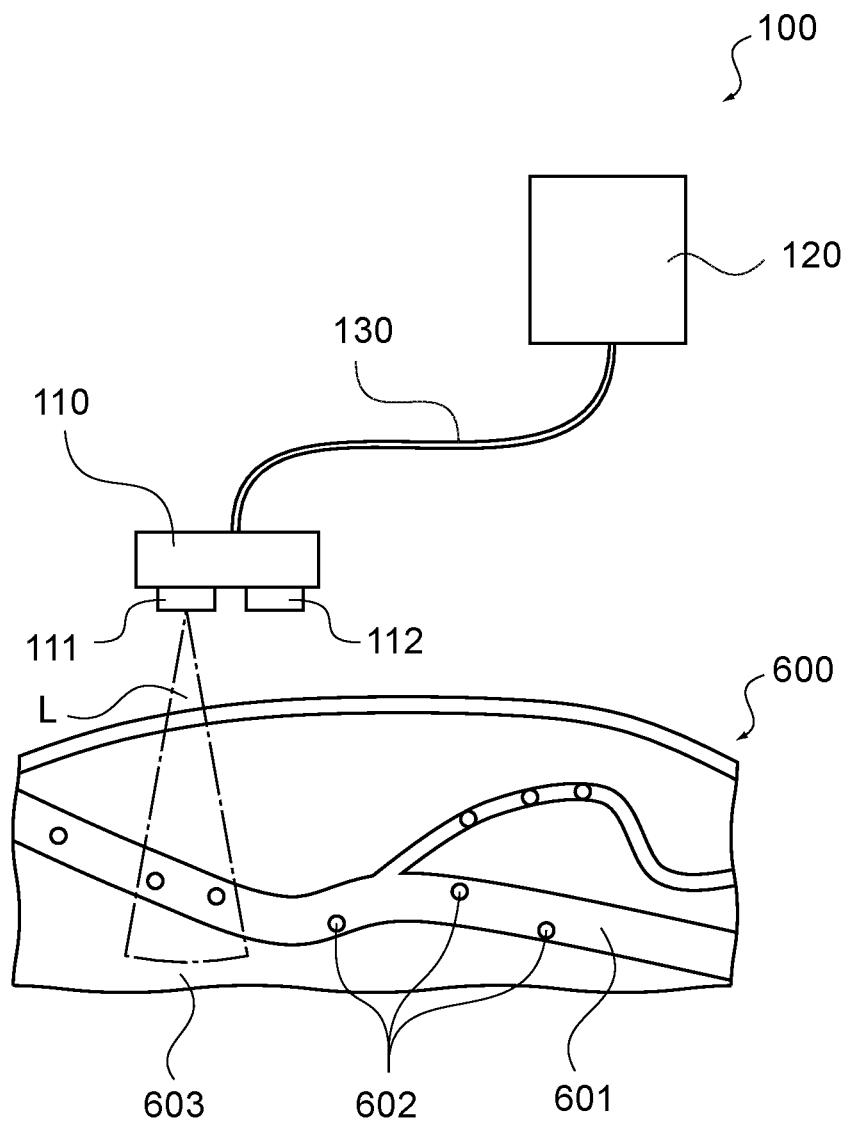
FIG. 16 A schematic diagram of a blood flow measurement apparatus according to a first embodiment of the present technology.
Figure 17:
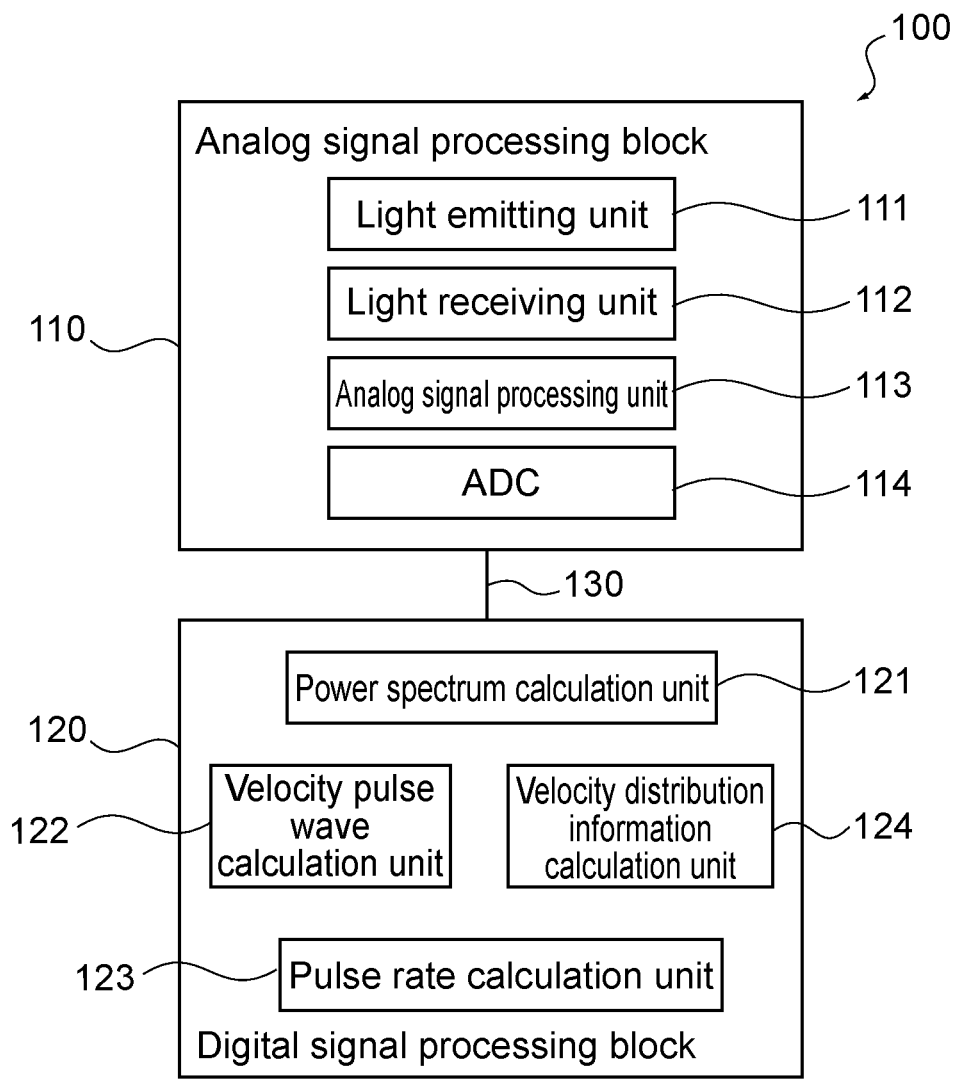
FIG. 17 A block diagram showing functions of the blood flow measurement apparatus.

A configuration of a blood flow measurement apparatus 100 according to a first embodiment of the present technology will be described. FIG. 16 is a schematic diagram of the blood flow measurement apparatus 100 according to the present embodiment. FIG. 17 is a block diagram showing functions of the blood flow measurement apparatus 100.

As shown in FIG. 16, the blood flow measurement apparatus 100 includes a sensor head 110 and an information processing apparatus 120. The sensor head 110 and the information processing apparatus 120 are connected through a signal line 130. The blood flow measurement apparatus 100 may be a wearable device worn by a user. The wearable device may be, for example, a head mounted display (HMD), smart ice glasses, a smart watch, a smart band, smart earphones, or the like.

Further, FIG. 16 shows a living body 600 which is a blood flow measurement target. The living body 600 has red blood cells 602 flowing through a blood vessel 601, and a stationary tissue 603.

As shown in FIG. 16, the sensor head 110 is disposed close to or in close contact with the living body 600. As shown in FIGS. 16 and 17, the sensor head 110 includes a light emitting unit 111, a light receiving unit 112, an analog signal processing unit 113, and an ADO 114.

The light emitting unit 111 irradiates the living body 600 with laser light L. The light receiving unit (sensor) 112 receives scattered light obtained when the laser light L is reflected by the living body 600. The light receiving unit (sensor) 112 converts the received scattered light into a beat signal. The light emitting unit 111 and the light receiving unit 112 are mounted on the sensor head 110 and the relative position relative to the sensor head 110 is fixed. Details of the light emitting unit 111 and the light receiving unit 112 will be described later. It should be noted that laser light is included in the coherent light and examples of laser light are described as an example of coherent light in the respective embodiments.

The analog signal processing unit 113 performs signal processing such as amplification on the beat signal output from the light receiving unit 112 and supplies it to the ADC 114.

The analog to digital converter (ADC) 114 converts the analog signal supplied from the analog signal processing unit 113 into a digital signal. The HMD 114 outputs the converted digital signal to the information processing apparatus 120 via the signal line 130.

As shown in FIG. 17, the information processing apparatus 120 includes a power spectrum calculation unit 121, a velocity pulse wave calculation unit 122, a pulse rate calculation unit 123, and a velocity distribution information calculation unit 124.

The power spectrum calculation unit 121 performs arithmetic processing such as Fourier transform for a predetermined time interval of the beat signal obtained from the ADC 114. Accordingly, the power spectrum calculation unit 121 calculates the power spectrum by converting the beat signal for each predetermined time into a frequency domain. The predetermined time interval is, for example, $\frac{1}{300}$ to $\frac{1}{10}$ seconds. The predetermined time is, for example, $\frac{1}{300}$ to $\frac{1}{10}$ seconds.

The velocity pulse wave calculation unit 122 calculates a velocity pulse wave on the basis of a time-series change of the power spectrum of the beat signal. The pulse rate calculation unit 123 calculates a pulse rate on the basis of the velocity pulse wave calculated by the velocity pulse wave calculation unit 122.

The velocity distribution information calculation unit 124 performs an operation such as integration processing on the power spectrum of the beat signal to thereby calculate velocity distribution information indicating a velocity distribution of the red blood cells 602.

The power spectrum calculation unit 121, the velocity pulse wave calculation unit 122, the pulse rate calculation unit 123, and the velocity distribution information calculation unit 124 function as a blood flow-related information calculation unit that calculates information regarding the flow of red blood cells (hereinafter, referred to as blood flow-related information). The blood flow-related information calculation unit may have another configuration capable of calculating the blood flow-related information.

The blood flow measurement apparatus 100 has the above-mentioned configuration. It should be noted that sensor head 110 functions as an analog signal processing block of the blood flow measurement apparatus 100 and the information processing apparatus 120 functions as a digital signal processing block.

The configuration of the blood flow measurement apparatus 100 is not limited thereto. Digital signal processing may be performed at the sensor head 110 and analog signal processing may be performed at the information processing apparatus 120. Further, not only a wired signal communication path but also a wireless signal communication path may be used for the signal line 130. Further, the sensor head 110 and the information processing apparatus 120 may be integrated.

[Operation of Blood Flow Measurement Apparatus According to First Embodiment]

An operation of the blood flow measurement apparatus 100 will be described.

As shown in FIG. 16, when the laser light L at the frequency $f_0$ is emitted from the light emitting unit 111 to the living body 600, the laser light L is scattered by the living body 600 and the scattered light is received by the light receiving unit 112. The scattered light includes scattered light at the frequency $f_0$ which is scattered by the stationary tissue 603 and scattered light at the frequency $f_0+\Delta f$ which is scattered by the red blood cells 602 moving through the blood flow and causes a Doppler shift.

The Doppler shift $\Delta f$ varies in a manner that depends on the rate of motion of the red blood cell 602 relative to the stationary tissue 603 (see FIG. 5). Therefore, the light receiving unit 112 outputs a beat signal that is an aggregate of many Doppler beats (see FIG. 10).

This beat signal is supplied to the power spectrum calculation unit 121 via the analog signal processing unit 113 and the ADC 114. The power spectrum calculation unit 121 converts the beat signal in the predetermined time interval for each predetermined time into a frequency domain and calculates a power spectrum of the beat signal (see FIG. 11).

Each of the velocity pulse wave calculation unit 122, the pulse rate calculation unit 123, and the velocity distribution information calculation unit 124 calculates blood flow-related information based on the power spectrum of the beat signal.

The blood flow measurement apparatus 100 performs the above-mentioned operation. Here, when disturbance noise due to body motion as described above is generated in the beat signal output by the light receiving unit 112, the blood flow cannot be accurately measured. However, in the blood flow measurement apparatus 100, disturbance noise due to body motion is prevented from being generated as follows.

[Configurations of Light Emitting Unit and Light Receiving Unit]

Figure 18:
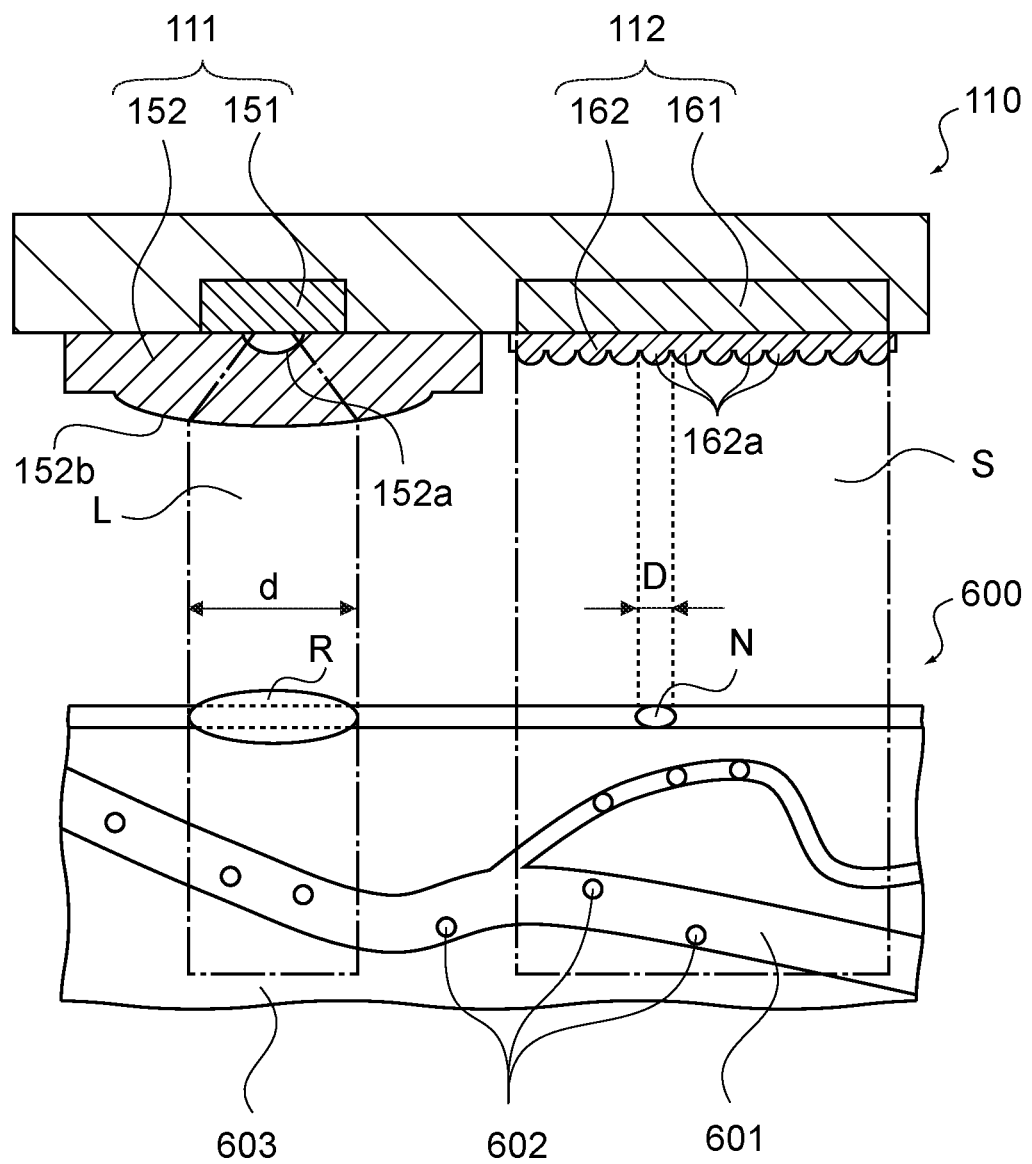
FIG. 18 A schematic diagram of a light emitting unit and a light receiving unit of the blood flow measurement apparatus.

FIG. 18 is a schematic diagram showing the light emitting unit 111 and the light receiving unit 112. As shown in the figure, the light emitting unit 111 includes a laser light source 151 and an irradiation light control unit 152.

The laser light source 151 is a light source of the laser light L. The laser light source 151 can be a common semiconductor laser device.

The irradiation light control unit 152 collimates the laser light L emitted from the laser light source 151 and controls the irradiation light diameter of the laser light L. The irradiation light diameter of the laser light L is equal to the diameter of a spot (R in the figure) of the laser light L on the surface of the living body 600. FIG. 18 shows an irradiation light diameter d controlled by the irradiation light control unit 152.

The irradiation light control unit 152 is constituted by an optical member such as glass. As shown in FIG. 18, the irradiation light control unit 152 includes a concave lens 152a and a convex lens 152b.

The concave lens 152a expands the laser light L incident from the laser light source 151 to the same diameter as the irradiation beam diameter d. The convex lens 152b collimates the laser light L enlarged by the concave lens 152a.

Thus, the laser light L having the irradiation light diameter d is emitted by the irradiation light control unit 152 to the living body 600. The irradiation light diameter d is favorably 0.5 mm or more and 2 mm or less.

It should be noted that the configuration of the light emitting unit 111 is not limited to that shown here. It is sufficient that the irradiation light control unit 152 can roughly collimate the laser light L and control the irradiation light diameter to a predetermined diameter. Various configurations that the light emitting unit 111 can take will be described later.

Further, as shown in FIG. 18, the light receiving unit 112 includes a measurement light receiving element 161 and an incident angle limiting unit 162.

The measurement light receiving element 161 photoelectrically converts light incident through the incident angle limiting unit 162 and outputs a beat signal. The measurement light receiving element 161 can be a photodiode having a general configuration. In the present technology, a large-size photodiode whose light receiving surface has a larger area as compared to the configuration of the conventional technology is favorably used.

The incident angle limiting unit 162 makes light from the living body 600, i.e., the scattered light S of the laser light L incident on the measurement light receiving element 161. Here, the incident angle limiting unit 162 is configured to limit the incident angle of the scattered light S incident on a single point of the measurement light receiving element 161 to be equal to or smaller than a predetermined angle and control the measurement light receiving element 161 to increase the aperture ratio as compared to a simple incident angle limiting mechanism with a single pin hole.

Specifically, the incident angle limiting unit 162 concentrates the incident scattered light S to a different point of the measurement light receiving element 161 for each incident angle.

Figure 19:
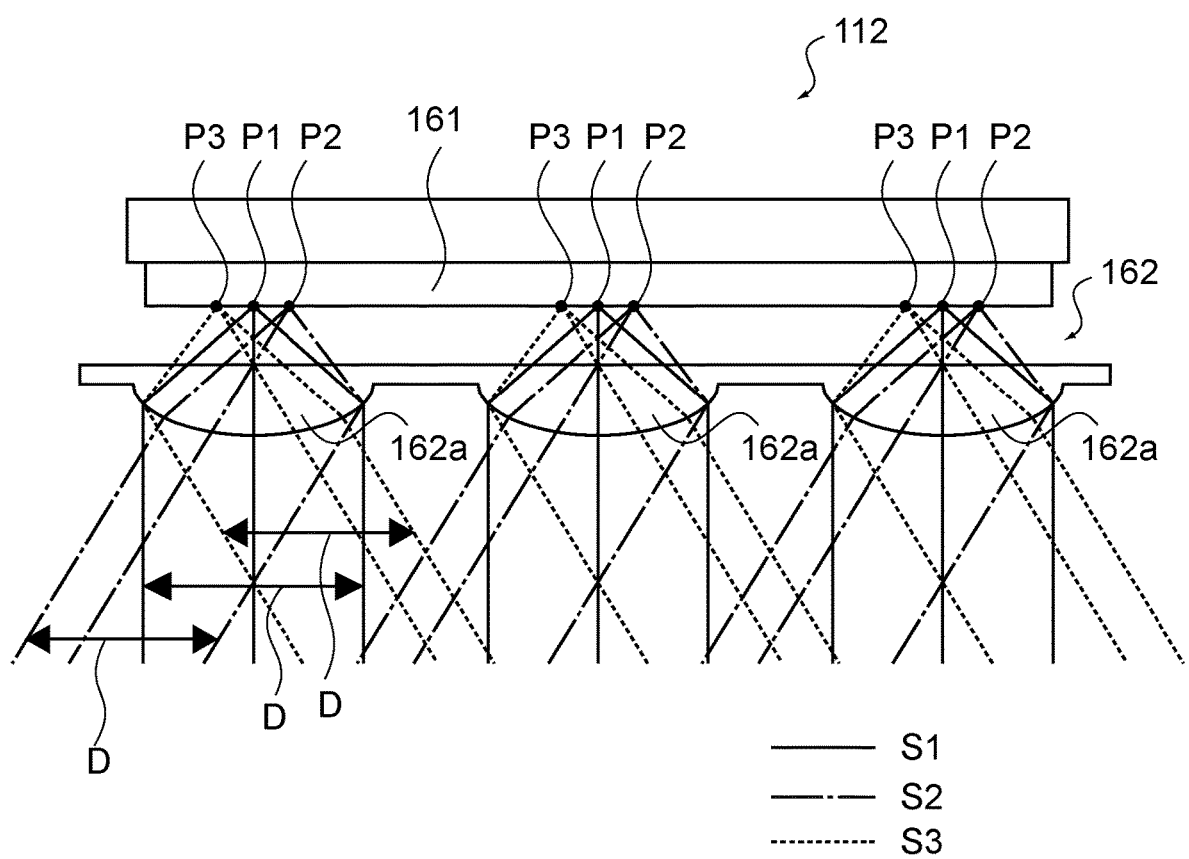
FIG. 19 A schematic diagram of an incident angle limiting unit of the light receiving unit of the blood flow measurement apparatus.

FIG. 19 is an enlarged view showing the incident angle limiting unit 162. As shown in the figure, the incident angle limiting unit 162 is constituted by an optical member and can be a lens array in which a plurality of lenses 162a is arranged. The lens 162a is not limited to a convex lens. The lens 162a may be a hologram lens or a Fresnel lens. The incident angle limiting unit 162 is arranged such that the light receiving surface of the light receiving element 161 is located at a position apart from the main point of each lens by approximately a focal length. In such an arrangement, the parallel light emitted from below in FIG. 19 is concentrated in the vicinity of the surface of the light receiving element 161.

In FIG. 19, scattered light that is incident at a certain incident angle with respect to the light receiving unit 112 will be referred to as scattered light S1. That is, components of the parallel light of the total scattered light, which has the certain incident angle, is the scattered light S1. Further, scattered light that is incident at an incident angle different from that of the scattered light S1 with respect to the light receiving unit 112 will be referred to as scattered light S2. In addition, scattered light that is incident at an incident angle different from those of the scattered light S1 and the scattered light S2 will be referred to as scattered light S3. The scattered light S2 and the scattered light S3 are also components of the parallel light, respectively.

As shown in the figure, the scattered light S1 is concentrated by each lens 162a to a point P1 of the measurement light receiving element 161. Further, the scattered light S2 is concentrated by each lens 162a to a point P2 on the measurement light receiving element 161. In addition, the scattered light S3 is concentrated by each lens 162a to a point P3 on the measurement light receiving element 161.

The point P1, the point P2, and the point P3 are different points from each other. Further, light incident on the incident angle limiting unit 162 at an incident angle different from those of the scattered light S1 to S3 is also concentrated by each lens 162a to a different point on the measurement light receiving element 161 in a manner that depends on the incident angle.

As an angle range of the scattered light incident on a single point of the measurement light receiving element 161 is narrower, β described above takes a smaller value, which is more favorable. More specifically, in a case where the angle between the scattered light S incident on a single point is limited to be equal to or smaller than 10°, β is smaller than 0.1, which can provide a sufficient effect.

In addition, by using the lens array for the incident angle limiting unit 162, the light beam diameter of the scattered light S concentrated to the single point of the measurement light receiving element 161 is limited to be smaller than the entire light beam diameter of the light incident on the measurement light receiving element 161. As shown in FIGS. 18 and 19, a light beam diameter D of the scattered light S concentrated to the single point of the measurement light receiving element 161 is equal to the diameter of the single lens 162a and is equal to a diameter of an observation region Ti facing this lens 162a on the living body 600.

Although the number of lenses 162a of the incident angle limiting unit 162 is arbitrary, it is favorable that the lenses 162a are disposed over the entire light receiving surface of the measurement light receiving element 161. Further, the diameters of the lenses 162a may be the same or may be different from each other.

It should be noted that the configuration of light receiving unit 112 is not limited to that shown here. It is sufficient that the incident angle limiting unit 162 can limit the incident angle of the scattered light incident on the single point of the measurement light receiving element 161 to be equal to or smaller than the predetermined angle. Various configurations that can be taken by the light receiving unit 112 will be described later.

[Effects of Light Emitting Unit and Light Receiving Unit]

Effects of the light emitting unit 111 and the light receiving unit 112 having the above-mentioned configurations will be described.

In the blood flow measurement apparatus 500 having the above-mentioned general configuration, "3a. Doppler Beat Due to Relative Velocity Between Light Emitting Unit and Living Body" caused by the relative motion between the sensor head 510 and the living body due to the body motion becomes a problem (see FIG. 13).

Figure 20:
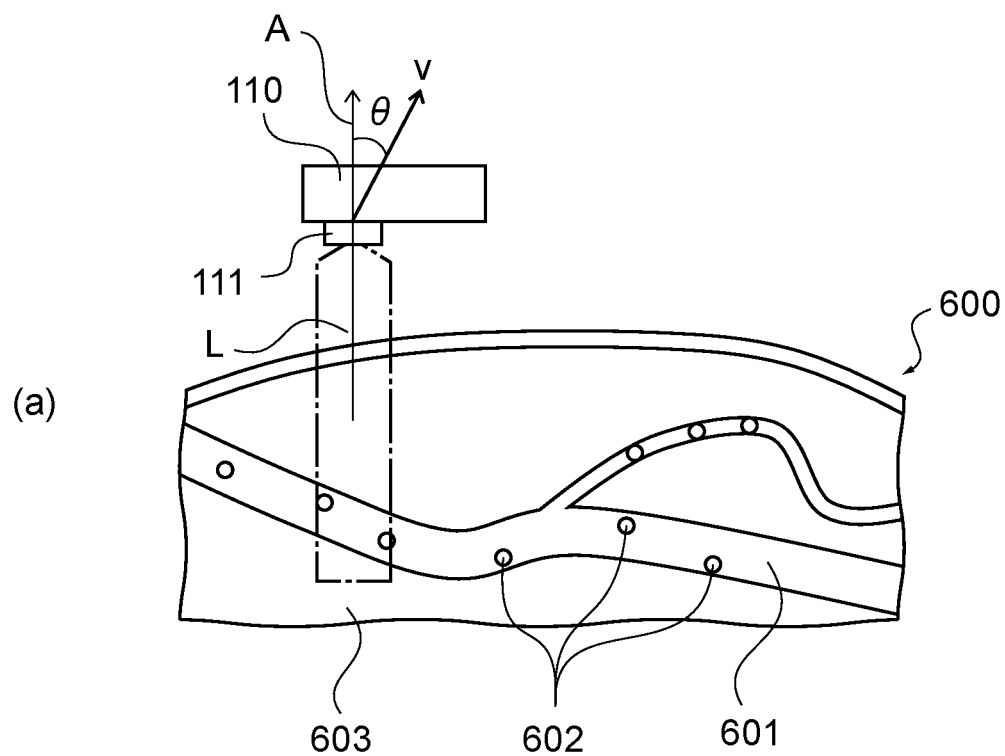
FIG. 20 A schematic diagram showing effects of the blood flow measurement apparatus.
Figure 20:
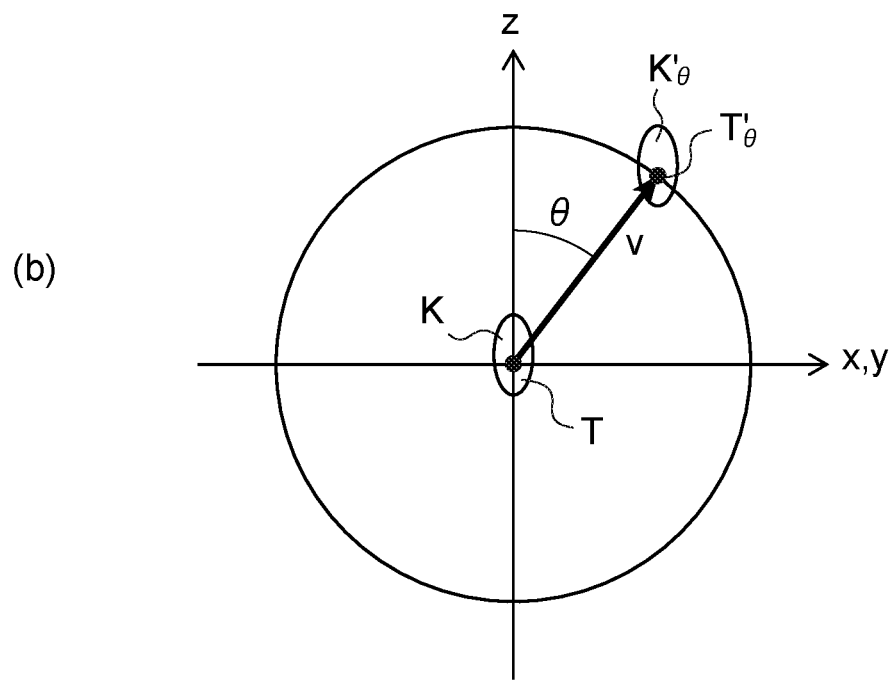

In the light emitting unit 111 in the present embodiment, this "3a. Doppler Beat Due to Relative Velocity Between Light Emitting Unit and Living Body" can be overcome. FIG. 20 is a schematic diagram showing this effect.

As described above, at the light emitting unit 111, the laser light L emitted from the laser light source 151 is collimated by the irradiation light control unit 152. Therefore, as shown in FIG. 20(a), the incident angle of the laser light L at each position of the stationary tissue 603 is the same even when the light emitting unit 111 is moving at the angle θ and the velocity v.

Accordingly, in (Expression 1) above, cos θ takes the same value at each position of the stationary tissue 603 and the velocity distribution moves to the same position in accordance with the velocity v as shown in FIG. 20(b). Therefore, there is no Doppler beat between the stationary tissues 603 indicated by the singular points T' (having a velocity difference denoted by E in FIG. 13 and the beat signal caused by the motion of the red blood cell to be detected is maintained. The generation of the beat signal between the stationary tissues 603, which is noise, is suppressed, and the beat signal generated by the motion of the red blood cell to be detected which is the measurement target, is maintained. Therefore, sensing of the signal is maintained.

In addition, in the blood flow measurement apparatus 500 having the above-mentioned general configuration, "3b. Doppler Beat Due to Relative Velocity between Light Receiving Unit and Living Body" caused by the relative motion between the sensor head 510 and the living body due to the body motion becomes a problem (see FIG. 14).

Figure 21:
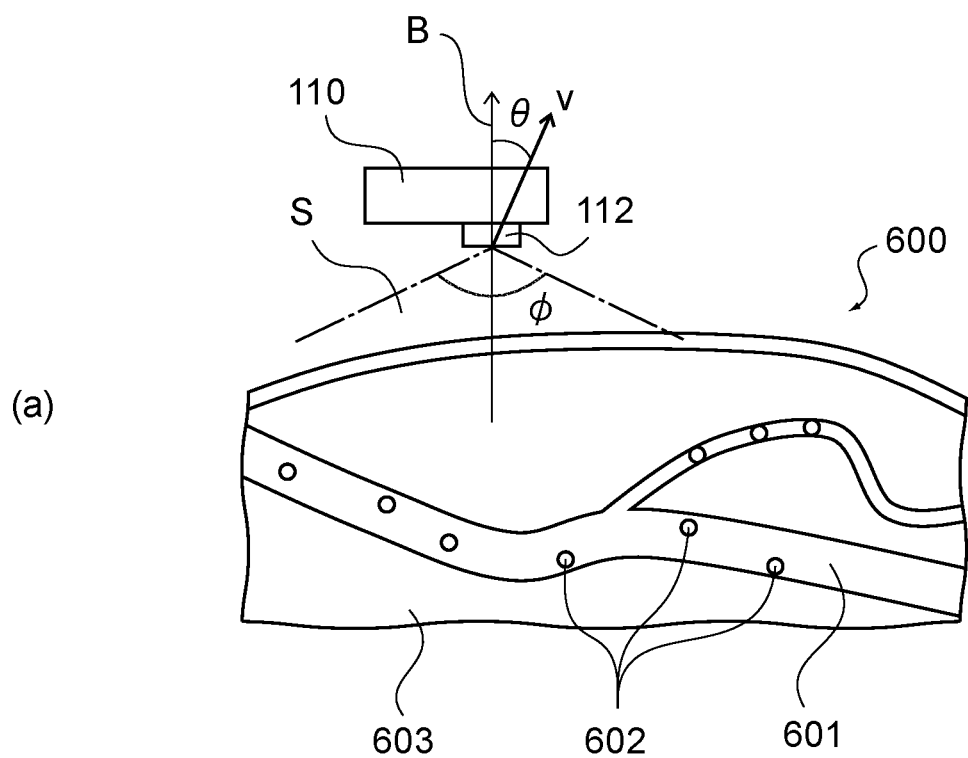
FIG. 21 A schematic diagram showing effects of the blood flow measurement apparatus.
Figure 21:
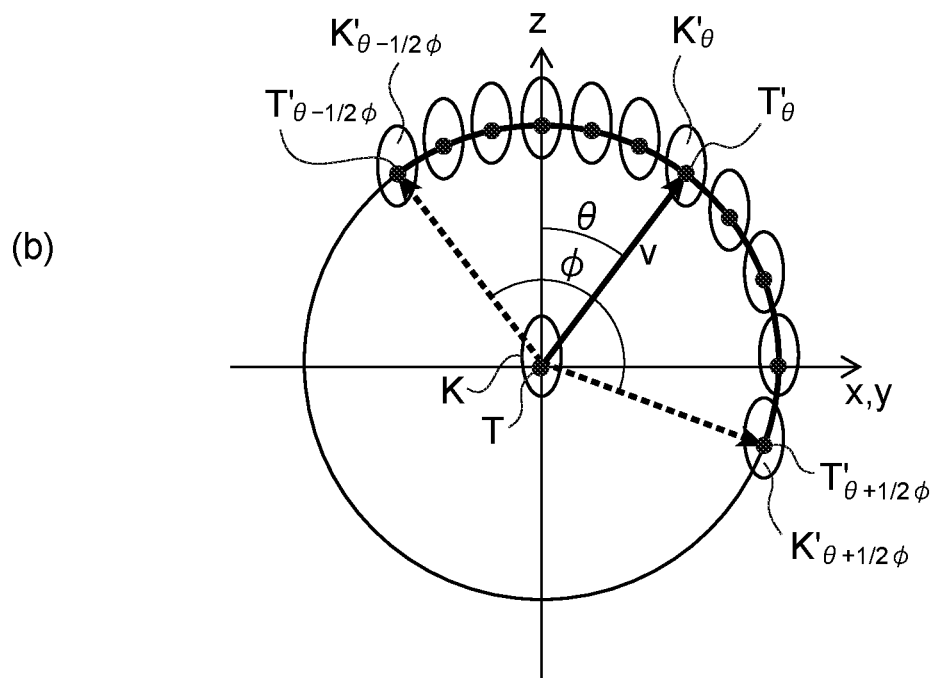

In the light receiving unit 112 in the present embodiment, "3b. Doppler Beat Due to Relative Velocity between Light Receiving Unit and Living Body" can also be overcome. FIG. 21 is a schematic diagram showing this effect.

As shown in FIG. 21(a), when the light receiving unit 112 is moving at the angle θ and the velocity v, the irradiation angle θ of the scattered light S is large. Therefore, the apparent velocity distribution of the stationary tissue 603 moves to each position (see FIG. 14(b)).

Here, as described above, in the light receiving unit 112, the incident angle limiting unit 162 limits the incident angle of the scattered light S incident on the single point of the measurement light receiving element 161 to be equal to or smaller than the predetermined angle. Therefore, scattered light S at a different incident angle with respect to the incident angle limiting unit 162 is concentrated at a different point on the measurement light receiving element 161 (see FIG. 19).

Thus, scattered light beams S at different incident angles with respect to the incident angle limiting unit 162 do not interfere with each other. As shown in FIG. 21(b), even if the apparent velocity distribution of the stationary tissue 603 is different, the Doppler beat (G in FIG. 14) is not generated between the singular points T'. At each point, the Doppler beat is generated in a combination of each closed region K' and the singular point T'. Therefore, the beat signal caused by the motion of the red blood cell to be detected is maintained. The beat signal between T' at different incident angles, which is a disturbance signal, is suppressed and the beat signal caused by the motion of red blood cell that is the measurement target is maintained. Therefore, sensing of the signal is maintained.

Further, in the blood flow measurement apparatus 500 having the above-mentioned general configuration, "3c. Doppler Beat Due to Relative Angular Velocity between Light Emitting Unit and Living Body/3d. Doppler Beat Due to Relative Angular Velocity between Light Receiving Unit and Living Body" caused by a relative motion between the sensor head 510 and the living body due to the body motion becomes a problem.

Figure 22:
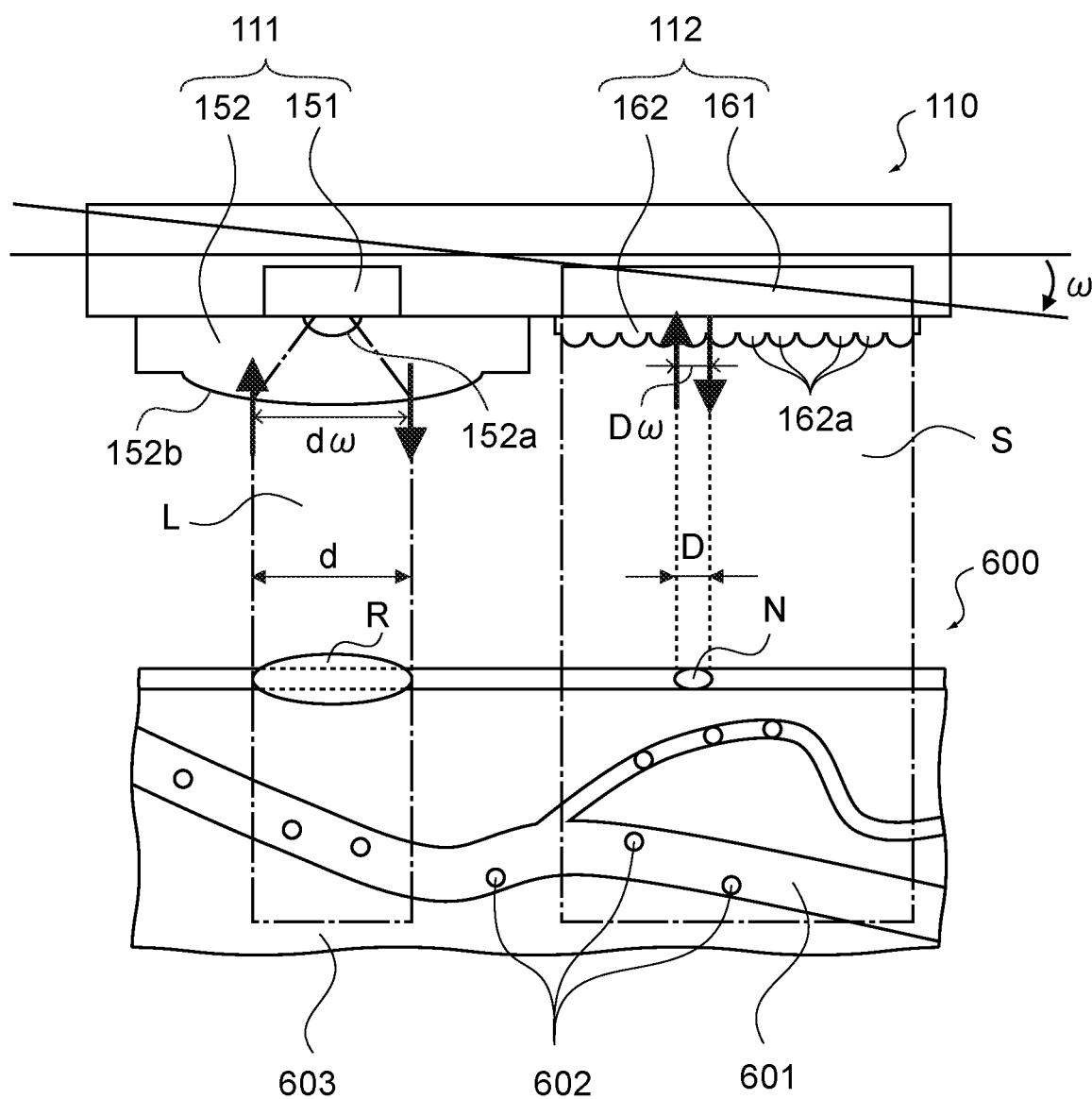
FIG. 22 A schematic diagram showing effects of the blood flow measurement apparatus.

In the light emitting unit 111 and the light receiving unit 112 in the present embodiment, "3c. Doppler Beat Due to Relative Angular Velocity between Light Emitting Unit and Living Body/3d. Doppler Beat Due to Relative Angular Velocity between Light Receiving Unit and Living Body" can be also overcome. FIG. 22 is a schematic diagram showing this effect.

As shown in the figure, the irradiation light control unit 152 collimates the laser light L, such that laser beams at a plurality of relative velocities are not emitted to a particular point of the stationary tissue 603. Further, the irradiation spot R of the laser light L has the irradiation light diameter d. Therefore, a maximum velocity difference in the irradiation spot R is dω.

Further, the incident angle limiting unit 162 limits the region in which light is concentrated to the single point of the measurement light receiving element 161 to an observation region N. The observation region N and the lens 162a have the diameter D. Therefore, maximum velocity difference of the scattered light concentrated to the measurement light receiving element 161 through the single lens 162a is Dω.

Thus, the relative velocity distribution obtained by combining the factors of the light emitting unit 111 and the light receiving unit 112 falls within the range of (d+D)ω. Therefore, if the diameter D of the lens 162a is reduced, the Doppler beat due to the relative angular velocity of the sensor head 110 is determined in a manner that depends on the irradiation light diameter d.

By reducing the irradiation light diameter d through the irradiation light control unit 152 in this manner, "3c. Doppler Beat Due to Relative Angular Velocity between Light Emitting Unit and Living Body/3d. Doppler Beat Due to Relative Angular Velocity between Light Receiving Unit and Living Body" can be overcome.

Specifically, the irradiation light diameter d is favorably 2 mm or less. On the other hand, if the irradiation light diameter d is too small, an influence due to a change in position of the sensor head 110 becomes large. Therefore, the spot diameter is favorably 0.5 mm or more. From the above, it is favorable that the irradiation light diameter d is 0.5 mm or more and 2 mm or less. It should be noted that the irradiation shape is not limited to the circular shape. The irradiation shape may be a shape having a long-side direction and a short-side direction, for example, an ellipse or a rectangle. The relative angular velocity of the sensor head 110 may have axial anisotropy in a manner that depends on the shape and mounting position of the sensor device. For example, in a case of mounting the sensor head to a watch-type device, rotation along an axis perpendicular to the dial of the watch is unlikely to occur, and further, rotation along an axis in the 3 o'clock-9 o'clock direction on the dial of the analog watch is also unlikely to occur. On the other hand, regarding rotation along the 12 o'clock-6 o'clock direction on the dial of the analog watch, a large angular velocity motion is generated by arm swing in walking or the like. In such a case, by arranging the long-side direction of the irradiation shape in parallel with the rotation axis having a high angular velocity, it is possible to enhance the resistance to the relative angular velocity motion while maintaining the irradiation area and maintaining the resistance to the change in position.

In addition, by using the incident angle limiting unit 162, the light receiving unit 112 can increase the area of the measurement light receiving element 161 while preventing disturbance noise caused by "Relative Velocity between Sensor Head and Living Body due to Body Motion" as described above.

With this enlargement of the measurement light receiving element 161, it is also possible to reduce the disturbance noise caused by "2. Shift of Sensor Head due to Body Motion" above.

Figure 23:
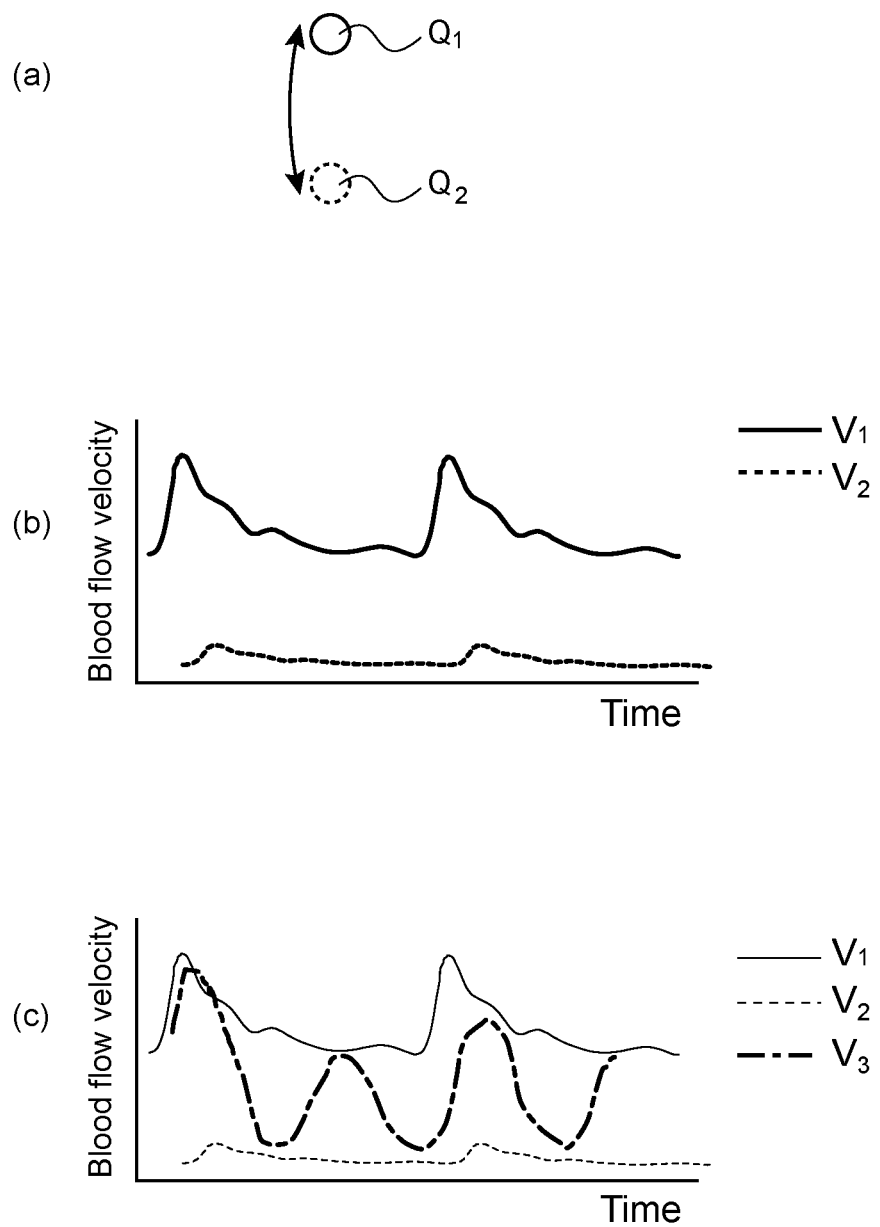
FIG. 23 A schematic diagram showing effects of the blood flow measurement apparatus.
Figure 24:
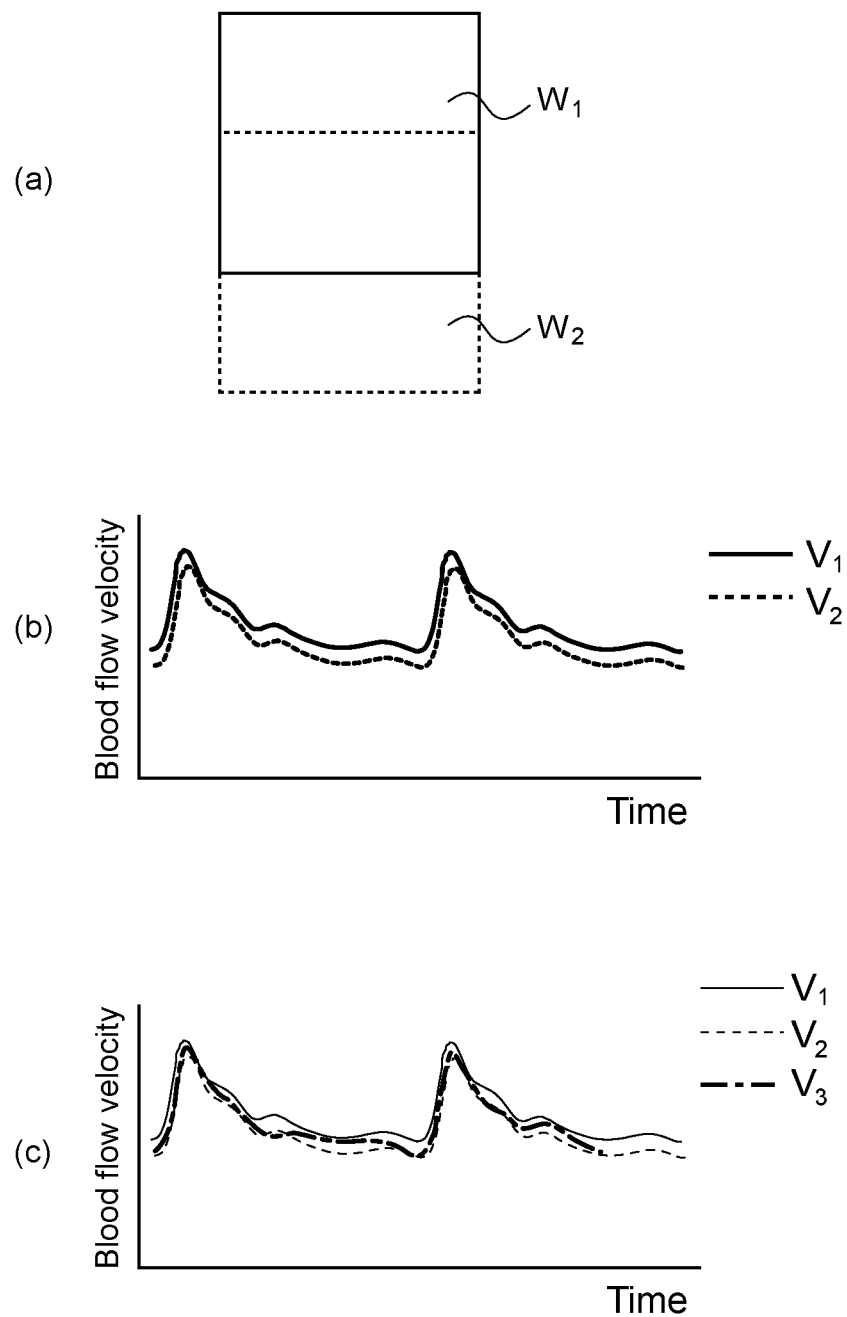
FIG. 24 A schematic diagram showing effects of the blood flow measurement apparatus.

FIGS. 23 and 24 are schematic diagrams each showing this effect. FIG. 23 shows a case where the area of the measurement light receiving element 161 is small. FIG. 24 shows a case where the area of the measurement light receiving element 161 is large.

As shown in FIG. 23(a), when the measurement light receiving element 161 having the small area vibrates due to the shift of the sensor head 110, the observation region facing the measurement light receiving element 161 in the living body 600 moves between the region $Q_1$ and the region $Q_2$.

In FIG. 23(b), $V_1$ is an actual blood flow velocity at the region $Q_1$ and $V_2$ is an actual blood flow velocity at the region $Q_2$. The region $Q_1$ has a higher blood flow velocity than the region $Q_2$, and is, for example, a region including many blood vessels extending toward the epidermis.

FIG. 23(c) shows the blood flow velocity $V_3$ measured on the basis of the Doppler beat in this case. As shown in the figure, the measured blood flow velocity $V_3$ is caused by the motion of the measurement light receiving element 161 between the region $Q_1$ and the region $Q_2$. This is largely different from the blood flow velocity $V_1$ and the blood flow velocity $V_2$ which are the original measurement targets.

On the other hand, as shown in FIG. 24(a), it is assumed that the measurement light receiving element 161 having a large area vibrates due to the shift of the sensor head 110 and the observation region facing the measurement light receiving element 161 in the living body 600 moves between a region $W_1$ and a region $W_2$.

In FIG. 24(b), $V_1$ is the actual blood flow velocity at the region $W_1$ and $V_2$ is the actual blood flow velocity at the region $W_2$. As shown in FIG. 24(a), even if the measurement light receiving element 161 vibrates, the measurement light receiving element 161 has the large area, such that the region $W_1$ and the region $W_2$ overlap. Therefore, in FIG. 24(b), the blood flow velocity $V_1$ and the blood flow velocity $V_2$ have a small difference.

Accordingly, as shown in FIG. 24(c), the blood flow velocity $V_3$ measured on the basis of the Doppler beat has a shape similar to those of the blood flow velocity $V_1$ and the blood flow velocity $V_2$, and the pulse wave is measured in the same manner as the blood flow velocity $V_1$ and the blood flow velocity $V_2$ which are the original measurement targets irrespective of vibration of the measurement light receiving element 161.

As described above, in the blood flow measurement apparatus 100, the laser beam is collimated by providing the irradiation light control unit 152 in the light emitting unit 111. Accordingly, the angles of the laser light beams entering the respective positions of the living body 600 are set to be the same, and a Doppler beat can be prevented from being generated between the stationary tissues 603.

Further, by controlling the light diameter of the laser light L through the irradiation light control unit 152, it is possible to achieve both the resistance to a shift of the light emitting unit 111 and the resistance to the relative angular velocity of the light emitting unit 111.

In addition, the angle of the scattered light incident on the single point of the measurement light receiving element 161 is limited by providing the incident angle limiting unit 162 in the light receiving unit 112. Accordingly, it is possible to prevent interference between the scattered light beams at different incident angle and to prevent a Doppler beat from being generated between the stationary tissues 603.

Further, by providing the incident angle limiting unit 162, it is possible to increase the size of the measurement light receiving element 161, to reduce the power consumption by increasing the utilization efficiency of light, and it is possible to reduce the influence due to the change in position of the light receiving unit 112.

[Variations of Light Emitting Unit]

Figure 25:
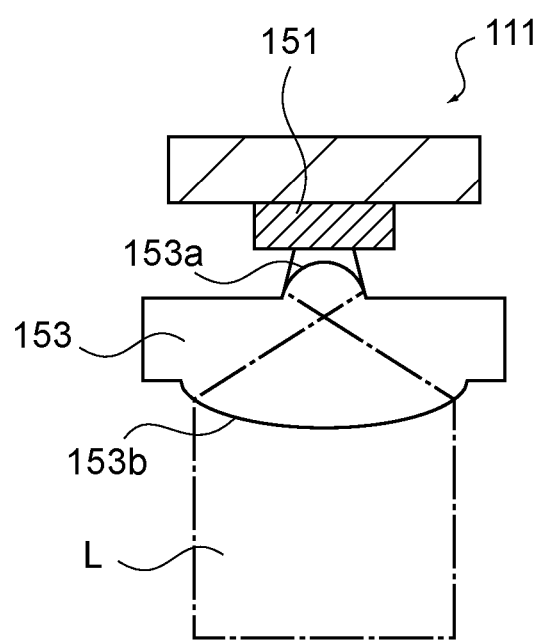
FIG. 25 A schematic diagram showing another configuration of the light emitting unit of the blood flow measurement apparatus.
Figure 26:
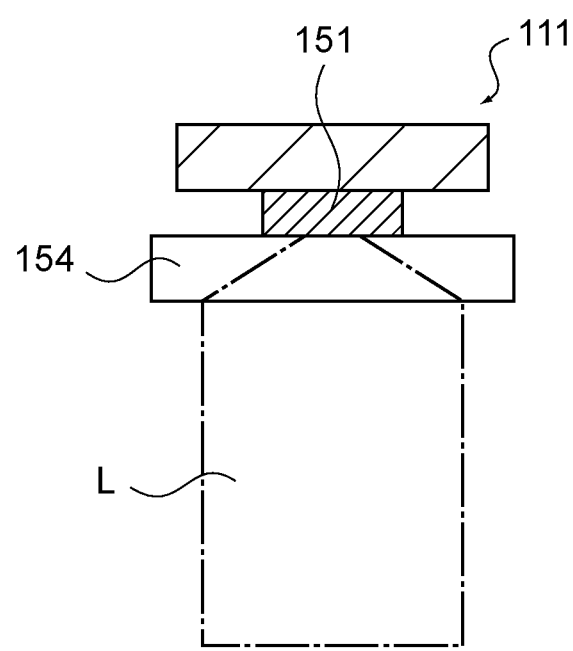
FIG. 26 A schematic diagram showing another configuration of the light emitting unit of the blood flow measurement apparatus.

The light emitting unit 111 is not limited to the above-mentioned configuration. It is sufficient that the configuration of the light emitting unit 111 is capable of substantially collimating the laser light L and controlling the spot diameter to the predetermined diameter. FIGS. 25 and 26 are schematic diagrams each showing the light emitting unit 111 having another configuration.

As shown in FIG. 25, the light emitting unit 111 may include a laser light source 151 and an irradiation light control unit 153. The irradiation light control unit 153 includes a convex lens 153a and a convex lens 153b. The convex lens 153a magnifies the laser light L incident from the laser light source 151. The convex lens 153b collimates the laser light L magnified by the convex lens 153a.

Further, as shown in FIG. 26, the light emitting unit 111 may include a laser light source 151 and an irradiation light control unit 154. The irradiation light control unit 154 can be a hologram lens capable of magnifying and collimating the laser light L incident from the laser light source 151.

Further, the light emitting unit 111 is not limited to those including the laser light source and the irradiation light control unit. The light emitting unit 111 may include only the laser light source. For example, vertical cavity surface emitting LASER (VCSEL) devices are laser devices capable of emitting relatively parallel laser light beams. The irradiation angle of the laser light source itself is favorable as the laser light source of the light emitting unit 111 not provided with the irradiation light control unit.

[Variations of Light Receiving Unit]

The light receiving unit 112 is not limited to the above-mentioned configuration. The light receiving unit 112 only needs to have a configuration to limit the incident angle of the scattered light S incident on the single point of the measurement light receiving element 161 to be equal to or smaller than the predetermined angle and to control the measurement light receiving element 161 to increase the aperture ratio. FIGS. 27 to 35 are schematic diagrams each showing the light receiving unit 112 having another configuration.

Figure 27:
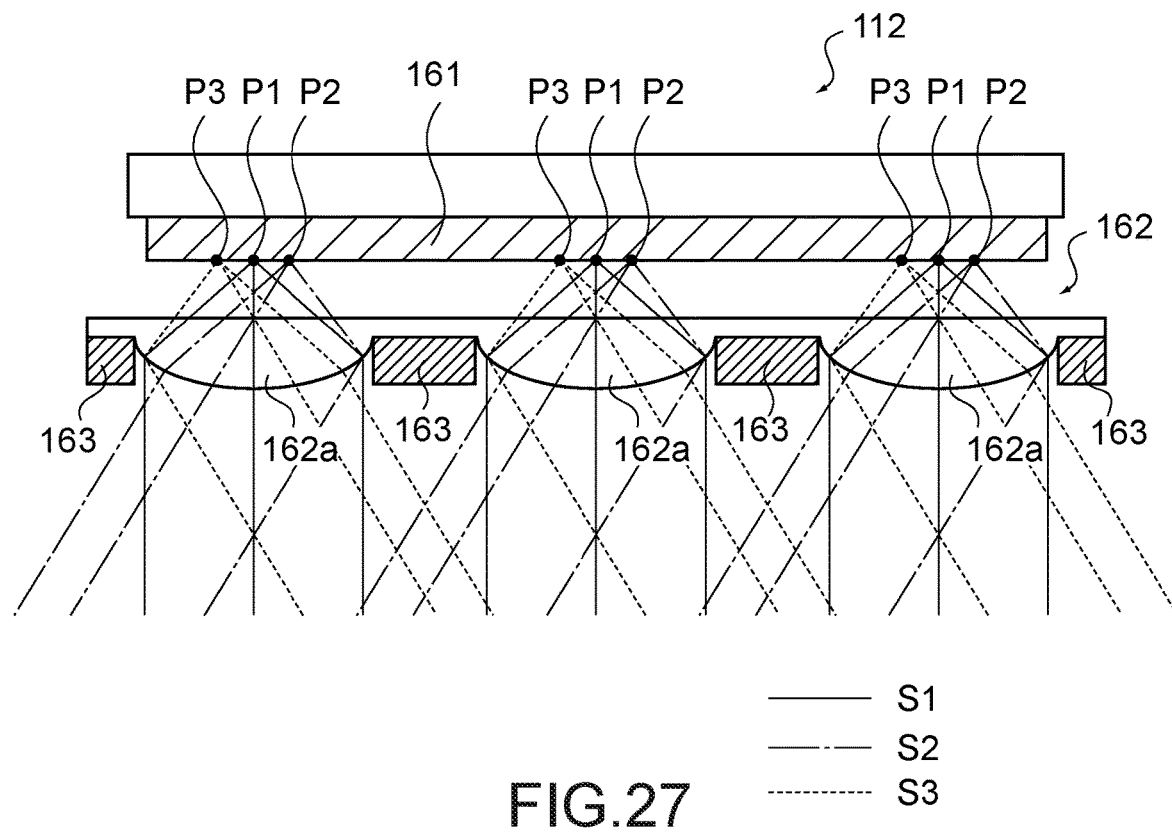
FIG. 27 A schematic diagram showing another configuration of the light receiving unit of the blood flow measurement apparatus.

As shown in FIG. 27, the incident angle limiting unit 162 may further include light shields 163. The light shields 163 are disposed between the lens array 162a and the measurement target and shield scattered light that enters the portions between the lenses 162a. It should be noted that the lens 162a is not limited to the convex lens. The lens 162a may be a hologram lens or a Fresnel lens. The same applies to each of the following configurations.

Figure 28:
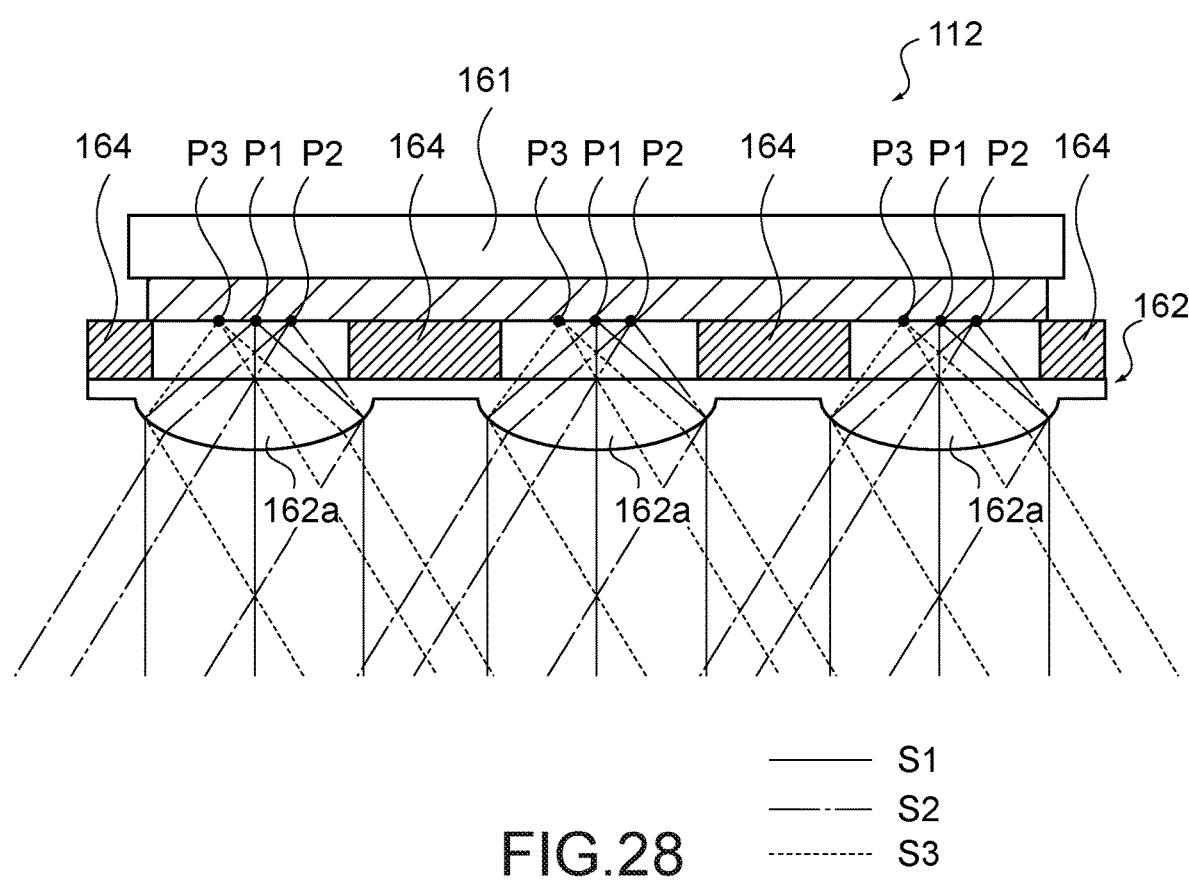
FIG. 28 A schematic diagram showing another configuration of the light receiving unit of the blood flow measurement apparatus.

Accordingly, scattered light can be prevented from entering the measurement light receiving element 161 from portions between the lenses 162a and a Doppler beat uncorrelated with the signal to be measured on the basis of the scattered light can be prevented from being generated. Further, by adjusting the angle of view overlapping the adjacent lenses 162a, it is possible to suppress the variation of the amount of light projected on the light receiving surface when the living body 600 moves and to enhance the resistance to the position dependency of the blood flow rate. In addition, in a case of using a paved-type lens array with sufficiently small portions between the lenses 162a, the light shields 163 and the lens array 162a do not need to be strictly aligned. In addition, if the height and the light shield spacing satisfy a predetermined condition, it is unnecessary to establish a one-to-one relationship with each lens. The predetermined condition is to limit the range of the incident angle such that the light that has passed through the lens 162a is not incident on the same point on the photosensitive surface as the light that has passed through another lens 162a, Further, as shown in FIG. 28, the incident angle limiting unit 162 may further include light shields 164. The light shields 164 are disposed between the lens array and the measurement light receiving element 161 and can prevent scattered light from entering the measurement light receiving element 161 from portions between the adjacent lens 162a and prevent the Doppler beat from being generated by the scattered light. Further, it is possible to enhance the resistance to the position dependency of the blood flow rate as in the light shields 163.

Figure 29:
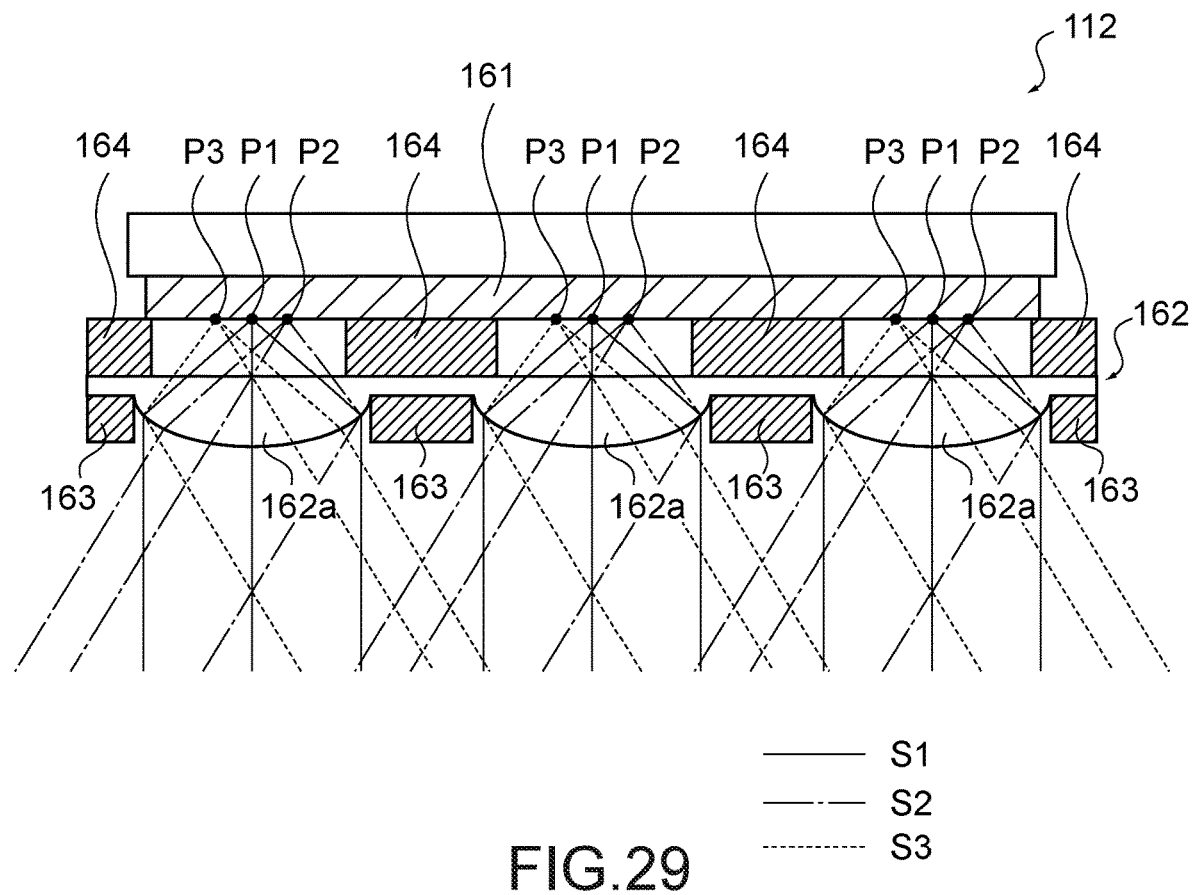
FIG. 29 A schematic diagram showing another configuration of the light receiving unit of the blood flow measurement apparatus.

Further, as shown in FIG. 29, the incident angle limiting unit 162 may include both light shields 163 and light shields 164. By providing both the light shields 163 and the light shields 164, it is possible to further reduce stray light incident from portions between the lenses 162a, to can more effectively prevent disturbance noise due to the Doppler beat, and to enhance the resistance to the position dependency of the blood flow rate.

Figure 30:
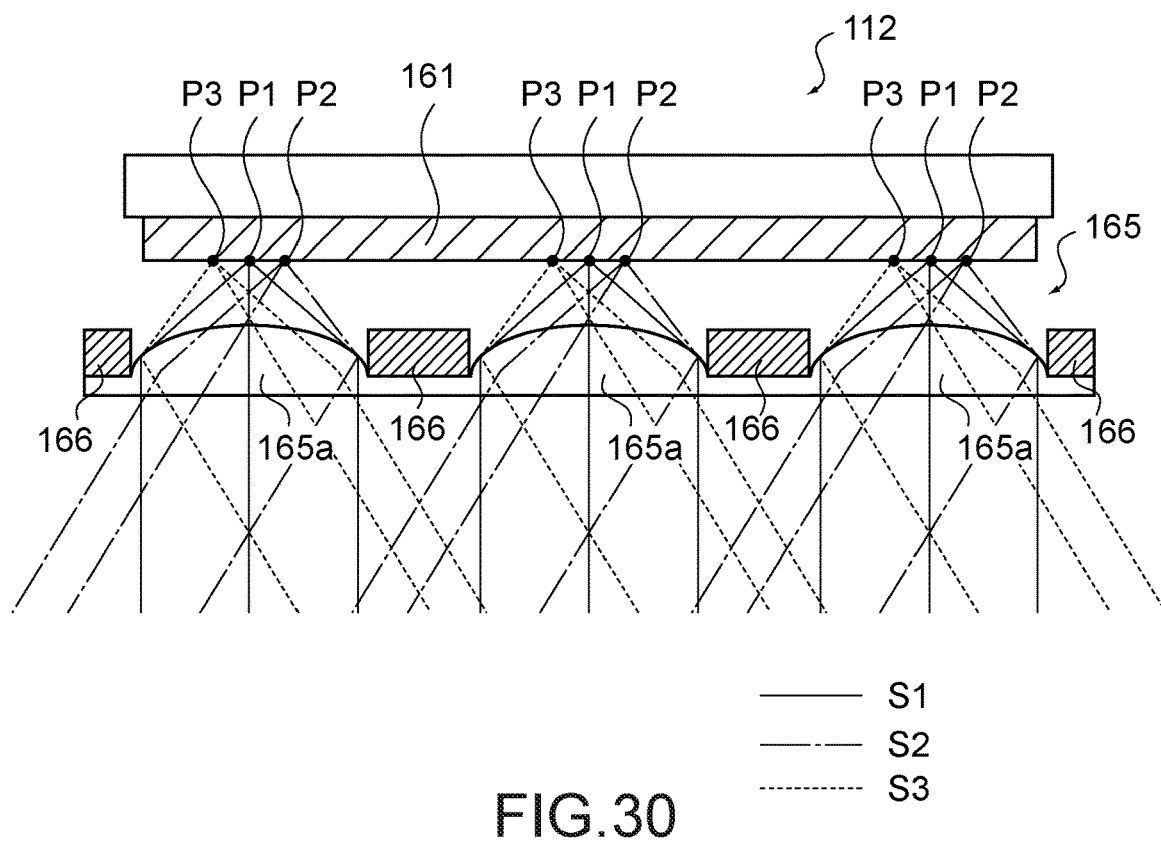
FIG. 30 A schematic diagram showing another configuration of the light receiving unit of the blood flow measurement apparatus.

Further, as shown in FIG. 30, the light receiving unit 112 may include a measurement light receiving element 161 and an incident angle limiting unit 165. The incident angle limiting unit 165 is a lens array in which lenses 165a convex toward the measurement light receiving element 161 are arranged. The incident angle limiting unit 165 includes light shields 166.

The light shields 166 are disposed between the lenses 165a between the incident angle limiting unit 165 and the measurement light receiving element 161 and shields scattered light that enters the portions between the lenses 165a.

Also with this configuration, it is possible to more effectively prevent disturbance noise due to a Doppler beat and to enhance the resistance to the position dependency of the blood flow rate. Further, it is possible to use the lens array as a cover for the measurement light receiving element 161, and to enhance the resistance to external light by providing the lens array with a characteristic of absorbing light other than the light source wavelength such as IR black.

Figure 31:
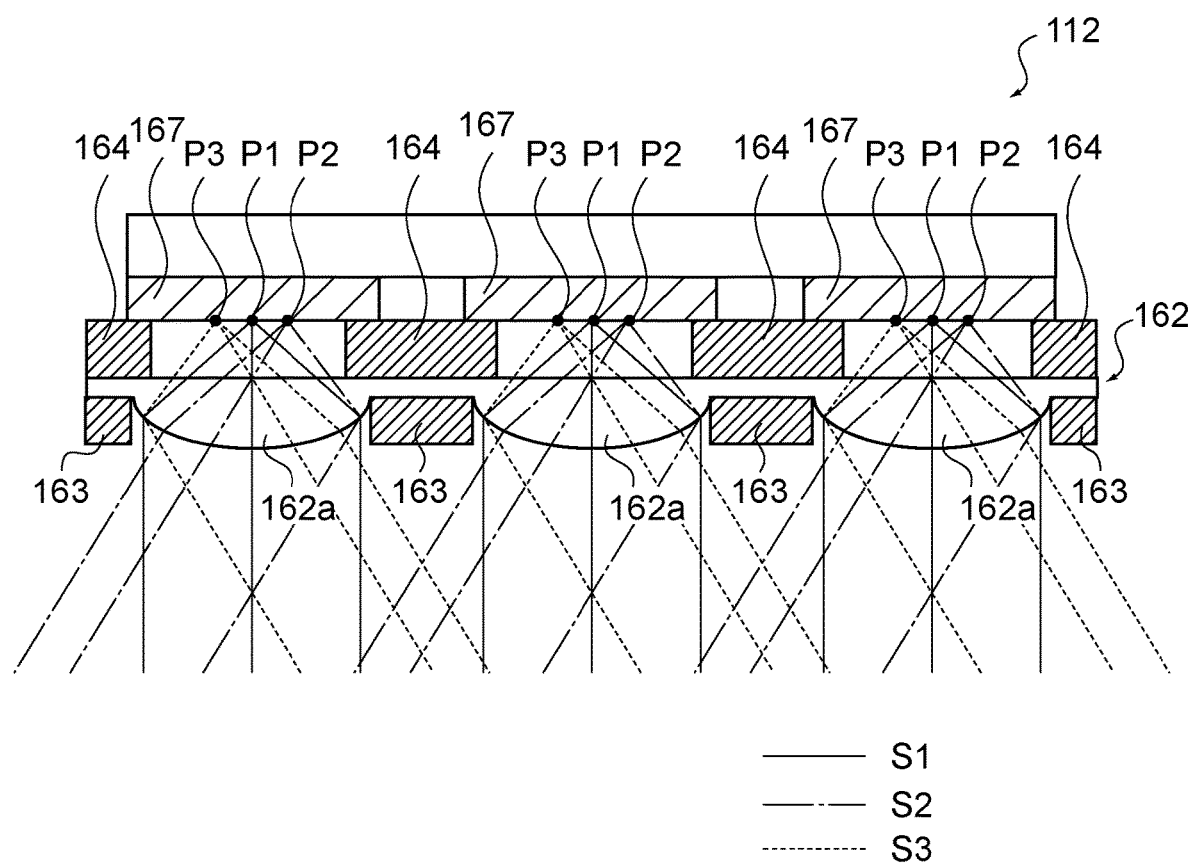
FIG. 31 A schematic diagram showing another configuration of the light receiving unit of the blood flow measurement apparatus.

Further, as shown in FIG. 31, the light receiving unit 112 may include a plurality of light receiving elements 167 and the incident angle limiting unit 162. The incident angle limiting unit 162 is configured such that the respective lenses 162a collect light to the respective light receiving elements 167. The incident angle limiting unit 162 includes light shields 163 and light shields 164.

With this configuration, it is possible to more effectively prevent disturbance noise caused by the Doppler beat, to observe the position dependency of the blood flow rate, and to achieve both resolution and coverage between the light receiving elements 167. It should be noted that a plurality of lenses 162a may be arranged for a single light receiving element 167. Further, either the light shields 163 or the light shields 164 may be provided or neither of them may be provided.

Figure 32:
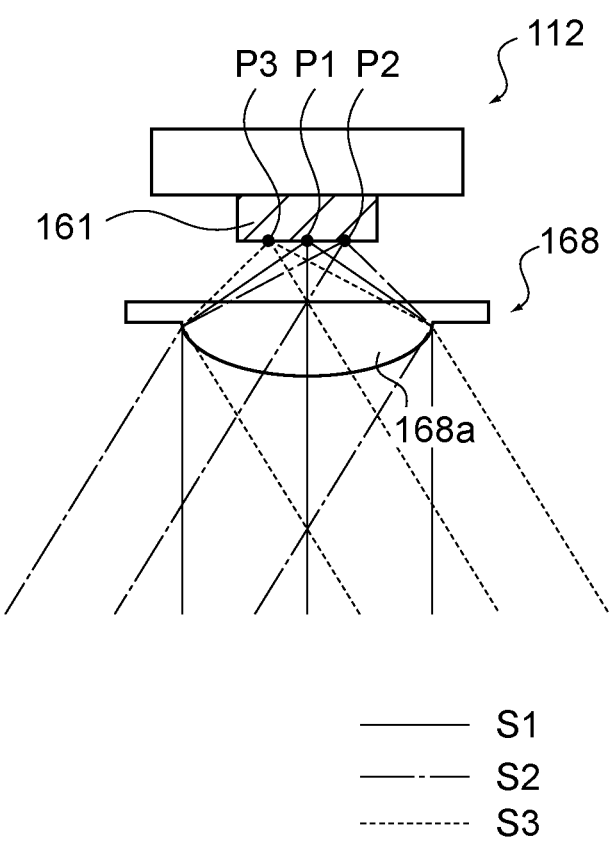
FIG. 32 A schematic diagram showing another configuration of the light receiving unit of the blood flow measurement apparatus.

Further, as shown in FIG. 32, the light receiving unit 112 may include a measurement light receiving element 161 and an incident angle limiting unit 168. The incident angle limiting unit 168 is constituted by a single lens 168a. Also with this configuration, the disturbance noise due to the relative velocity between the sensor head 110 and the living body 600 can be overcome.

Further, by reducing the area of the light receiving surface of the measurement light receiving element 161 and reducing the diameter of the light beam collected to a single point of the measurement light receiving element 161 (in FIG. 22, D), the disturbance noise due to the relative angular velocity between the sensor head 110 and the living body 600 can be overcome. In addition, this configuration can be realized at low costs.

Figure 33:
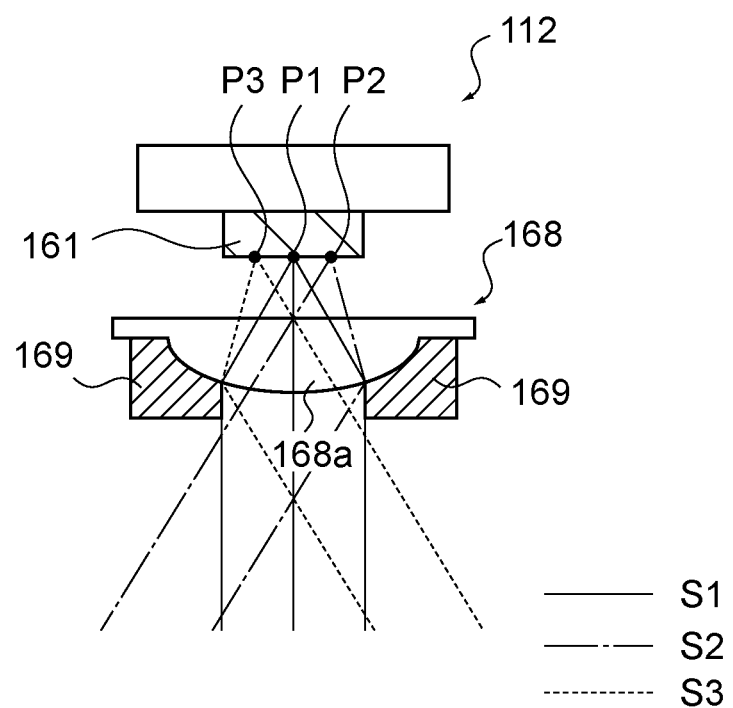
FIG. 33 A schematic diagram showing another configuration of the light receiving unit of the blood flow measurement apparatus.

Further, as shown in FIG. 33, the incident angle limiting unit 168 may include a light shield 169. The light shield 169 is provided around the lens 168a to limit the diameter of the light beam incident on the lens 168a, With this configuration, the relative velocity between the sensor head 110 and the living body 600 and the disturbance noise due to the relative angular velocity can also be overcome. In addition, this configuration can also be realized at low costs.

Figure 34:
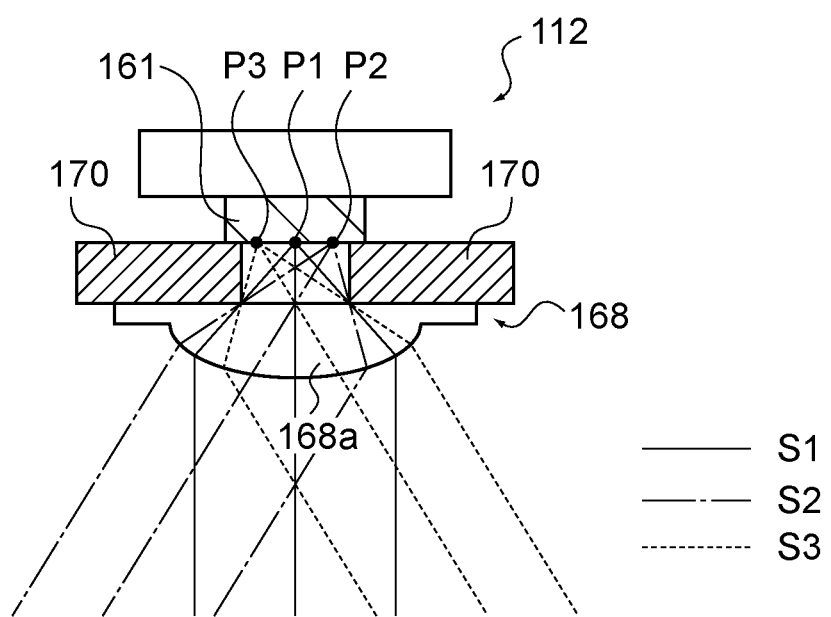
FIG. 34 A schematic diagram showing another configuration of the light receiving unit of the blood flow measurement apparatus.

Further, as shown in FIG. 34, the incident angle limiting unit 168 may include a light shield 170. The light shield 169 is provided around the lens 168a between the lens 168a and the measurement light receiving element 161 and limits the diameter of the light beam incident on the measurement light receiving element 161.

With this configuration, the relative velocity between the sensor head 110 and the living body 600 and the disturbance noise due to the relative angular velocity can also be overcome. In addition, this configuration can also be realized at low costs.

Figure 35:
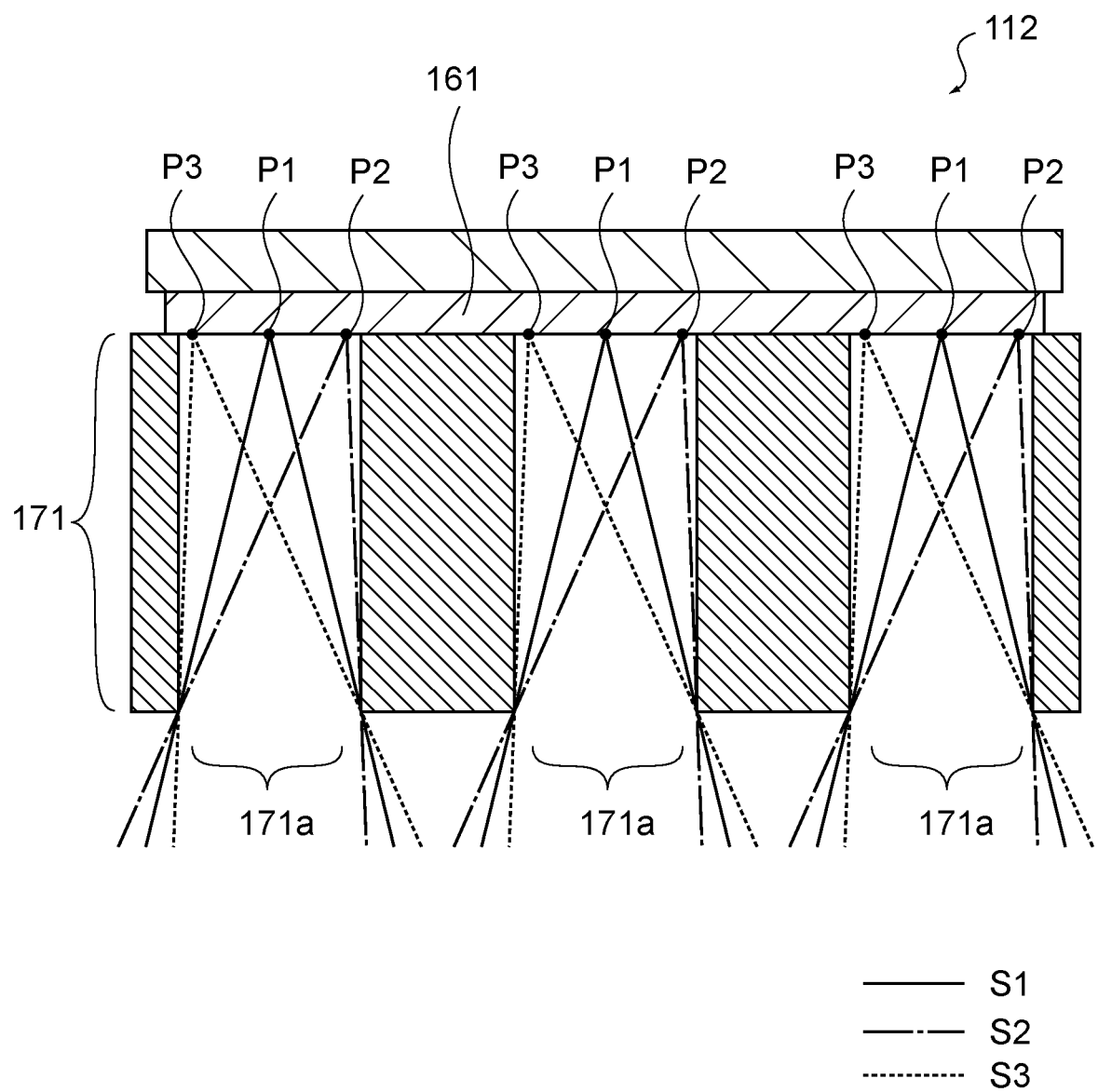
FIG. 35 A schematic diagram showing another configuration of the light receiving unit of the blood flow measurement apparatus.

Further, as shown in FIG. 35, the light receiving unit 112 may include a measurement light receiving element 161 and an incident angle limiting unit 171. The incident angle limiting unit 171 is a pin hole structure including a plurality of pin holes 171a made of a light-shielding material and extending in a direction perpendicular to the light receiving surface of the measurement light receiving element 161.

With this pin hole 171a, the scattered light S1 is incident on the point P1 on the measurement light receiving element 161, the scattered light S2 is incident on the point P2 on the measurement light receiving element 161, and the scattered light S3 is incident on the point P3 on the measurement light receiving element 161. That is, the incident angle limiting unit 171 limits the incident angle of the scattered light S incident on the single point of the measurement light receiving element 161 to be equal to or smaller than the predetermined angle. More specifically, when the predetermined angle is 10 degrees or less, β becomes 0.1 or less and satisfactory effects can be obtained.

Therefore, in accordance with a principle similar to that in a case where the incident angle limiting unit is a lens, it is possible to prevent the disturbance noise due the Doppler beat. Further, by guiding the scattered light from the plurality of pin holes 171a to the single measurement light receiving element 161, the utilization efficiency of light can be increased by the number of pin holes 171a as compared to a sensor head with a single pin hole despite the single measurement light receiving element. Accordingly, high-sensitivity can be realized at low costs.

On the other hand, the scattered light S that has not passed through the pin hole 171a becomes lost. Therefore, the utilization efficiency of light is better in a case where the incident angle limiting unit is a lens. However, there is an advantage that the problem of aberration and stray light due to the lens can be avoided.

[Hardware Configuration]

Figure 36:
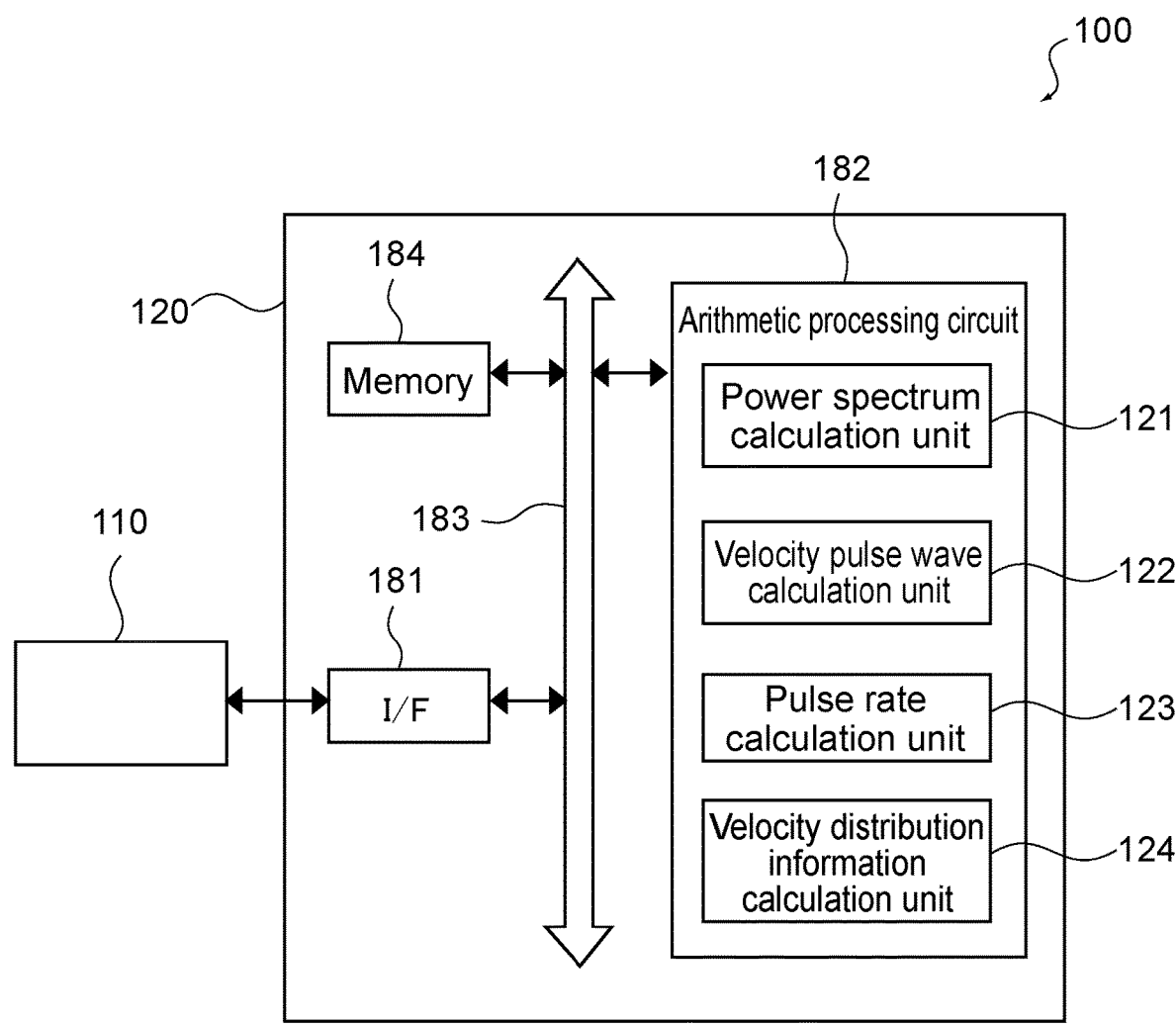
FIG. 36 A block diagram showing a hardware configuration of an information processing apparatus of the blood flow measurement apparatus.

A hardware configuration of the information processing apparatus 120 will be described. FIG. 36 is a schematic diagram showing the hardware configuration of the information processing apparatus 120. As shown in FIG. 1, the information processing apparatus 120 includes an interface (I/F) 181, arithmetic processing circuit 182, a bus 183, and a memory 184.

The I/F 181 provides a beat signal (see FIG. 10) obtained from the sensor head 110 to the bus 183. The arithmetic processing circuit 182 is a processor such as a central processing unit (CPU). The arithmetic processing circuit 182 obtains the beat signal via the bus 183 and executes various types of arithmetic processing while exchanging information with the memory 184.

The power spectrum calculation unit 121, the velocity pulse wave calculation unit 122, the pulse rate calculation unit 123, and the velocity distribution information calculation unit 124 having the above-mentioned functional configurations are realized by the cooperation of the arithmetic processing circuit 182 and the program.

It should be noted that some or all of the configurations of the information processing apparatus 120 may be implemented on a computer network. Further, some or all of the configurations of the information processing apparatus 120 may be realized by arithmetic circuits that perform particular processing such as a field-programmable gate array (FPGA) and an application specific integrated circuit (ASIC).

Second Embodiment

[Configuration of Blood Flow Measurement Apparatus According to Second Embodiment]

Figure 37:
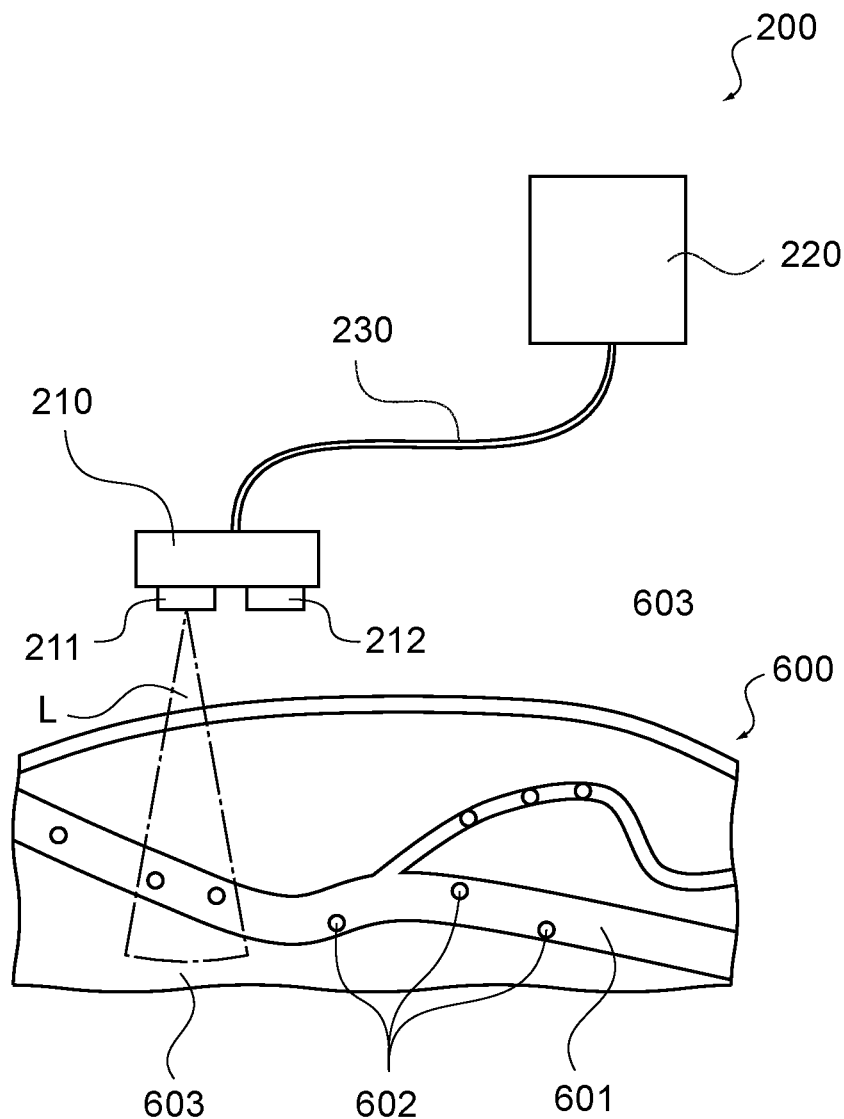
FIG. 37 A schematic diagram of a blood flow measurement apparatus according to a second embodiment of the present technology.
Figure 38:
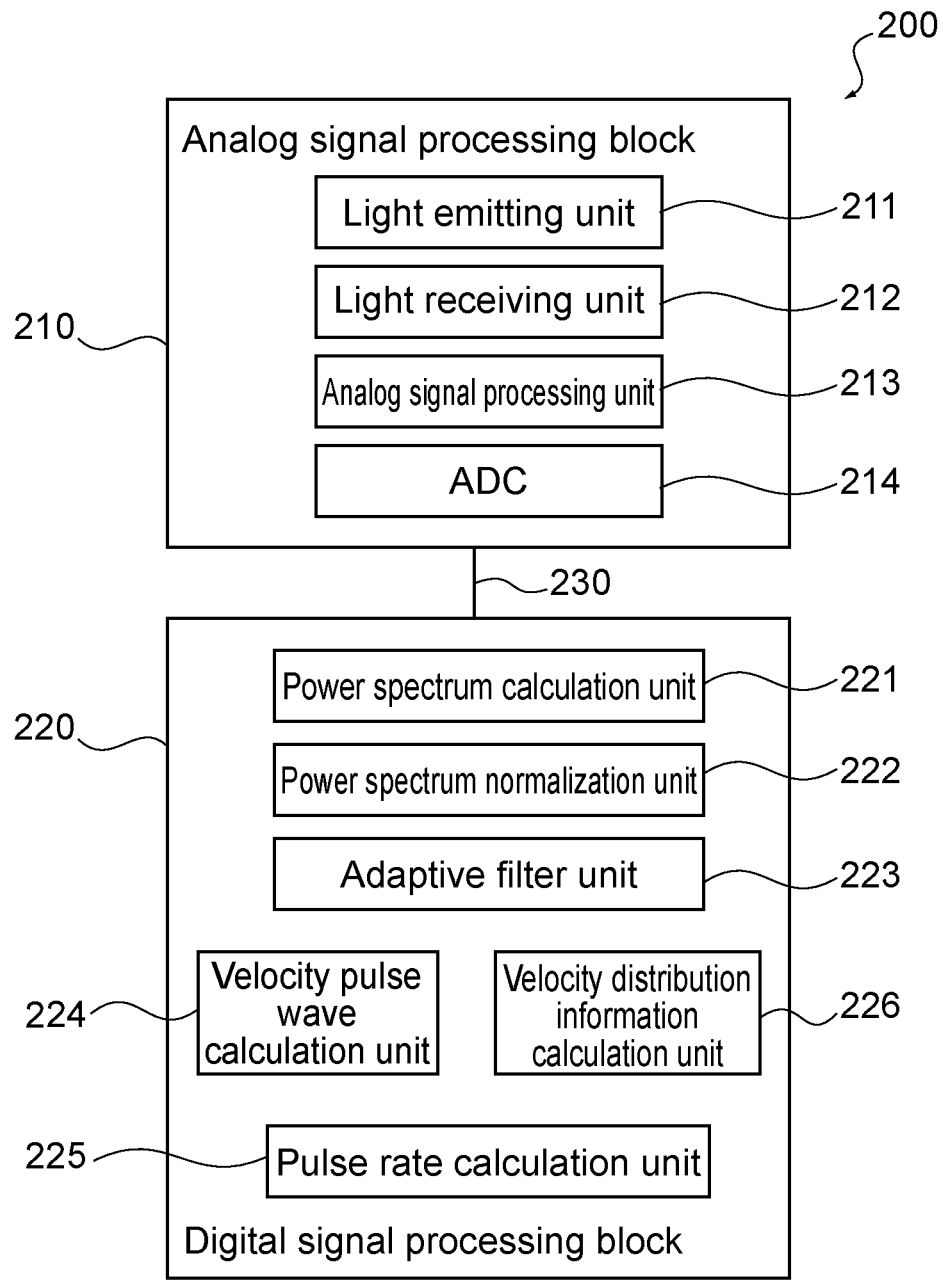
FIG. 38 A block diagram showing functions of the blood flow measurement apparatus.

A configuration of a blood flow measurement apparatus 200 according to a second embodiment of the present technology will be described. FIG. 37 is a schematic diagram of the blood flow measurement apparatus 200 according to the present embodiment. FIG. 38 is a block diagram showing functions of the blood flow measurement apparatus 200.

As shown in FIG. 37, the blood flow measurement apparatus 200 includes a sensor head 210 and an information processing apparatus 220. The sensor head 210 and the information processing apparatus 220 are connected through a signal line 230. The blood flow measurement apparatus 200 may be a wearable device.

The living body 600 that is the blood flow measurement target has red blood cells 602 flowing through a blood vessel 601, and a stationary tissue 603.

As shown in FIG. 37, the sensor head 210 is disposed close to or in close contact with the living body 600. As shown in FIGS. 37 and 38, the sensor head 210 includes a light emitting unit 211, a light receiving unit 212, an analog signal processing unit 213, and an ADC 214.

Figure 39:
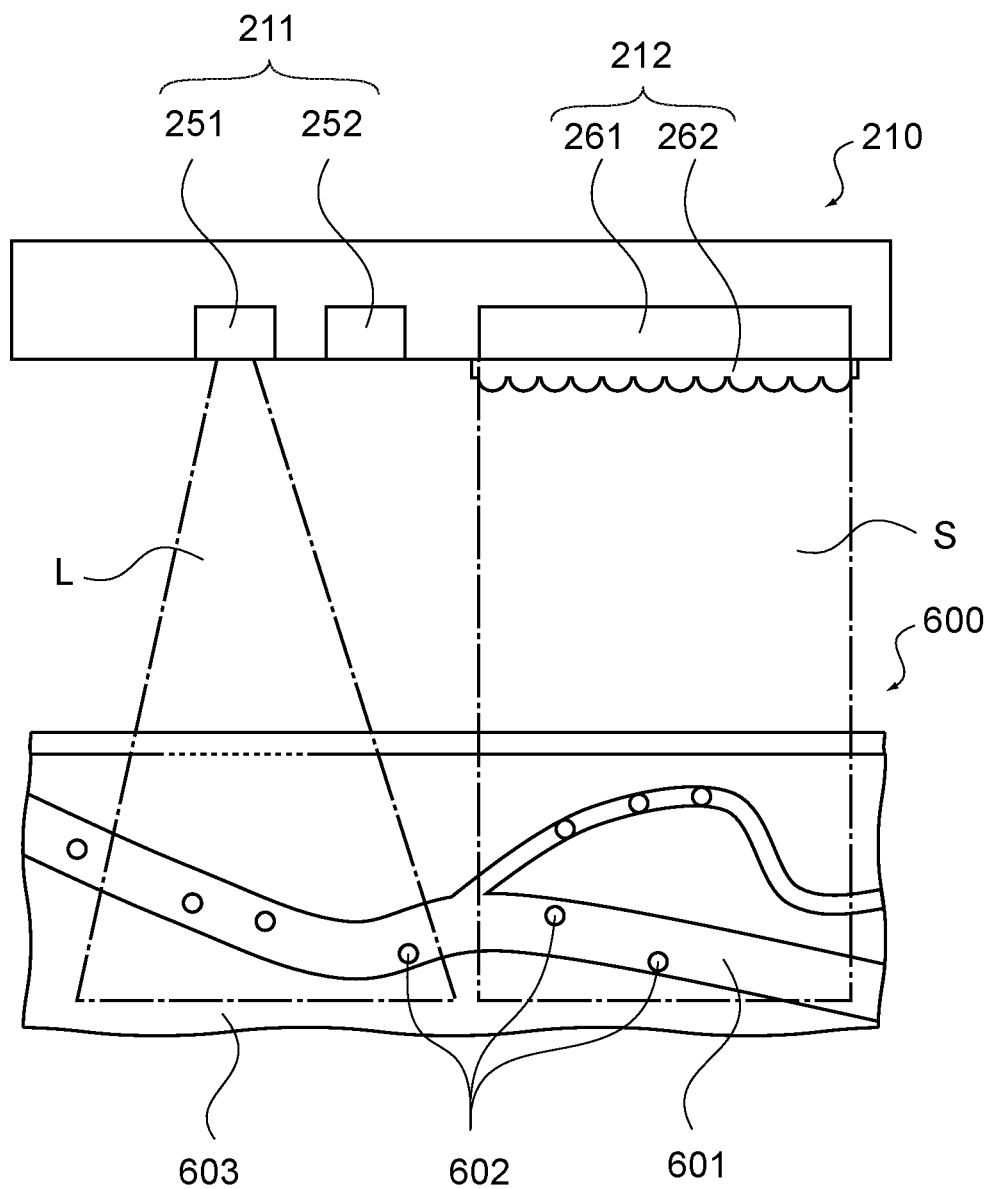
FIG. 39 A cross-sectional view of a light emitting unit and a light receiving unit of the blood flow measurement apparatus.
Figure 40:
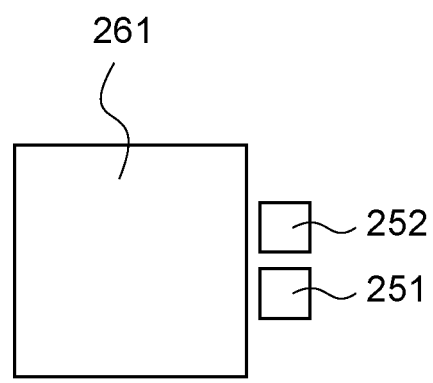
FIG. 40 A plan view of the light emitting unit and the light receiving unit of the blood flow measurement apparatus.

The light emitting unit 211 and the light receiving unit (sensor) 212 are mounted on the sensor head 210 and the relative position relative to the sensor head 210 is fixed. FIG. 39 is a cross-sectional view of the sensor head 210. FIG. 40 is a plan view of the sensor head 210 viewed from the living body 600 side.

The light emitting unit 211 alternately emits two types of laser light having different wavelength bands in a time division manner and irradiates the living body 600 with the laser light L.

As shown in FIGS. 39 and 40, the light emitting unit 211 may include a first laser light source 251 and a second laser light source 252. The first laser light source 251 and the second laser light source 252 have emission wavelengths different from each other. It should be noted that in FIG. 39, the first laser light source 251 should originally be located at the same position as the second laser light source 252, but it is shown, shift to the left because it would interfere with the comprehension of the drawing.

It should be noted that of the first laser light source 251 and the second laser light source 252 may be provided with the irradiation light control unit described in the first embodiment.

The light receiving unit 212 receives the laser light L obtained when the scattered light is scattered by the living body 600. The light receiving unit 212 converts the received scattered light into a signal.

The light receiving unit 212 includes a measurement light receiving element 261 and an incident angle limiting unit 262. The measurement light receiving element 261 and the incident angle limiting unit 262 can respectively have the same configuration (see FIG. 18) as the measurement light receiving element 161 and the incident angle limiting unit 162 described in the first embodiment.

Further, the incident angle limiting unit 262 may have another configuration (see FIGS. 27 to 35) of the first embodiment. In addition, the light receiving unit 212 may be configured to include only the measurement light receiving element 261 and not to include the incident angle limiting unit 262.

The measurement light receiving element 261 receives scattered light (hereinafter, referred to as first scattered light) emitted from the first laser light source 251 and scattered light (hereinafter, referred to as second scattered light) emitted from the second laser light source 252 for each predetermined time.

The analog signal processing unit 213 performs signal processing such as amplification on the signal output from the light receiving unit 212 and supplies it to the ADC 214.

The analog to digital converter (ADC) 214 converts the analog signal supplied from the analog signal processing unit 213 into a digital signal. The ADC 214 outputs the converted digital signal to the information processing apparatus 220 via the signal line 230 as a beat signal.

As shown in FIG. 38, the information processing apparatus 220 includes a power spectrum calculation unit 221, a power spectrum normalization unit 222, an adaptive filter unit 223, a velocity pulse wave calculation unit 224, a pulse rate calculation unit 225, and a velocity distribution information calculation unit 226.

The power spectrum calculation unit 221 performs arithmetic processing such as Fourier transform on the beat signal obtained from the ADC 214. Accordingly, the power spectrum calculation unit 221 calculates the power spectrum of the signal that may be changed to the frequency domain for each predetermined time. The predetermined time is, for example, 1/300 to 1/100 seconds.

The power spectrum calculation unit 221 separates the beat signal into a beat signal 2 generated from the first scattered light and a beat signal 1 generated from the second scattered light and calculates a power spectrum for each of them. The power spectrum based on the beat signal 1 is defined as a first power spectrum. The power spectrum based on the beat signal 2 is defined as a second power spectrum.

A power spectrum normalization unit 222 normalizes the first power spectrum and the second power spectrum. Light having different wavelengths has different Doppler shift frequencies generated at the same velocity. Therefore, the power spectrum normalization unit 222 normalizes the frequency axis of the spectrogram such that those having the same velocity are made to correspond to each other.

The adaptive filter unit 223 inputs the normalized first power spectrum and second power spectrum to an adaptive filter. Accordingly, the Doppler beat (see FIGS. 13 and 14) caused by the stationary tissue 603 is removed.

The velocity pulse wave calculation unit 224 calculates a velocity pulse wave on the basis of a time-series change of the power spectrum of the beat signal output from the adaptive filter unit 223. The pulse rate calculation unit 225 calculates a pulse rate on the basis of the velocity pulse wave calculated by the velocity pulse wave calculation unit 224.

The velocity distribution information calculation unit 226 calculates velocity distribution information by performing an operation such as integral processing on the power spectrum of the signal output from the adaptive filter unit 223.

The power spectrum calculation unit 221, the velocity pulse wave calculation unit 224, the pulse rate calculation unit 225, and the velocity distribution information calculation unit 226 function as a blood flow-related information calculation unit that calculates blood flow-related information. The blood flow-related information calculation unit may have another configuration capable of calculating the blood flow-related information.

Further, the power spectrum normalization unit 222 and the adaptive filter unit 223 function as a noise cancellation unit that cancels noise caused by the relative motion between the sensor head 210 and the living body 600 from the blood flow-related information. The noise cancellation unit may have another configuration capable of cancelling the noise.

The blood flow measurement apparatus 200 has the above-mentioned configuration. It should be noted that sensor head 210 functions as an analog signal processing block of the blood flow measurement apparatus 200 and the information processing apparatus 220 functions as a digital signal processing block.

The configuration of the blood flow measurement apparatus 200 is not limited thereto. Digital signal processing may be performed at the sensor head 210 and analog signal processing may be performed at the information processing apparatus 220.

[Operation of Blood Flow Measurement Apparatus According to Second Embodiment]

An operation of the blood flow measurement apparatus 200 will be described.

As shown in FIG. 39, the first laser light source 251 and the second laser light source 252 of the light emitting unit 211 are alternately irradiated with the laser light L to the living body 600.

First scattered light obtained when laser light emitted from the first laser light source 251 is scattered and second scattered light obtained when laser light emitted from the second laser light source 252 is scattered are respectively received by the measurement light receiving element 261.

Here, when the wavelengths of the laser light are different, the depth penetration of the laser light in the living body 600 is different, the depth of the observation area is different, and the patterns of multiple scattering thereafter are different. Therefore, when the wavelengths of the irradiated laser light are switched, differences is caused in the observation target red blood cells 602 and the observation target stationary tissue 603, and the detected beat signals are also mixed at different ratios. Therefore, in the first beat signal generated by receiving the first scattered light and the second beat signal generated by receiving the second scattered light, signals from a plurality of targets are mixed at different ratios. This difference in mixing ratio can be utilized to effectively cancel noise components.

In the blood flow measurement apparatus according to the first embodiment, the relative velocity and the relative angular velocity noise can be effectively reduced, but the beat signal of the scattered light of the stationary tissue may still remain. The mixing ratio of the beat signal between the scattered light of such stationary tissue and the beat signal by the red blood cells is also different between the first beat signal and the second beat signal. Thus, the ratio of the components derived from the beat signal due to the stationary tissue 603 to the components derived from the beat signal due to the red blood cells 602 differs between the first power spectrum generated from the first beat signal and the second power spectrum generated from the second beat signal. Therefore, the relative velocity components between the sensor head 210 and the living body 600 can be removed by normalizing both the power spectra by the power spectrum normalization unit 222 and then performing the processing by the adaptive filter unit 223.

In the blood flow measurement apparatus 200, the disturbance noise can be prevented from being generated in the following manner.

[Variations of Light Receiving Unit]

Figure 41:
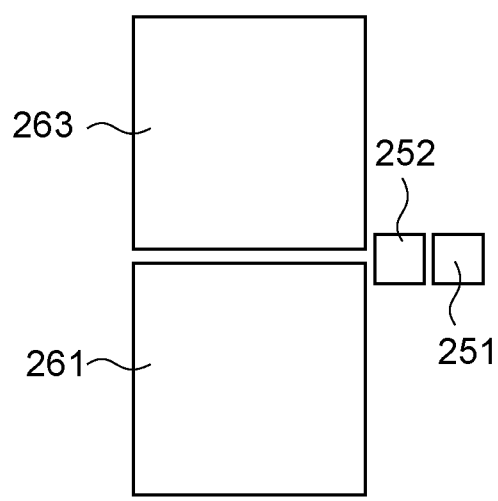
FIG. 41 A schematic diagram showing another configuration of the light receiving unit of the blood flow measurement apparatus.

The light receiving unit 212 is not limited to the above-mentioned configuration. FIG. 41 is a schematic diagram showing a light receiving unit 212 having another configuration.

As shown in the figure, the light receiving unit 212 includes another measurement light receiving element 263 in addition to the measurement light receiving element 261. The measurement light receiving element 261 and the measurement light receiving element 263 are light receiving elements for blood flow measurement as described above. The sensor head 210 outputs the difference between the beat signals detected by the two pixels as a beat signal. By taking such a configuration, it is possible to effectively remove noise components that vary in the same manner in two pixels, such as external light noise.

Although a technique of using such a difference signal has been known for a long time, it is possible to use a similar difference signal by devising the arrangement of pixels and the arrangement of light sources as shown in FIG. 41 in the blood flow measurement apparatus 200.

[Hardware Configuration]

Figure 42:
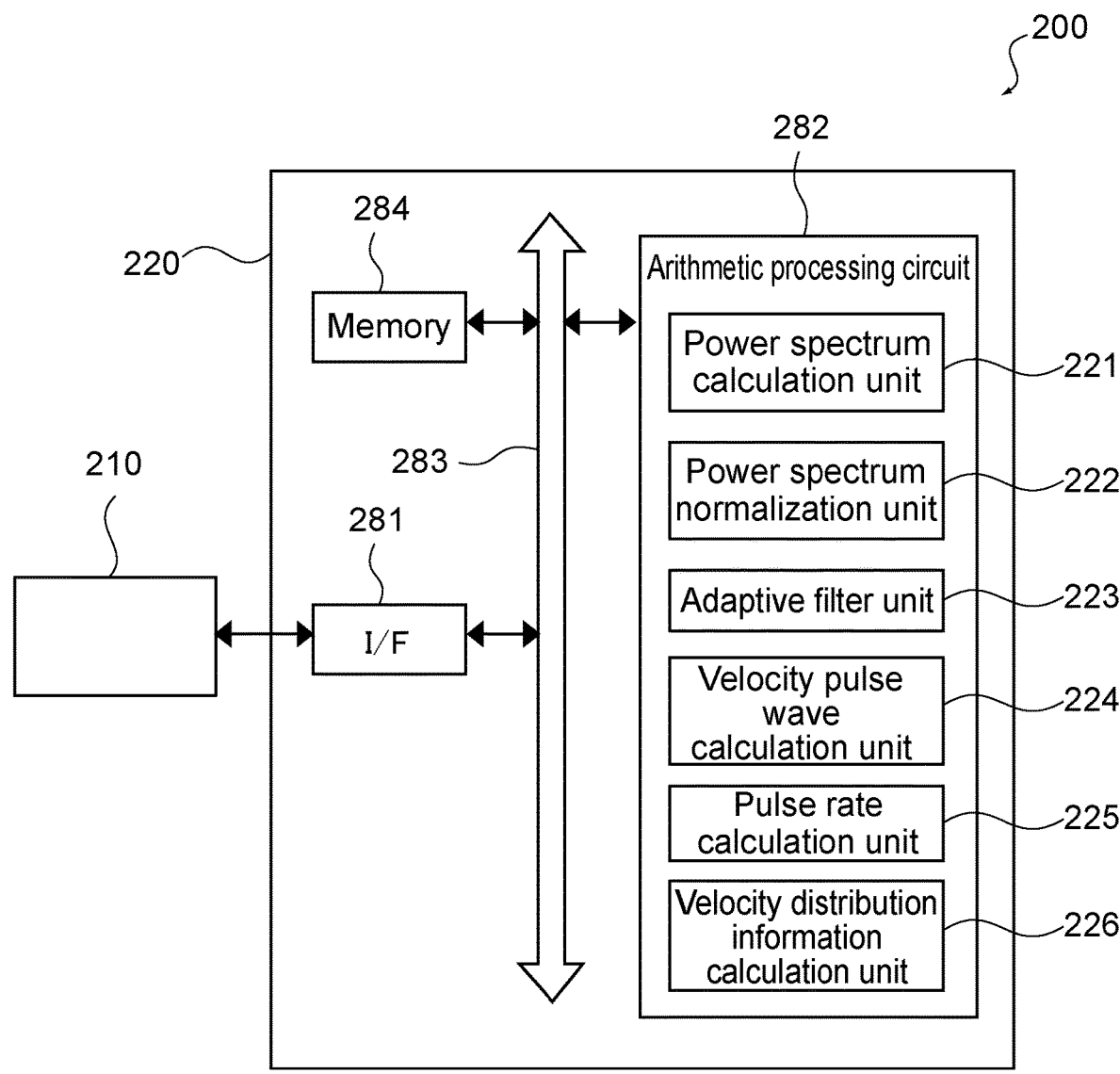
FIG. 42 A block diagram showing a hardware configuration of an information processing apparatus of the blood flow measurement apparatus.

A hardware configuration of the information processing apparatus 220 will be described. FIG. 42 is a schematic diagram showing a hardware configuration of the information processing apparatus 220. As shown in FIG. 2, the information processing apparatus 220 includes an interface (I/F) 281, arithmetic processing circuit 282, a bus 283, and a memory 284.

The I/F 281 provides a beat signal obtained from the sensor head 210 (see FIG. 10) to the bus 283. The first laser light source 251 and the second laser light source 252 emit light alternately. Therefore, for the beat signal obtained from the sensor head 210, the beat signal 1 and the beat signal 2 are alternately supplied in time division. The arithmetic processing circuit 282 is a processor such as a central processing unit (CPU). A spatial speckle signal is obtained via the bus 283 and various types of arithmetic processing are performed while exchanging information with the memory 284.

The power spectrum calculation unit 221, the power spectrum normalization unit 222, the adaptive filter unit 223, the velocity pulse wave calculation unit 224, the pulse rate calculation unit 225, and the velocity distribution information calculation unit 226 having the above-mentioned functional configurations are realized by the cooperation of the arithmetic processing circuit 282 and the program.

It should be noted that some or all of the configurations of the information processing apparatus 220 may be realized on a computer network.

Third Embodiment

[Configuration of Blood Flow Measurement Apparatus According to Third Embodiment]

Figure 43:
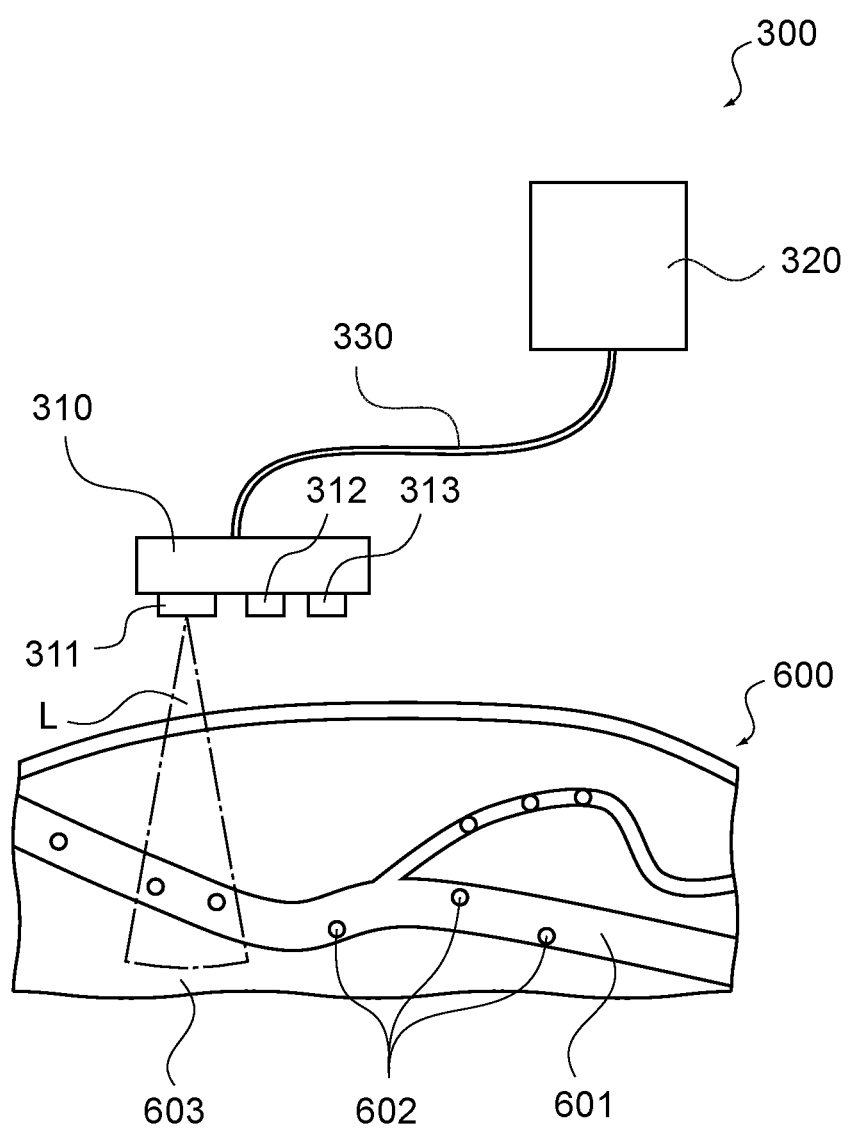
FIG. 43 A schematic diagram of a blood flow measurement apparatus according to a third embodiment of the present technology.
Figure 44:
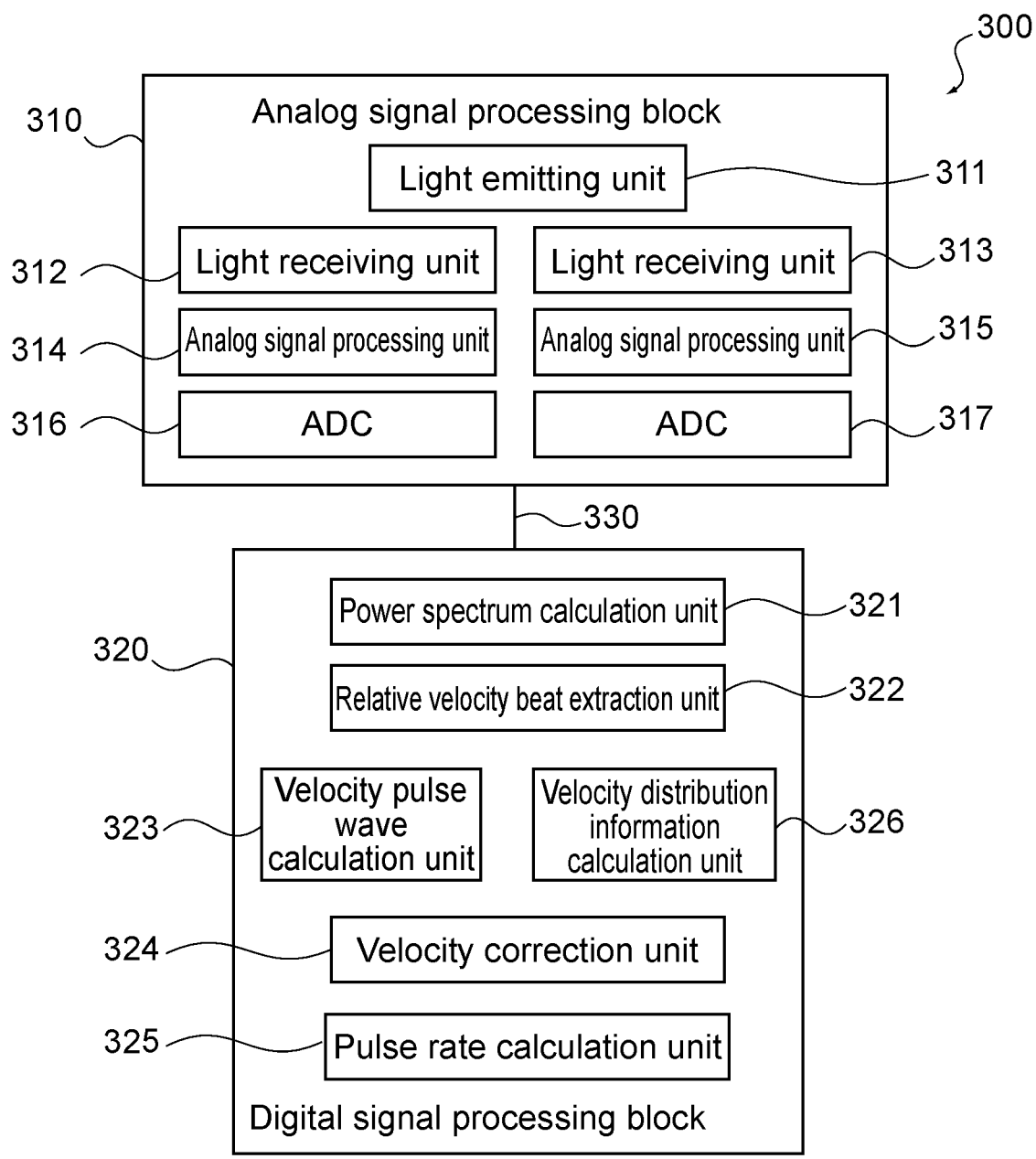
FIG. 44 A block diagram showing functions of the blood flow measurement apparatus.

A configuration of a blood flow measurement apparatus 300 according to a third embodiment of the present technology will be described. FIG. 43 is a schematic diagram of the blood flow measurement apparatus 300 according to the present embodiment. FIG. 44 is a block diagram showing functions of the blood flow measurement apparatus 300.

As shown in FIG. 43, the blood flow measurement apparatus 300 includes a sensor head 310 and an information processing apparatus 320. The sensor head 310 and the information processing apparatus 320 are connected through a signal line 330. The blood flow measurement apparatus 300 may be a wearable device.

The living body 600 that is the blood flow measurement target has red blood cells 602 flowing through a blood vessel 601, and a stationary tissue 603.

As shown in FIG. 43, the sensor head 310 is disposed close to or in close contact with the living body 600. As shown in FIGS. 43 and 44, the sensor head 310 includes a light emitting unit 311, a first light receiving unit 312, a second light receiving unit 313, a first analog signal processing unit 314, a second analog signal processing unit 315, a first ADC 316, and a second ADC 317.

Figure 45:
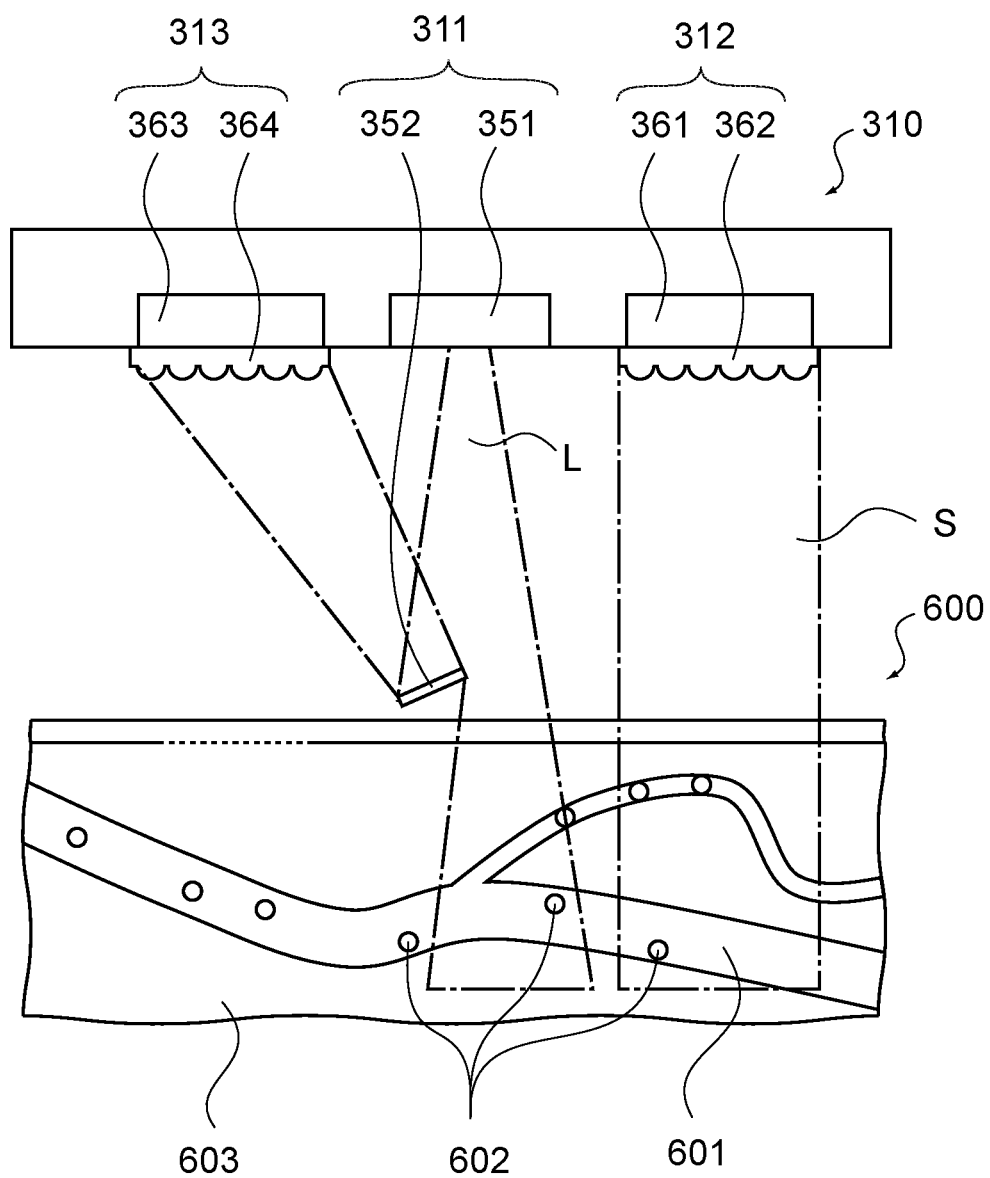
FIG. 45 A cross-sectional view of a light emitting unit and a light receiving unit of the blood flow measurement apparatus.
Figure 46:
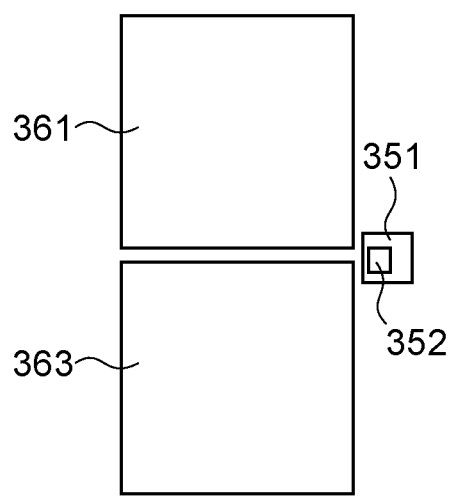
FIG. 46 A plan view of the light emitting unit and the light receiving unit of the blood flow measurement apparatus.

The light emitting unit 311, the first light receiving unit (sensor) 312, and the second light receiving unit 313 are mounted on the sensor head 310, and the relative position relative to the sensor head 310 is fixed. FIG. 45 is a cross-sectional view of a sensor head 310. FIG. 46 is a plan view of the sensor head 310 viewed from the living body 600 side.

The light emitting unit 311 irradiates the living body 600 and the second light receiving unit 313 with the laser light L. As shown in FIG. 45, the light emitting unit 311 may include a laser light source 351 and a reflector 352.

The reflector 352 is provided between the laser light source 351 and the living body 600 and reflects part of the laser light L emitted from the laser light source 351 toward the second light receiving unit 313. The reflector 352 may be, for example, a micro-mirror mounted by a Micro Electro Mechanical Systems (MEMS) technology.

It should be noted that the laser light source 351 may be provided with the irradiation light control unit described in the first embodiment.

The first light receiving unit 312 receives receives scattered light obtained when the laser light L is reflected by the living body 600, and converts the received scattered light into a signal. The first light receiving unit 312 includes a measurement light receiving element 361 and an incident angle limiting unit 362.

The measurement light receiving element 361 and the incident angle limiting unit 362 can respectively have the same configurations (see FIG. 18) as the measurement light receiving element 161 and the incident angle limiting unit 162 described in the first embodiment. Further, the incident angle limiting unit 362 may have another configuration of the first embodiment (see FIGS. 27 to 35).

The second light receiving unit 313 receives the laser light L reflected by the reflector 352 and scattered light obtained when the laser light L is scattered by the living body 600. The second light receiving unit 313 converts the received scattered light into a signal. The second light receiving unit 313 includes a reflected light receiving element 363 and an incident angle limiting unit 364.

The reflected light receiving element 363 can have the same configuration as the measurement light receiving element 361. The incident angle limiting unit 364 can have the same configuration as the incident angle limiting unit 362.

Further, the first light receiving unit 312 and the second light receiving unit 313 do not need to be provided with the incident angle limiting unit 362 and the incident angle limiting unit 364.

The first analog signal processing unit 314 performs signal processing such as amplification on the signal output from the first light receiving unit 312 and supplies it to the first ADC 316.

The second analog signal processing unit 315 performs signal processing such as amplification on the signal output from the second light receiving unit 313 and supplies it to the second ADO 317.

The first analog to digital converter (ADC) 316 converts the analog signal supplied from the first analog signal processing unit 314 into a digital signal.

The first ADC 316 outputs the converted digital signal to the information processing apparatus 320 via the signal line 330.

The second ADC 317 converts the analog signal supplied from the second analog signal processing unit 315 into a digital signal. The second ADC 317 outputs the converted digital signal to the information processing apparatus 320 via the signal line 330.

As shown in FIG. 44, the information processing apparatus 320 includes a power spectrum calculation unit 321, a relative velocity beat extraction unit 322, a velocity pulse wave calculation unit 323, a velocity correction unit 324, a pulse rate calculation unit 325, and a velocity distribution information calculation unit 326.

The power spectrum calculation unit 321 performs arithmetic processing such as Fourier transform on a beat signal obtained from the first ADC 316 and the second ADC 317. Accordingly, the power spectrum calculation unit 321 calculates the power spectrum of the signal that may be changed to the frequency domain for each predetermined time. The predetermined time is, for example, 1/100 seconds.

The power spectrum calculation unit 321 calculates a power spectrum for each of a beat signal 1 generated from the scattered light received by the measurement light receiving element 361 and a beat signal 2 generated from the laser beam and the scattered light received by the reflected light receiving element 363. The power spectrum based on the beat signal 1 is defined as a first power spectrum. The power spectrum based on the beat signal 2 is defined as a second power spectrum.

The relative velocity beat extraction unit 322 extracts a Doppler shift component due to the relative velocity between the sensor head 310 and the living body 600 from the first power spectrum and the second power spectrum. An adaptive filter technique can be used for this extraction. The second power spectrum includes frequency components of the beat signal due to the relative velocity v, which are substantially removed from the first power spectrum. Therefore, the second power spectrum often has a large crest in the high frequency part of the power spectrum. This component is hardly included in the first power spectrum. Therefore, this component can be extracted on a basis of a difference between both. The extracted frequency component has a peak at a frequency position proportional to the relative velocity v. Therefore, the extracted frequency component is informative about the relative velocity v.

The velocity pulse wave calculation unit 323 calculates a velocity pulse wave on the basis of a time-series change of the power spectrum of the beat signal output from the power spectrum calculation unit 321.

The velocity correction unit 324 corrects the velocity distribution calculated on the basis of the first power spectrum using the Doppler shift component extracted by the relative velocity beat extraction unit 322. An adaptive filter method can be used for this correction.

The pulse rate calculation unit 325 calculates a pulse rate on the basis of the velocity pulse wave calculated by the velocity pulse wave calculation unit 323 and corrected by the velocity correction unit 324.

The velocity distribution information calculation unit 326 calculates velocity distribution information by performing an operation such as integral processing on the power spectrum of the beat signal output from the relative velocity beat extraction unit 322.

The power spectrum calculation unit 321, the velocity pulse wave calculation unit 323, the pulse rate calculation unit 325, and the velocity distribution information calculation unit 326 function as a blood flow-related information calculation unit that calculates blood flow-related information. The blood flow-related information calculation unit may have another configuration capable of calculating the blood flow-related information.

Further, the relative velocity beat extraction unit 322 and the velocity correction unit 324 function as a noise cancellation unit that cancels noise caused by the relative motion between the sensor head 310 and the living body 600 from the blood flow-related data. The noise cancellation unit may have another configuration capable of cancelling the noise.

The blood flow measurement apparatus 300 has the above-mentioned configuration. It should be noted that sensor head 310 functions as an analog signal processing block of the blood flow measurement apparatus 300 and the information processing apparatus 220 functions as a digital signal processing block.

The configuration of the blood flow measurement apparatus 300 is not limited thereto. Digital signal processing may be performed at the sensor head 310 and analog signal processing may be performed at the information processing apparatus 320. Further, the second light receiving unit 313, the second analog signal processing unit 315, and the second ADC 317 are not essential. Noise may be cancelled in signal processing similar to that of the blood flow measurement apparatus according to the second embodiment by placing the reflector 352 so as to be able to reflect the laser light L toward the first light receiving unit 312 and then controlling the reflector 352 to alternately take a state to reflect the laser light L toward the first light receiving unit 312 and a state in which the laser light L does not reach the first light receiving unit 312. The control on the reflector 352 described above can be realized by constituting the reflector 352 by an MEMS mirror and then changing the angle of reflection by a drive mechanism for the MEMS, for example.

[Operation of Blood Flow Measurement Apparatus According to Third Embodiment]

An operation of the blood flow measurement apparatus 300 will be described.

As shown in FIG. 45, the living body 600 is irradiated with the laser light L from the laser light source 351 of the light emitting unit 311. The scattered light S obtained when the laser light L is reflected by the living body is received by the measurement light receiving element 361.

Further, part of the laser light L is reflected by the reflector 352 and is received by the reflected light receiving element 363 without entering the living body 600.

Here, when the relative velocity is caused between the sensor head 310 and the living body 600, a beat is caused between the frequency $f_0$ of the laser light L incident on the reflected light receiving element 363 and the frequency $f+\Delta f$ of the scattered light modulated with the relative velocity, which is incident on the measurement light receiving element 361. Where $\Delta f$ is approximately $2\alpha v \cos \theta$.

The relative velocity beat extraction unit 322 extracts a Doppler shift $\Delta f$ component due to the relative velocity between the sensor head 310 and the living body 600 from the first power spectrum based on the scattered light and the second power spectrum based on the laser light. The center of gravity of the obtained $\Delta f$ component represents $2\alpha v \cos \theta$. The velocity correction unit 324 removes components in the vicinity of this $2\alpha v \cos \theta$ from the velocity information.

In the blood flow measurement apparatus 300, the disturbance noise can be prevented from being generated in the following manner.

[Hardware Configuration]

Figure 47:
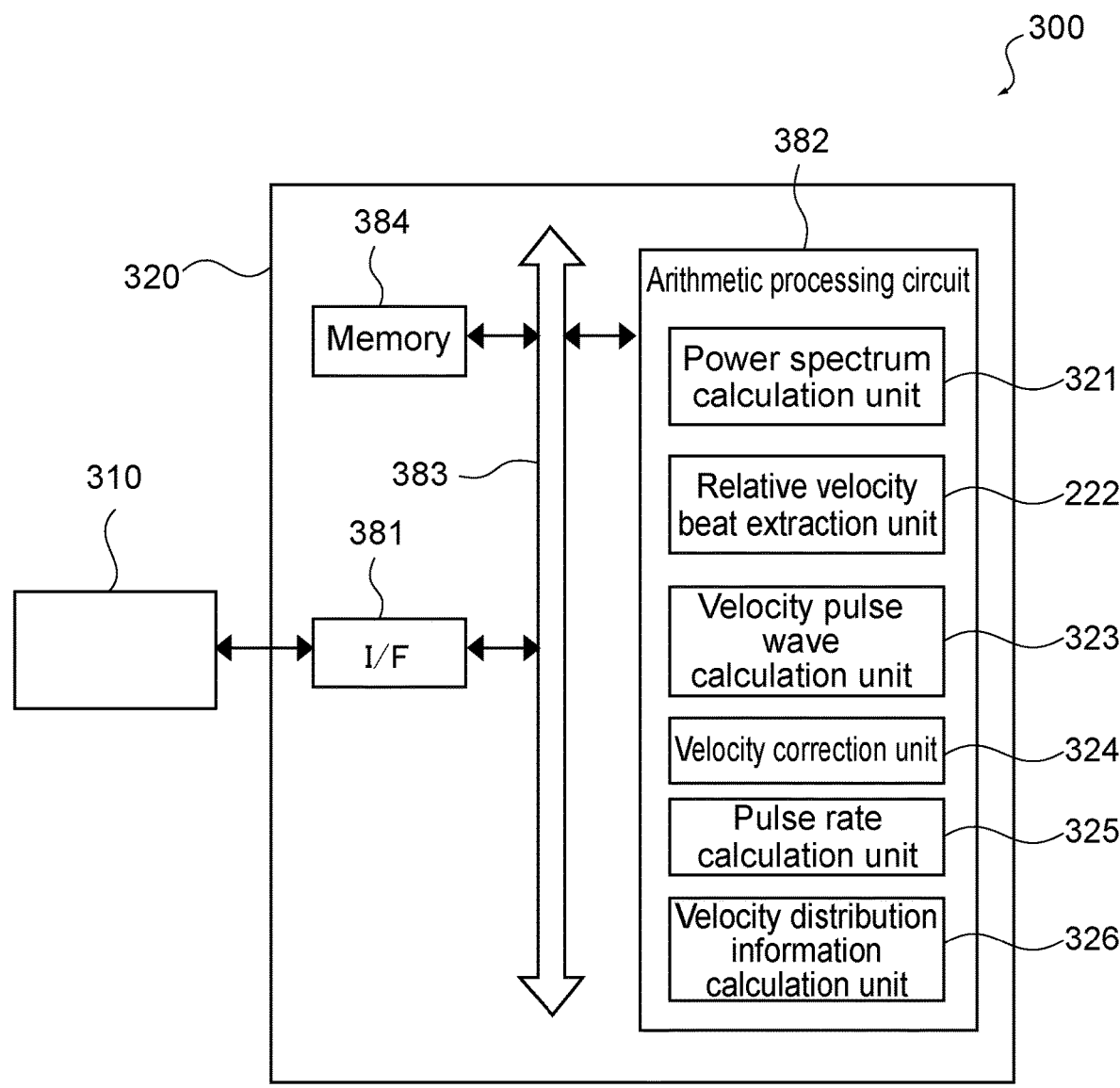
FIG. 47 A block diagram showing a hardware configuration of an information processing apparatus of the blood flow measurement apparatus.

A hardware configuration of the information processing apparatus 320 will be described. FIG. 47 is a schematic diagram showing a hardware configuration of the information processing apparatus 320. As shown in the figure, the information processing apparatus 320 includes an interface (I/F) 381, an arithmetic processing circuit 382, a bus 383, and a memory 384.

The I/F 381 provides a beat signal obtained from the sensor head 310 (see FIG. 10) to the bus 383. The arithmetic processing circuit 382 is a processor such as a central processing unit (CPU). The beat signal is obtained via the bus 383 and various arithmetic processing is executed while exchanging information with the memory 384.

The power spectrum calculation unit 321, the relative velocity beat extraction unit 322, the velocity pulse wave calculation unit 323, the velocity correction unit 324, the pulse rate calculation unit 325, and the velocity distribution information calculation unit 326 having the above-mentioned functional configurations are realized by the cooperation of the arithmetic processing circuit 382 and the program.

It should be noted that some or all of the configurations of the information processing apparatus 320 may be realized on a computer network.

Fourth Embodiment

[Configuration of Blood Flow Measurement Apparatus According to Fourth Embodiment]

Figure 48:
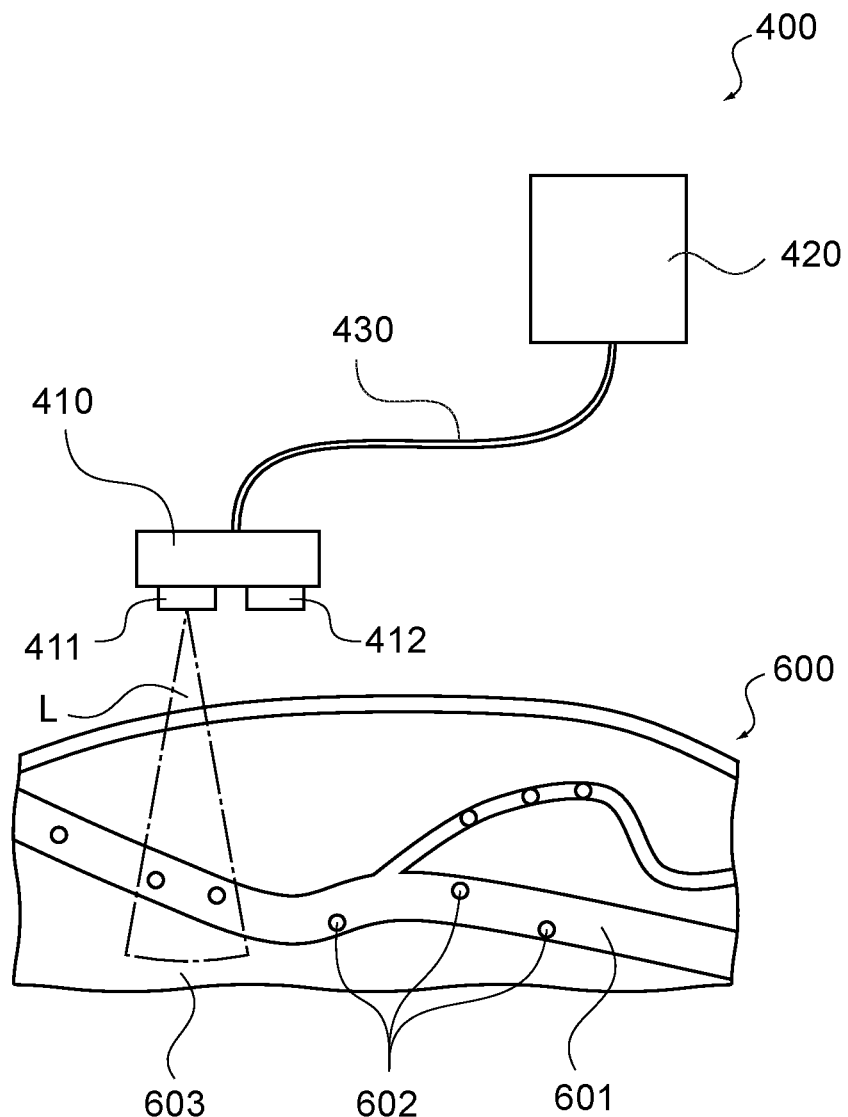
FIG. 48 A schematic diagram of a blood flow measurement apparatus according to a fourth embodiment of the present technology.
Figure 49:
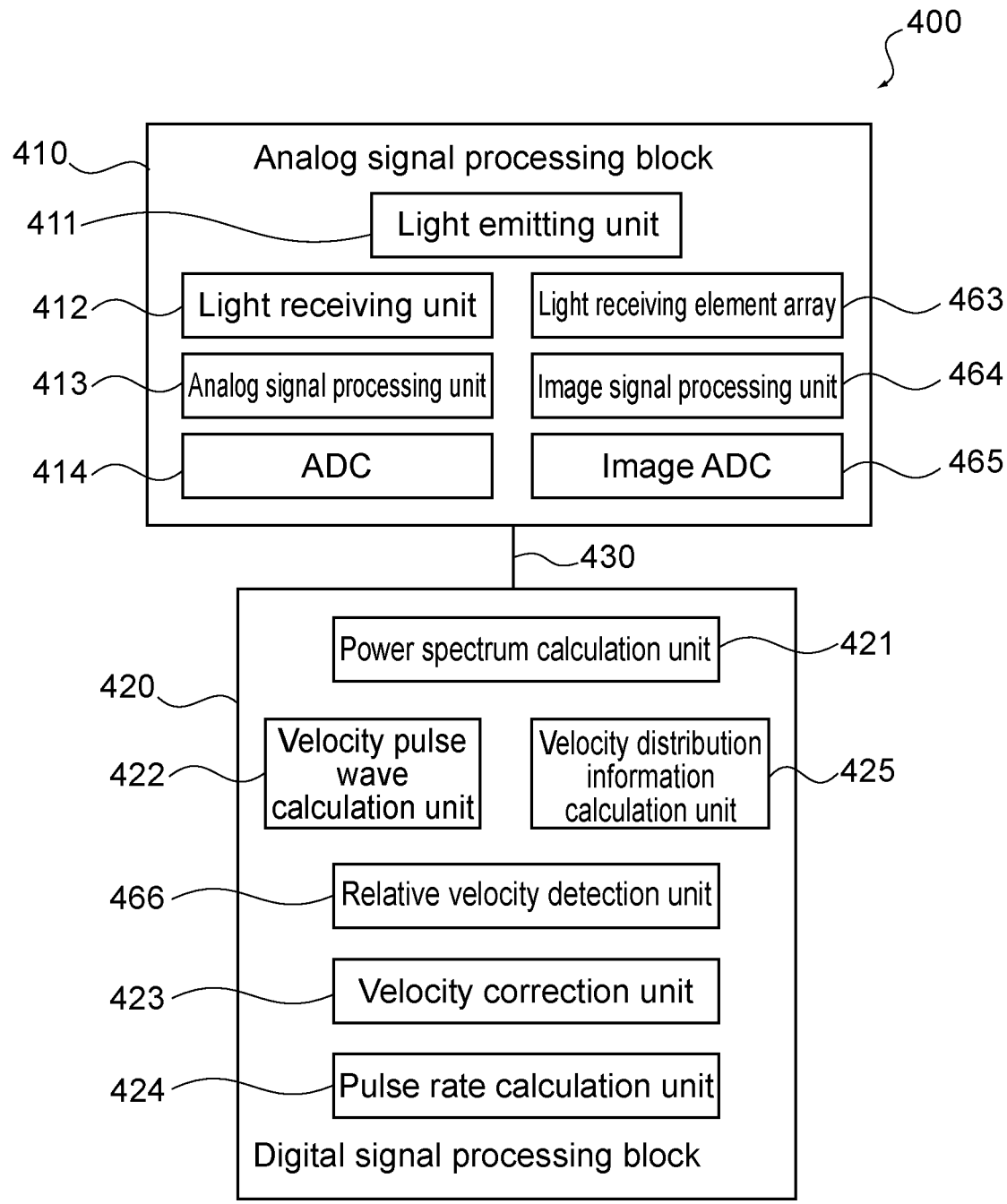
FIG. 49 A block diagram showing functions of the blood flow measurement apparatus.

A configuration of a blood flow measurement apparatus 400 according to a fourth embodiment of the present technology will be described. FIG. 48 is a schematic diagram of the blood flow measurement apparatus 400 according to the present embodiment. FIG. 49 is a block diagram showing functions of the blood flow measurement apparatus 400.

As shown in FIG. 48, the blood flow measurement apparatus 400 includes a sensor head 410 and an information processing apparatus 420. The sensor head 410 and the information processing apparatus 420 are connected through a signal line 430. The blood flow measurement apparatus 400 may be a wearable device.

The living body 600 that is the blood flow measurement target has red blood cells 602 flowing through a blood vessel 601, and a stationary tissue 603.

As shown in FIG. 48, the sensor head 410 is disposed close to or in close contact with the living body 600. As shown in FIGS. 48 and 49, the sensor head 410 includes a light emitting unit 411, a light receiving unit 412, an analog signal processing unit 413, an ADC 414, a light receiving element array 463, an image analog signal processing unit 464, and an image ADC 465.

Figure 50:
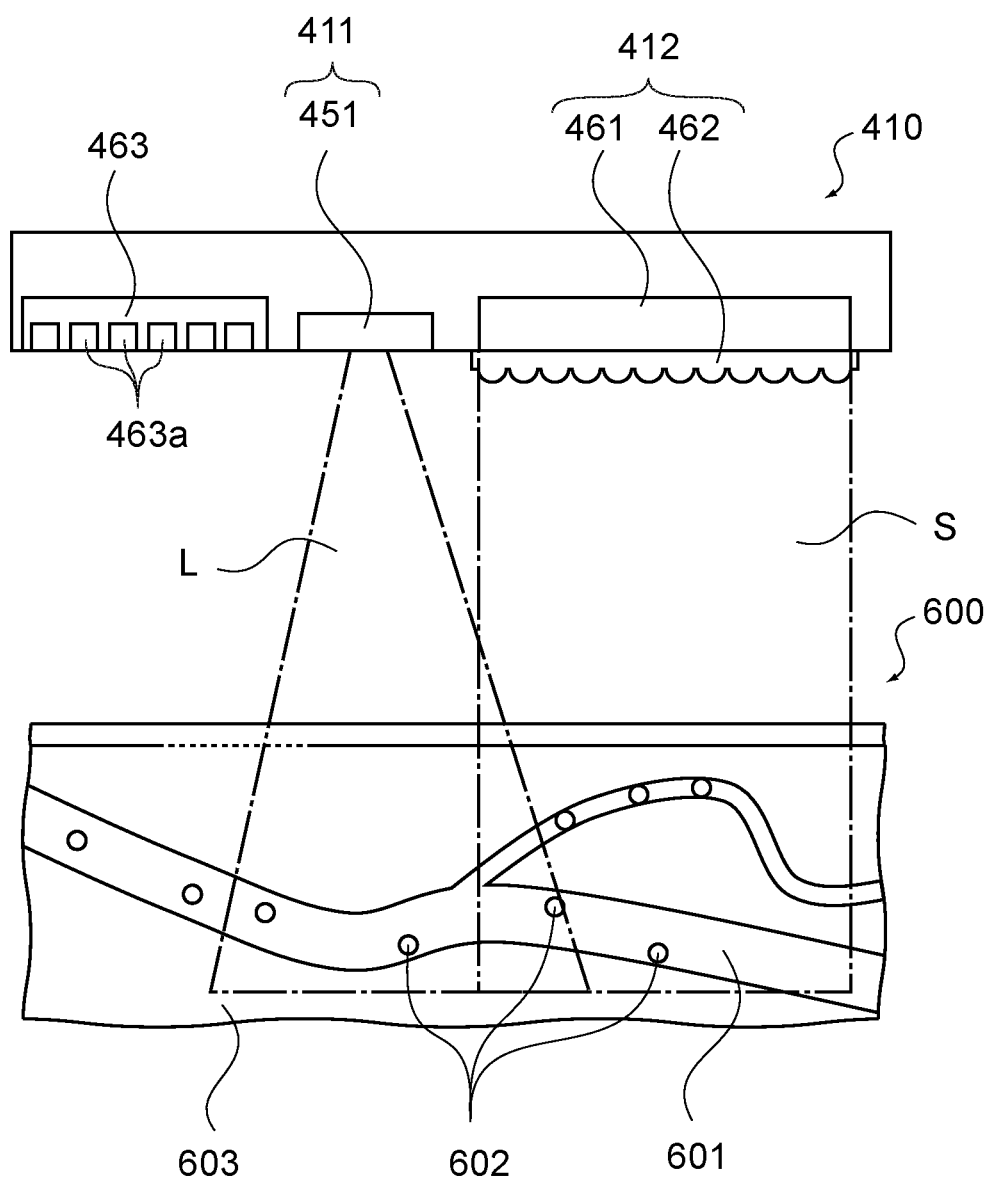
FIG. 50 A cross-sectional view of a light emitting unit and a light receiving unit of the blood flow measurement apparatus.
Figure 51:
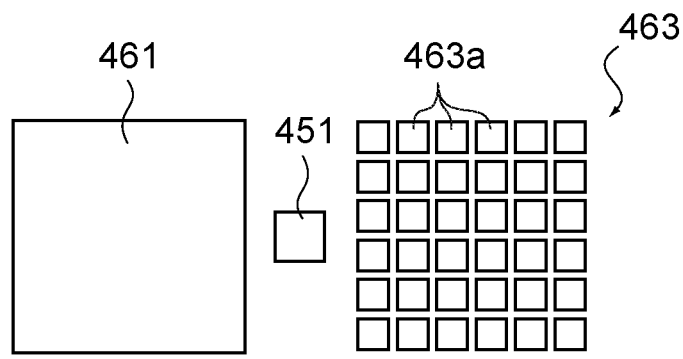
FIG. 51 A plan view of the light emitting unit and the light receiving unit of the blood flow measurement apparatus.

The light emitting unit 411 and the light receiving unit (sensor) 412 are mounted on the sensor head 410 and the relative position relative to the sensor head 410 is fixed. FIG. 50 is a cross-sectional view of a sensor head 310. FIG. 51 is a plan view of the sensor head 410 viewed from the living body 600 side.

The light emitting unit 411 irradiates the living body 600 with laser light L As shown in FIGS. 50 and 51, the light emitting unit 411 includes a laser light source 451. It should be noted that the laser light source 451 may be provided with the irradiation light control unit described in the first embodiment.

The light receiving unit 412 receives scattered light obtained when the laser light L is reflected by the living body 600 and converts the received scattered light into a signal. The light receiving unit 412 includes a measurement light receiving element 461 and an incident angle limiting unit 462.

The measurement light receiving element 461 and the incident angle limiting unit 462 can respectively have the same configuration as the measurement light receiving element 161 and the incident angle limiting unit 162 described in the first embodiment (see FIG. 18).

Further, the incident angle limiting unit 462 may have another configuration of the first embodiment (see FIGS. 27 to 35). In addition, the light receiving unit 412 may be configured to include only the measurement light receiving element 461 or not to include an incident angle limiting unit 462.

The analog signal processing unit 413 performs signal processing such as amplification on the signal output from the light receiving unit 412 and supplies it to the ADC 414.

The analog to digital converter (ADC) 414 converts the analog signal supplied from the analog signal processing unit 413 into a digital signal. The ADC 414 outputs the converted digital signal to the information processing apparatus 420 via the signal line 430.

The light receiving element array 463 is provided in the sensor head 410 and is an array in which a plurality of light receiving elements 463a is arranged. The number of light receiving elements 463a constituting the light receiving element array 463 is not particularly limited. It should be noted that a speckle particle size of a captured spatial speckle image may be adjusted by placing an optical component such as a pin hole and a lens between the light receiving element array 463 and the living body 600. Alternatively, a surface image of the living body 600 may be captured in place of the spatial speckle image by placing an optical component such as a lens between the light receiving element array 463 and the living body 600.

The image analog signal processing unit 464 performs signal processing such as amplification on the signal output from the light receiving element array 463 and supplies it to the image ADC 465.

The image ADC 465 converts the analog signal supplied from the image analog signal processing unit 464 into a digital signal. The image ADC 465 outputs the converted digital signal to the information processing apparatus 420 via the signal line 430.

As shown in FIG. 49, the information processing apparatus 420 includes a power spectrum calculation unit 421, a velocity pulse wave calculation unit 422, a relative velocity detection unit 466, a velocity correction unit 423, a pulse rate calculation unit 424, and a velocity distribution information calculation unit 425.

The power spectrum calculation unit 421 performs arithmetic processing such as Fourier transform on the beat signal obtained from the ADC 414. Accordingly, the power spectrum calculation unit 421 calculates the power spectrum of the signal that may be changed to the frequency domain for each predetermined time. The predetermined time is, for example, $1/300$ to $1/10$ seconds.

The power spectrum calculation unit 421 calculates a power spectrum for the signal beat generated from the scattered light received the measurement light receiving element 461.

The velocity pulse wave calculation unit 422 calculates a velocity pulse wave on the basis of a time-series change of the power spectrum of the beat signal output from the power spectrum calculation unit 421.

The relative velocity detection unit 466 detects the relative velocity between the sensor head 410 and the living body 600 in the xy direction (direction perpendicular to the optical axis direction (z direction) of the laser light L) on the basis of the output of the light receiving element array 463. The relative velocity detection unit 466 is capable of detecting the relative velocity on the basis of the amount of deviation for each frame in the spatial speckle image with the laser beam, which is captured by the light receiving element array 463.

The velocity correction unit 423 corrects the velocity distribution calculated on the basis of the Power spectrum using the relative velocity between the sensor head 410 and the living body 600 in the xy direction supplied from the relative velocity detection unit 466. An adaptive filter technique can be used for this removal.

The pulse rate calculation unit 424 calculates a pulse rate on the basis of the velocity pulse wave corrected by the velocity correction unit 423.

The velocity distribution information calculation unit 425 calculates velocity distribution information by performing an operation such as integral processing on the power spectrum calculated by the power spectrum calculation unit 421.

The power spectrum calculation unit 421, the velocity pulse wave calculation unit 422, the pulse rate calculation unit 424, and the velocity distribution information calculation unit 425 function as a blood flow-related information calculation unit that calculates blood flow-related information. The blood flow-related information calculation unit may have another configuration capable of calculating the blood flow-related information.

Further, the velocity correction unit 423 functions as a noise cancellation unit that cancels noise caused by the relative motion between the sensor head 410 and the living body 600 from the blood flow-related information. The noise cancellation unit may have another configuration capable of cancelling the noise.

The blood flow measurement apparatus 400 has the above-mentioned configuration. It should be noted that the sensor head 410 functions as an analog signal processing block of the blood flow measurement apparatus 400 and the information processing apparatus 420 functions as a digital signal processing block.

The configuration of the blood flow measurement apparatus 400 is not limited thereto. Digital signal processing may be performed at the sensor head 410 and analog signal processing may be performed at the information processing apparatus 420.

[Operation of Blood Flow Measurement Apparatus According to Fourth Embodiment]

An operation of the blood flow measurement apparatus 400 will be described.

As shown in FIG. 50, the living body 600 is irradiated with the laser light L from the laser light source 451 of the light emitting unit 411. The scattered light S obtained when the laser light L is reflected by the living body is received by the measurement light receiving element 461 and the light receiving element array 463.

Here, the amount of deviation of the image captured by the light receiving element array 463 for each frame is proportional to the relative velocity between the living body 600 and the sensor head 410. The relative velocity in the xy direction obtained on the basis of the deviation vector for each frame corresponds to v sin θ which determines the frequency of the relative velocity noise. The velocity correction unit 423 removes a v sin θ-correlated component included in the velocity signal calculated by the power spectrum calculation unit 421. The adaptive filter technique can be applied to this removal.

In the blood flow measurement apparatus 400, the disturbance noise can be prevented from being generated as described above.

[Variations of Light Receiving Unit]

Figure 52:
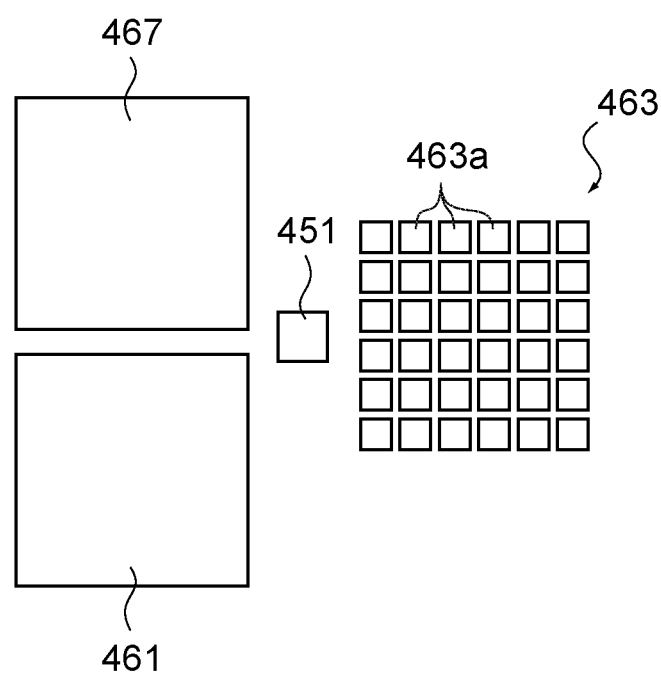
FIG. 52 A schematic diagram showing another configuration of the light receiving unit of the blood flow measurement apparatus.

The light receiving unit 412 is not limited to the above-mentioned configuration. FIG. 52 is a schematic diagram showing a light receiving unit 412 having another configuration.

As shown in the figure, the light receiving unit 412 may include another measurement light receiving element 467 in addition to the measurement light receiving element 461. As in the measurement light receiving element 461, the measurement light receiving element 467 is a light receiving element for measuring a beat signal generated due to the motion of the red blood cell 602.

By taking a difference between the beat signal received by the measurement light receiving element 461 and the measurement light receiving element 467, it is possible to cancel noise of a noise source such as external light, which causes similar changes in both the pixels.

[Hardware Configuration]

Figure 53:
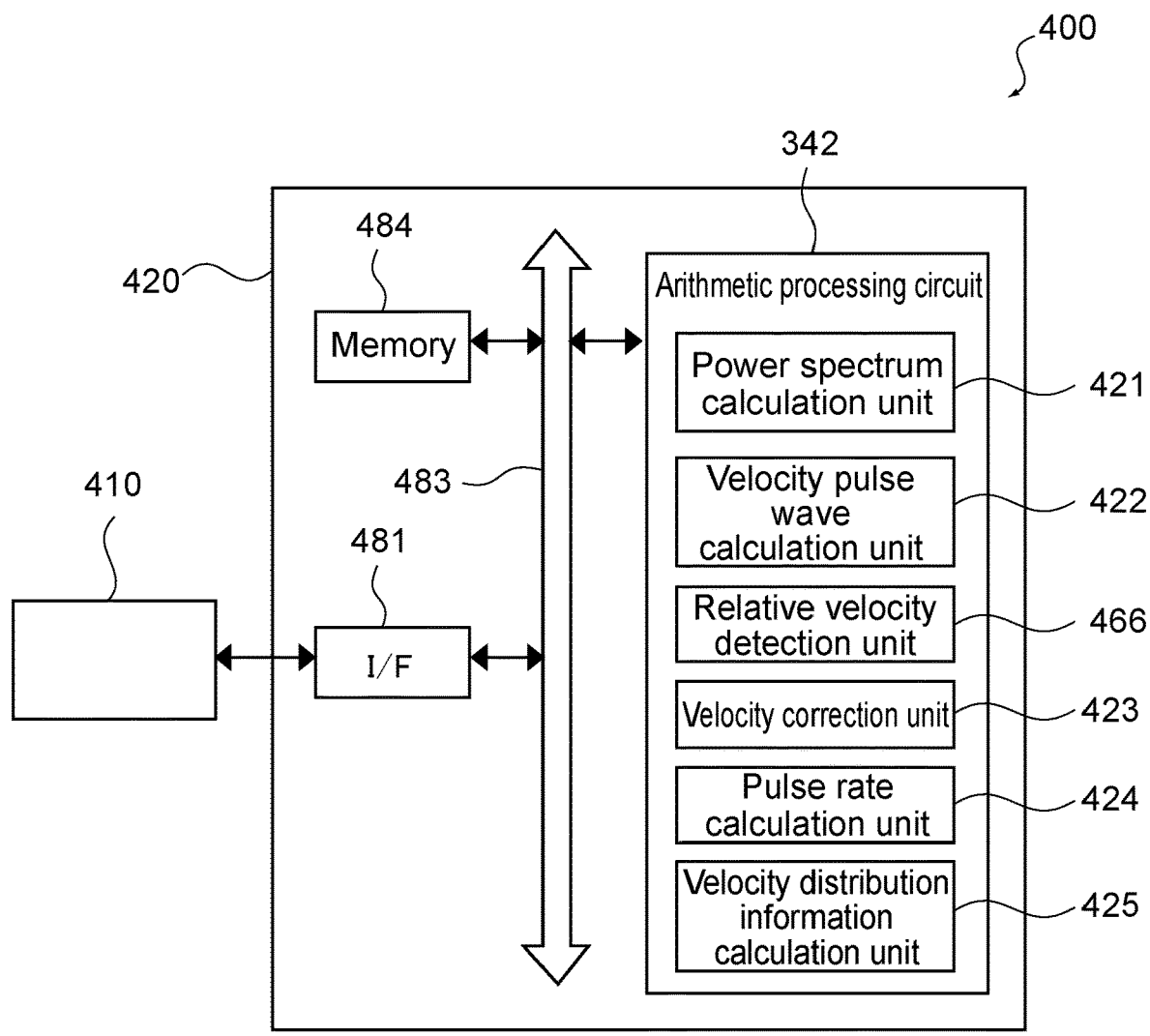
FIG. 53 A block diagram showing a hardware configuration of an information processing apparatus of the blood flow measurement apparatus.

A hardware configuration of the information processing apparatus 420 will be described. FIG. 53 is a schematic diagram showing a hardware configuration of the information processing apparatus 420. As shown in the figure, the information processing apparatus 420 includes an interface (I/F) 481, arithmetic processing circuit 482, a bus 483, and a memory 484.

The I/F 481 provides a beat signal obtained from the sensor head 410 (see FIG. 10) to the buses 483. Further, the image data of the light receiving element array 463 obtained from the sensor head 410 is also supplied to the bus 483. The arithmetic processing circuit 482 is a processor such as a central processing unit (CPU). A beat signal and image data are obtained via the bus 483 and various types of arithmetic processing are performed while exchanging information with the memory 484.

The power spectrum calculation unit 421, the velocity pulse wave calculation unit 422, the relative velocity detection unit 466, the velocity correction unit 423, the pulse rate calculation unit 424, and the velocity distribution information calculation unit 425 having the above-mentioned functional configurations are realized by the cooperation of the arithmetic processing circuit 482 and the program.

It should be noted that some or all of the configurations of the information processing apparatus 420 may be realized on a computer network.

(Other Configurations)

The light emitting unit and the light receiving unit of the blood flow measurement apparatus according to each of the above-mentioned embodiments can have configurations shown below. In the following description, the same reference signs as those of the first embodiment are given to the same configurations as those of the first embodiment, but they can also be applied to the second to fourth embodiments.

(Use of Louver Filter)

The light receiving unit of the blood flow measurement apparatus according to each of the above-mentioned embodiments includes an incident angle limiting unit that limits the incident angle of light incident on the measurement light receiving element to a predetermined angle or less. Here, a louver-type optical path limiting filter (hereinafter, referred to as louver filter) may be used as the incident angle limiting unit. The louver filter is often used as a filter for peep prevention of a display.

Figure 54:
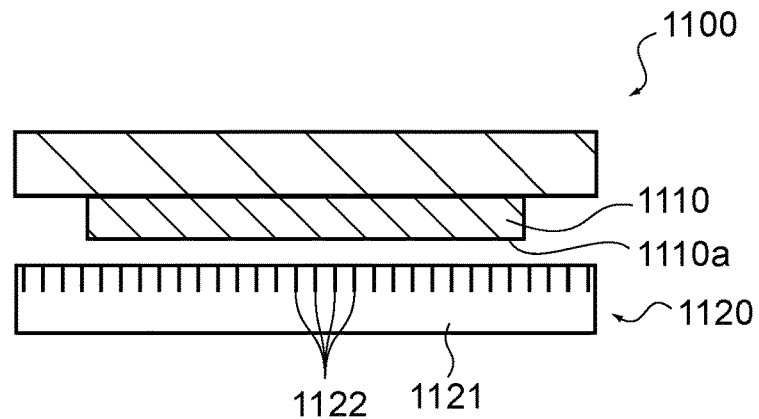
FIG. 54 A cross-sectional view of a light receiving unit of a blood flow measurement apparatus according to an embodiment of the present technology.

FIG. 54 is a schematic diagram showing a light receiving unit 1100 including an incident angle limiting unit using a louver filter. As shown in the figure, the light receiving unit 1100 includes a measurement light receiving element 1110 and a louver filter 1120.

The measurement light receiving element 1110 can have the same configuration as the measurement light receiving element 161 described in the first embodiment. The measurement light receiving element 1110 includes a light receiving surface 1110a.

The louver filter 1120 functions as an incident angle limiting unit. The louver filter 1120 includes a light transmissive member 1121 and louvers 1122. The thickness of the louver filter 1120 is, for example, 0.3 mm.

The light transmissive member 1121 is made of a material that transmits at least scattered light. Each of the louvers 1122 is a plate-like member made of a material that does not transmit light having a wavelength of scattered light, the main surface of which extends along a direction perpendicular to the light receiving surface 1110a. The plurality of louvers 1122 is embedded in the light transmissive member 1121 in a predetermined arrangement.

Figure 55:
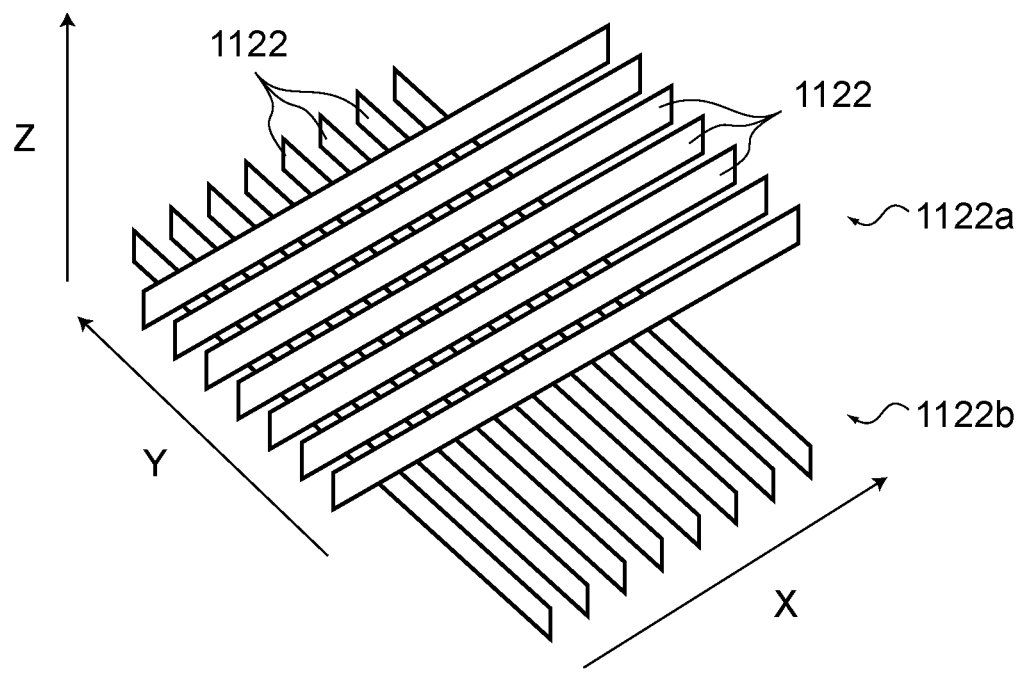
FIG. 55 A schematic diagram of a louver filter of a light receiving unit of the blood flow measurement apparatus.

FIG. 55 is a schematic diagram showing the arrangement of the louvers 1122. As shown in the figure, the louver filter 1120 includes a first louver layer 1122a and a second louver layer 1122b. The first louver layer 1122a includes a plurality of louvers 1122 extending parallel to an X direction with a predetermined spacing. The second louver layer 1122b includes a plurality of louvers 1122 extending parallel to a Y direction with a predetermined spacing. The X direction and the Y direction are directions crossing each other. Typically, the X direction and the Y direction are orthogonal to each other. Further, a direction orthogonal to the X and Y directions defined as a Z direction.

The height (Z direction) and spacing (X and Y directions) of the louvers 1122 is adjustable. The louvers 1122, for example, may have a height of about 130 µm and a spacing of about 40 µm.

Figure 56:
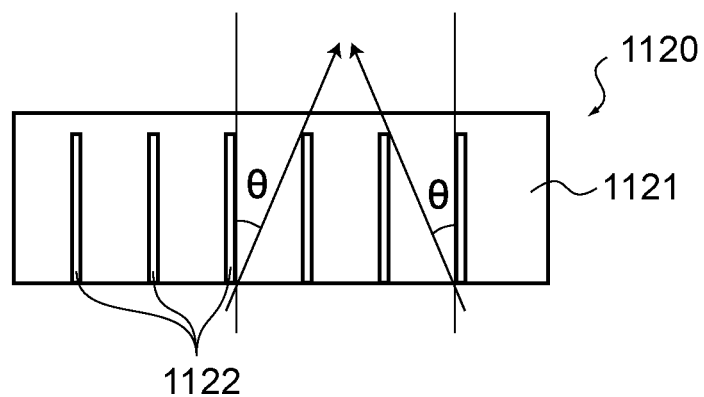
FIG. 56 A schematic diagram of the louver filter of the light receiving unit of the blood flow measurement apparatus.

The louver filter 1120 limits the incident angle of light incident on the louver filters 1120 to be equal to or smaller than a predetermined angle through the louvers 1122. FIG. 56 is a schematic diagram showing limitation of the incident angle of the incident light by the louver filter 1120.

As shown in the figure, components of light incident on the louver filter 1120, the angle θ of which is equal to or higher than a certain angle, are absorbed by the louvers 1122 and do not transmit through the louver filter 1120. That is, the louver filter 1120 limits the incident angle of light incident on the measurement light receiving element 1110 to be equal to or smaller than the predetermined angle. It should be noted that the figure shows limitation of the incident angle in one of the X direction and Y direction, though similar limitation of the incident angle is done for the other. Further, the louver filter 1120 may have one louver layer or may have three or more louver layers. For example, in the case of a single-layer louver in the X direction, the limitation in the Y direction in which the angle is not limited by the louver can be performed by providing a light shielding window on the living body 600 side of the louver filter 1120 or the like.

The louver filter can set the limiting angle θ in a wide range of about 5° to 30° by adjusting the height and spacing of the louvers 1122. It is favorable for the angular limitation of the present technology.

By using the louver filter 1120 in the incident angle limiting unit, it is possible to extremely thin the thickness of the incident angle limiting unit unlike the general light shield and the pin hole. It is thus possible to increase the utilization efficiency of light. Further, the louvers 1122 can be arranged at very close pitches (<40 µm), which is difficult with conventional light shields.

Further, the light transmissive member 1121 may be made of a material such as IR black that shields light other than infrared rays. Accordingly, the louver filter 1120 is capable of shielding external light (sunlight) or the like that affects blood flow measurement. The sensor head can be thus thinned.

Figure 57:
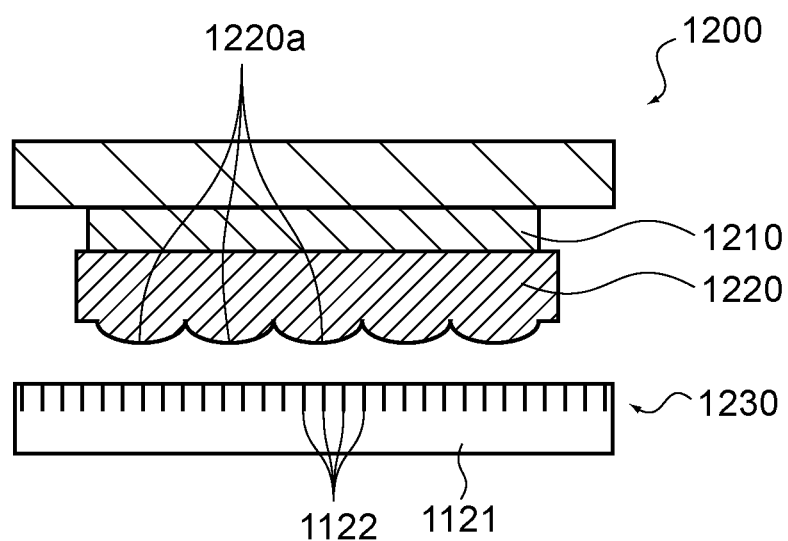
FIG. 57 A cross-sectional view of the light receiving unit of the blood flow measurement apparatus.

In addition, the light receiving unit may include a louver filter and a lens array. FIG. 57 is a schematic diagram of a light receiving unit 1200 including a measurement light receiving element 1210, a lens array 1220, and a louver filter 1230.

The measurement light receiving element 1210 can have the same configuration as the measurement light receiving element 161 described in the first embodiment.

The lens array 1220 is constituted by an optical member and can be a lens array in which a plurality of lenses 1220a is arranged. By bringing the lens array 1220 into contact with the measurement light receiving element 1210, it is possible to facilitate the fixing of the positional relationship between the lens array 1220 and the measurement light receiving element 1210.

The louver filter 1230 is disposed in front of the lens array 1220 (opposite to the measurement light receiving element 1210) and has the same configuration as the louver filter 1120.

Since the louver filter 1230 is disposed in front of the lens array 1220, the louvers 1122 have narrow pitches. Therefore, it is possible to limit the incident angle to the measurement light receiving element 1210 even without adjusting the predetermined positional relationship by defining the positional relationship between the lens array 1220 and the louvers 1122. Without limiting the positional relationship, moire is generated in light incident on the measurement light receiving element 1210 under the influence of two different periodic structures. However, since the blood flow measurement apparatus according to the present technology does not utilize an image of incident light, generation of moire can be tolerated. Further, since the incident angle limiting unit is separated from the lens array 1220, the lenses can be densely paved in the lens array 1220, and only light having an incident angle at which the light is mixed between the neighboring lenses 1220a is removed. Therefore, it is possible to improve the utilization efficiency of light.

It should be noted that the lens array 1220 and the louvers 1122 may also be configured to limit the positions to a particular relationship as described below.

Figure 58:
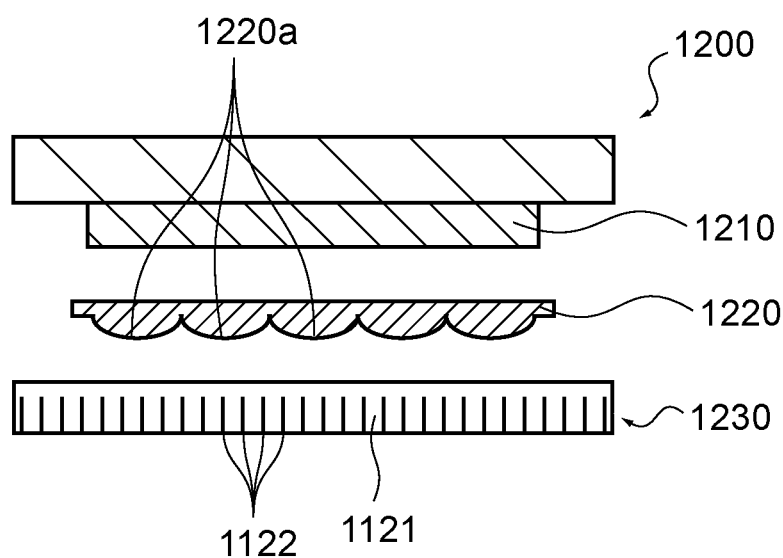
FIG. 58 A cross-sectional view of the light receiving unit of the blood flow measurement apparatus.
Figure 59:
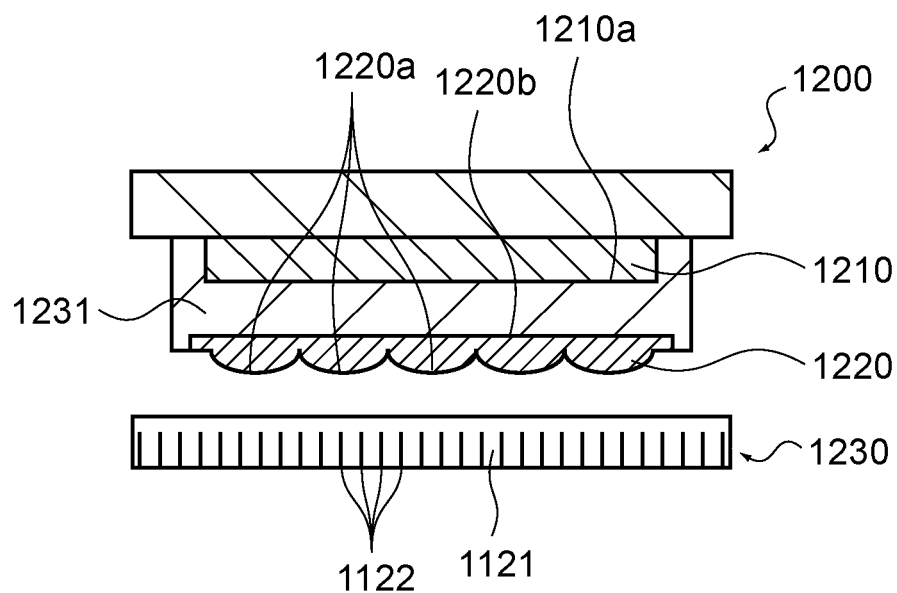
FIG. 59 A cross-sectional view of the light receiving unit of the blood flow measurement apparatus.
Figure 60:
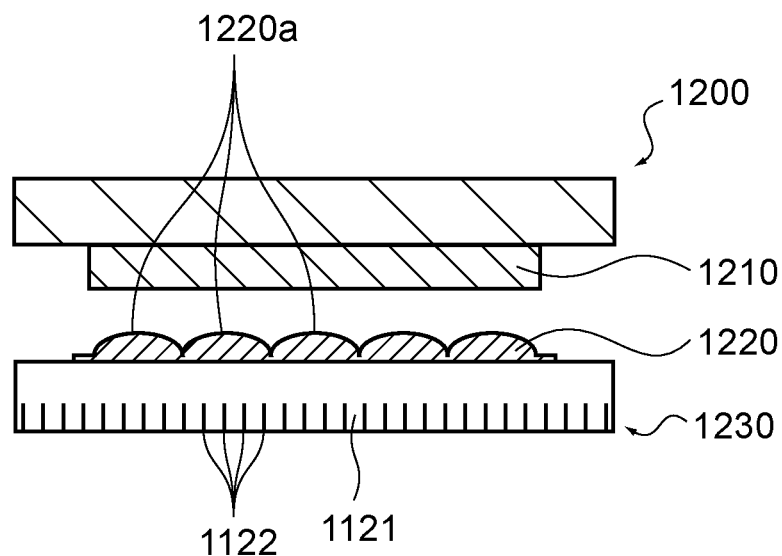
FIG. 60 A cross-sectional view of the light receiving unit of the blood flow measurement apparatus.

FIGS. 58 to 60 are schematic diagrams each showing a variation of the light receiving unit 1200. As shown in FIG. 58, the lens array 1220 may be spaced apart from the measurement light receiving element 1210 and an air layer may be provided between the lens array 1220 and the measurement light receiving element 1210. With this configuration, the focal length of the lens 1220a can be shortened.

In addition, as shown in FIG. 59, the lens array 1220 and the measurement light receiving element 1210 may be spaced apart and a filler 1231 such as a mold resin may be disposed therebetween. With this configuration, it is possible to adjust the height and tilt of the lens array 1220. The resistance to the flatness of a light receiving surface 1210a of the measurement light receiving element 1210 and a flat surface 1220b which is the back surface of the lens array 1220 can be improved.

In addition, as shown in FIG. 60, the lens array 1220 may be provided in contact with the louver filter 1120. The louver filter 1120 may be disposed such that the louvers 1122 are opposite to the measurement light receiving element 1210 as shown in the figure.

With any configuration of the light receiving unit 1200, one or both of the lens array 1220 and the light transmissive member 1121 may be made of a material that shields light other than infrared rays, such as IR black.

Figure 61:
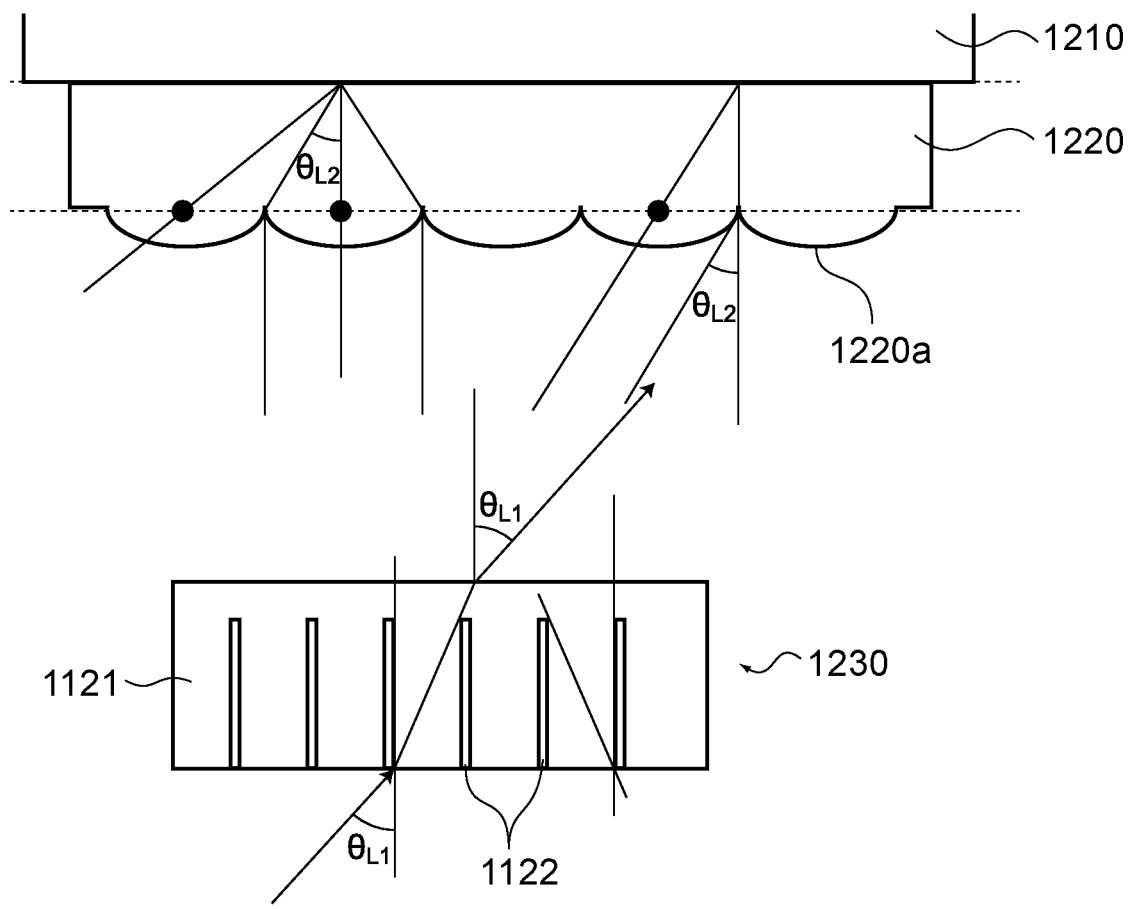
FIG. 61 A schematic diagram of the louver filter of the light receiving unit of the blood flow measurement apparatus.

FIG. 61 is a schematic diagram showing a relationship between the opening of the lens 1220a and the aspect ratio of the louvers 1122 when the lens array 1220 is in contact with the measurement light receiving element 1210. As shown in the figure, it is assumed that $\theta_{L2}$ is an allowable upper limit incident angle of the lens 1220a at which the incident light enters the adjacent lens 1220a at an angle deviating from the incident angle range of $\pm\theta_{L2}$ in the lens

1220a and $\theta_{L1}$ is an emission upper limit angle when the louver filter 1230 limits the exit angle to the range of $\pm\theta_{L1}$.

In this case, a site (irradiation spot R, see FIG. 18) of the observation target, which emits the scattered light S, is located in the front of the measurement light receiving element 1210 (emits light in the front of the measurement light receiving element 1210), it is possible to prevent mixing of light with the adjacent lens 1220a by satisfying tan $\theta_{L2}$>tan $\theta_{L1}$.

Further, when a site of the observation target, which emits the scattered light S, is located in one direction of the measurement light receiving element 1210 (emits light in the front of the light emitting unit), it is possible to prevent mixing of light with the adjacent lens 1220a by satisfying tan $\theta_{L2}$>2 tan $\theta_{L1}$.

Figure 62:
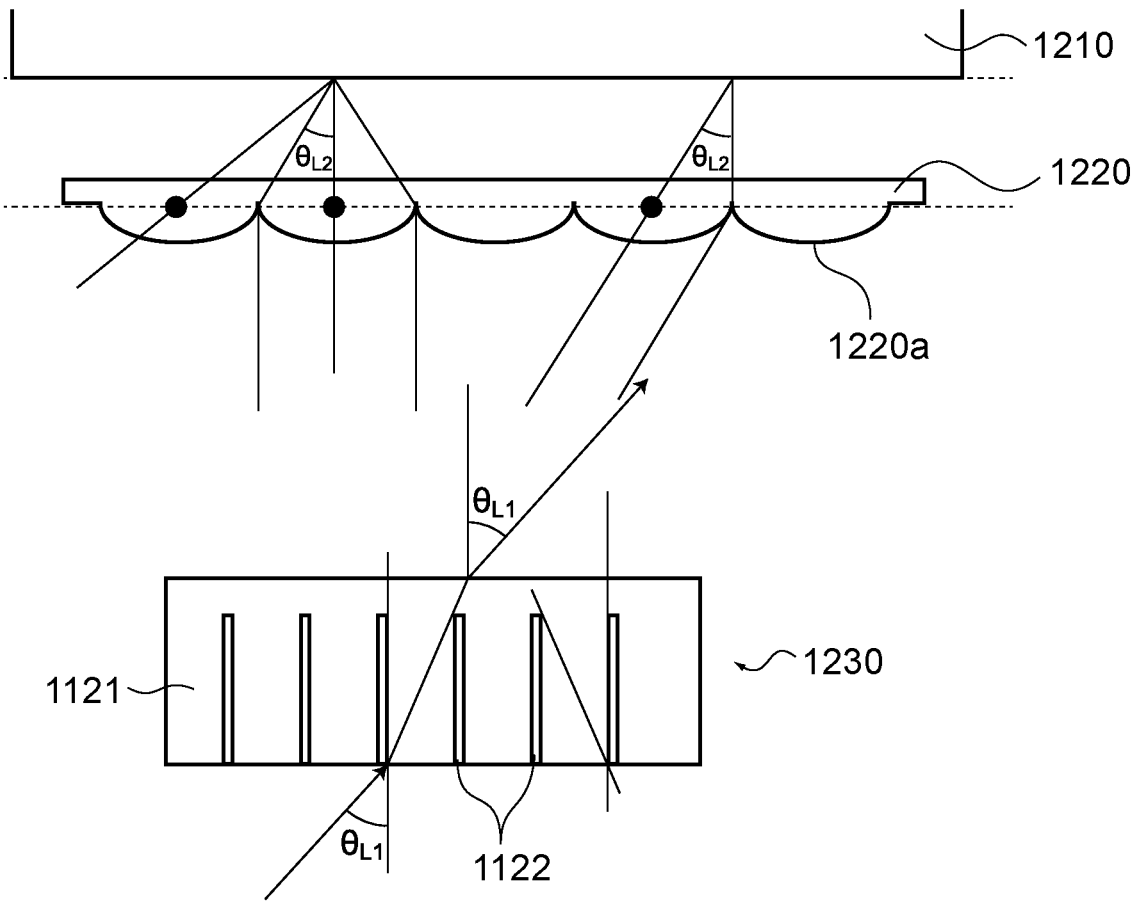
FIG. 62 A schematic diagram of the louver filter of the light receiving unit of the blood flow measurement apparatus.

FIG. 62 is a schematic diagram showing a relationship between the opening of the lens 1220a and the aspect ratio of the louvers 1122 in a case where an air layer exists between the lens array 1220 and the measurement light receiving element 1210. In this case, as shown in the figure, it is sufficient that $\theta_{L2}$ may be considered as an angle in the air layer. Other points are similar to those in the case of FIG. 61.

Figure 63:
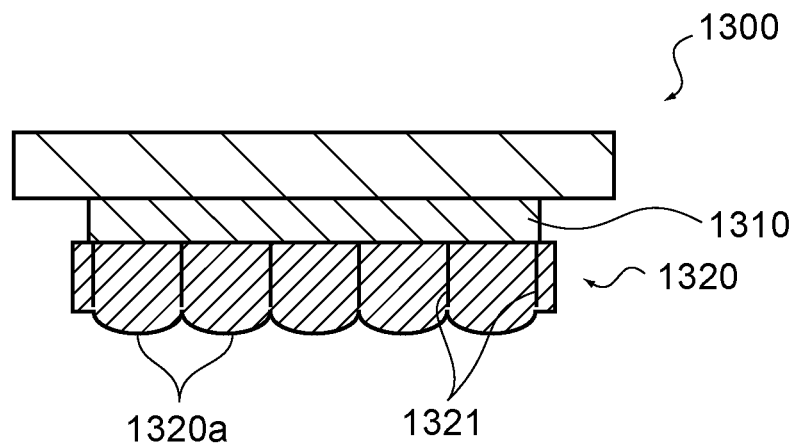
FIG. 63 A schematic diagram of the louver filter of the light receiving unit of the blood flow measurement apparatus.

Further, the light receiving unit may include louvers and a lens array that are integrated defining the positional relationship between the louvers and the lens array. FIG. 63 is a schematic diagram of a light receiving unit 1300 including a measurement light receiving element 1310 and a louver (hereinafter, referred to as louver lens array) 1320 integrated with a lens array.

The measurement light receiving element 1310 can have the same configuration as the measurement light receiving element 161 described in the first embodiment.

The louver lens array 1320 is constituted by an optical member and can be a lens array in which a plurality of lenses 1320a is arranged. Louvers 1321 are disposed between the individual lenses 1320a. Like the louvers 1122, the louvers 1321 are arranged in parallel with a predetermined spacing in the X and Y directions. Alternatively, in a case where the lens array is arranged in a honeycomb shape, louvers are arranged on side portions of the hexagon, which correspond to the walls of the honeycomb.

Accordingly, individual lenses 1320a are separated from neighboring lenses 1320a by the louvers 1321.

As described above, it is possible to remove only the light mixed with the adjacent lens 1320a and make the other light incident on the measurement light receiving element 1310 by integrating the louvers and the lens array. Maximum light utilization efficiency can be realized. The louver lens array 1320 may be made of a material that shields light other than infrared rays, such as IR black.

It should be noted that in the light receiving unit 1200 and the light receiving unit 1300, the louvers 1122 and the louvers 1321 does not need to be perpendicular to the light receiving surface of the measurement light receiving element, and the louvers 1122 and the louvers 1321 may be inclined with respect to the light receiving surface.

Figure 64:
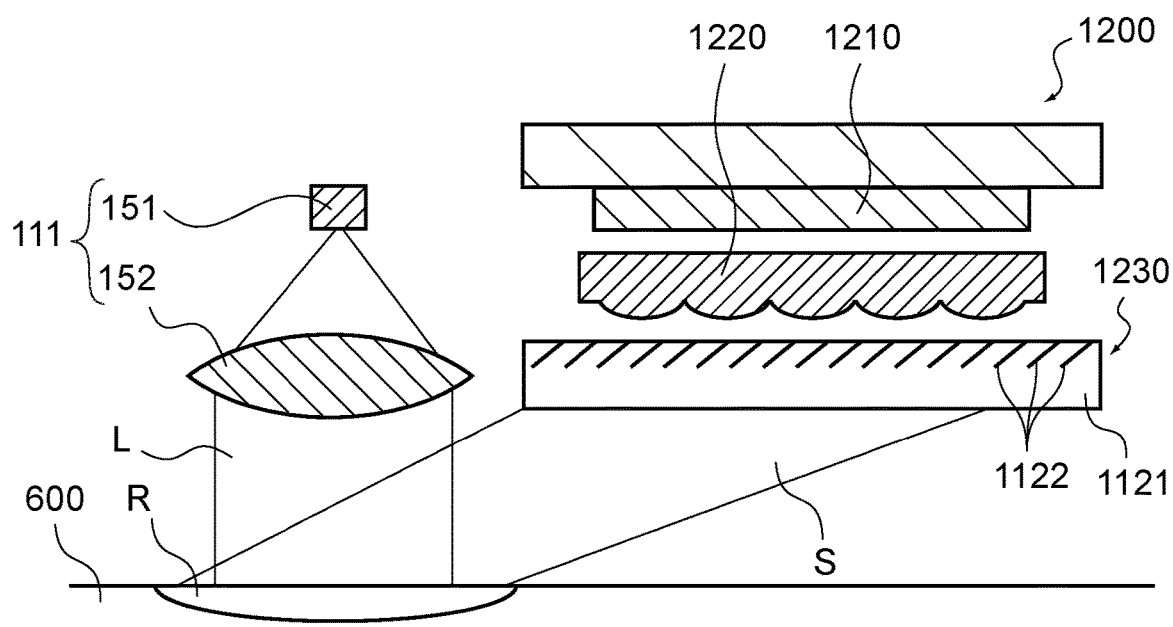
FIG. 64 A cross-sectional view of the light receiving unit of the blood flow measurement apparatus.
Figure 65:
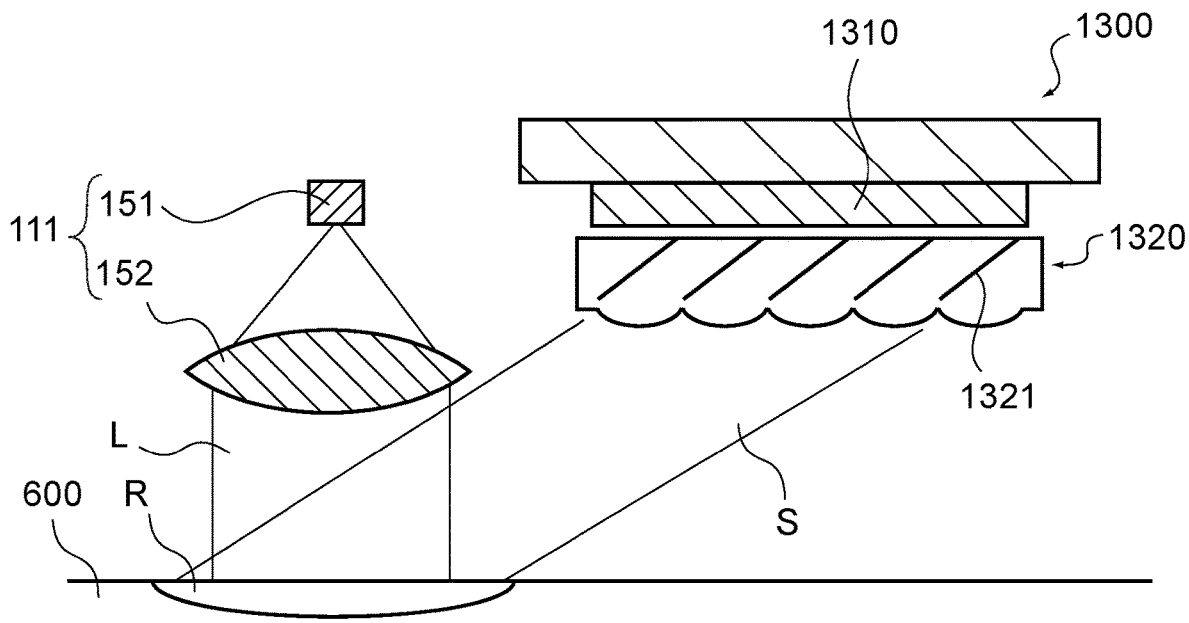
FIG. 65 A cross-sectional view of the light receiving unit of the blood flow measurement apparatus.

FIG. 64 is a schematic diagram showing a louver filter 1230 in which one of two louver layers is inclined. FIG. 65 is a schematic diagram showing a louver lens array 1320 in which one of two louver layers is inclined.

As shown in these figures, in a case where the irradiation spot R is present in the living body 600 in front of the light emitting unit 111 (see FIG. 18), a large amount of scattered light S emitted from the irradiation spot R can be guided to the measurement light receiving element by tilting the louvers.

(Use of Polarization Filter)

The light receiving unit of the blood flow measurement apparatus according to each of the above-mentioned embodiments may include a polarization filter as an incident angle limiting unit.

Figure 66:
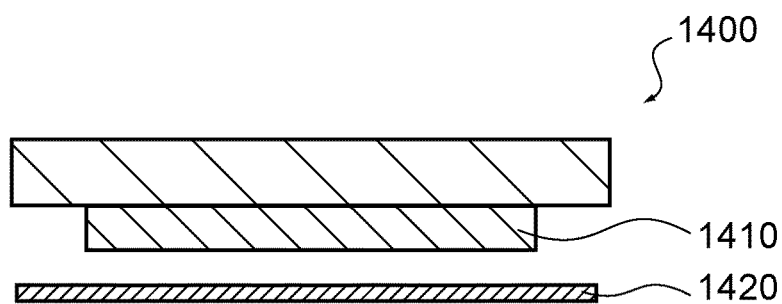
FIG. 66 A cross-sectional view of the light receiving unit of the blood flow measurement apparatus.

FIG. 66 is a schematic diagram showing a light receiving unit 1400 including a polarization filter. As shown in the figure, the light receiving unit 1400 includes a measurement light receiving element 1410 and the polarization filter 1420.

The measurement light receiving element 1410 can have the same configuration as the measurement light receiving element 161 described in the first embodiment.

The polarization filter 1420 is a filter that attenuates a component of light having a polarization direction that is a specific direction. As shown in FIG. 66, it is disposed between the measurement light receiving element 1410 and the measurement target (living body). The polarization filter 1420 can be oriented in accordance with the polarization direction of the laser light source.

Figure 67:
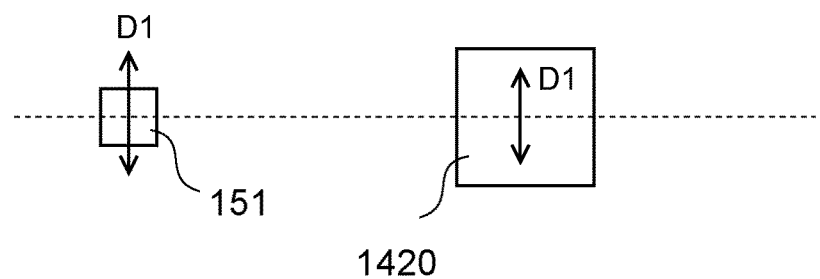
FIG. 67 A plan view of the light emitting unit and the light receiving unit of the blood flow measurement apparatus.

FIG. 67 is a schematic diagram showing the polarization direction of the polarization filter 1420 and is a plan view of the sensor head as viewed from the living body side. The laser light source 151 emits linearly polarized laser light. FIG. 67 shows the polarization direction of the laser light emitted from the laser light source 151 as a direction D1. It should be noted that the polarization direction of laser light is not limited to that shown in the figure.

As shown in the figure, the polarization filter 1420 is arranged such that the polarization direction is the direction D1. By making the polarization direction of the polarization filter 1420 the same as the polarization direction of the laser light source 151, scattered light generated by single scattering in the living body passes through the polarization filter 1420 almost as it is.

On the other hand, the direction of polarization of the scattered light generated by multiplex scattering in the living body becomes random by multiple scattering. Therefore, the amount of light is halved when the light is transmitted through the Polarization filter 1420. In addition, the amount of external light is also halved.

Accordingly, the resistance to external light is improved about twice and the brightness of the irradiation spot directly hit by the laser becomes conspicuous, resulting in the effect of limiting the incident angle. Accordingly, another incident angle limiting mechanism can be omitted or can have a simplified configuration, and the polarization filter 1420 functions as an incident angle limiting unit.

Figure 68:
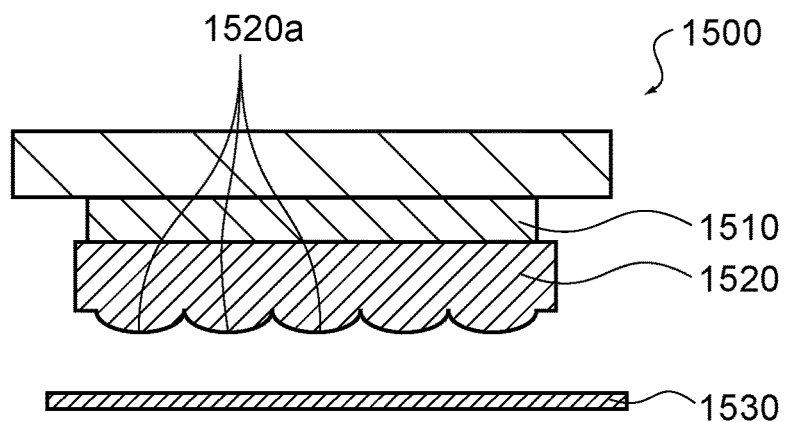
FIG. 68 A cross-sectional view of the light receiving unit of the blood flow measurement apparatus.

Further, the polarization filter may be combined with another incident angle limiting mechanism. FIG. 68 is a schematic diagram showing a light receiving unit 1500 including a polarization filter and another incident angle limiting mechanism. As shown in the figure, the light receiving unit 1500 includes a measurement light receiving element 1510, a lens array 1520, and a polarization filter 1530.

The measurement light receiving element 1510 can have the same configuration as the measurement light receiving element 161 described in the first embodiment.

The lens array 1520 serves as an incident angle limiting unit. The lens array 1520 is constituted by an optical member and is a lens array in which a plurality of lenses 1520a is arranged. Further, the lens array 1520 may be a pin hole structure (see FIG. 35) and may be a louver-type privacy louver filter 1120 as described above.

The polarization filter 1530 is a filter that attenuates a component of light having a polarization direction that is a specific direction. As shown in FIG. 68, it is disposed between the lens array 1520 and the measurement target (living body). Further, the polarization filter 1530 may be disposed between the lens array 1520 and the measurement light receiving element 1510.

Figure 69:
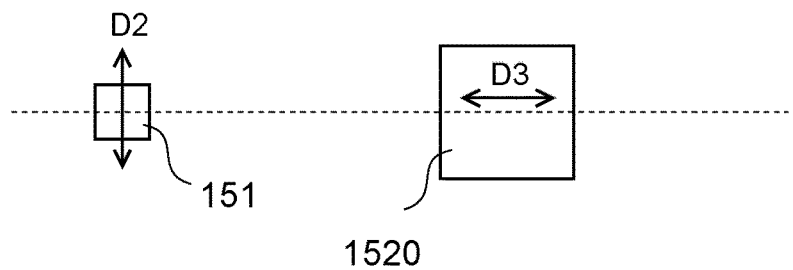
FIG. 69 A plan view of the light emitting unit and the light receiving unit of the blood flow measurement apparatus.

The polarization filter 1530 can be oriented in accordance with the polarization direction of the laser light source. FIG. 69 is a schematic diagram showing the polarization direction of the polarization filter 1530 and is a plan view of the sensor head as viewed from the living body side. The laser light source 151 emits linearly polarized laser. FIG. 69 shows the polarization direction of the laser light source 151 as a direction D2. It should be noted that the polarization direction of laser light source 151 is not limited to that shown in the figure.

As shown in the figure, the polarization filter 1530 is arranged such that the polarization direction is a direction D3. The direction D3 is a direction perpendicular to the direction D2. By making the polarization direction of the polarization filter 1530 orthogonal to the polarization direction of the laser light source 151, light that has caused single scattering in the living body is blocked by the polarization filter 1530.

Accordingly, the ratio of light from measurement target particles in blood, which is contained in the scattered light incident on the measurement light receiving element 1510, is greatly increased. Only multiple scattered light is observed. Therefore, although the absolute amount of light incident on the measurement light receiving element 1510 is reduced, an S/DC ratio (ratio of the amount of beat to the amount of light) is improved. Therefore, in a case where the incident intensity of the coherent light is sufficiently high relative to the incident intensity of the external light, it is favorable when lowering the intensity of the coherent light by increasing the amplification factor of the electric circuit and performing a low-power operation.

It should be noted that in the above-mentioned configuration, the polarization direction of the polarization filter 1530 may be set in the direction D2. In that case, the performance of resistance to the external light is enhanced.

Figure 70:
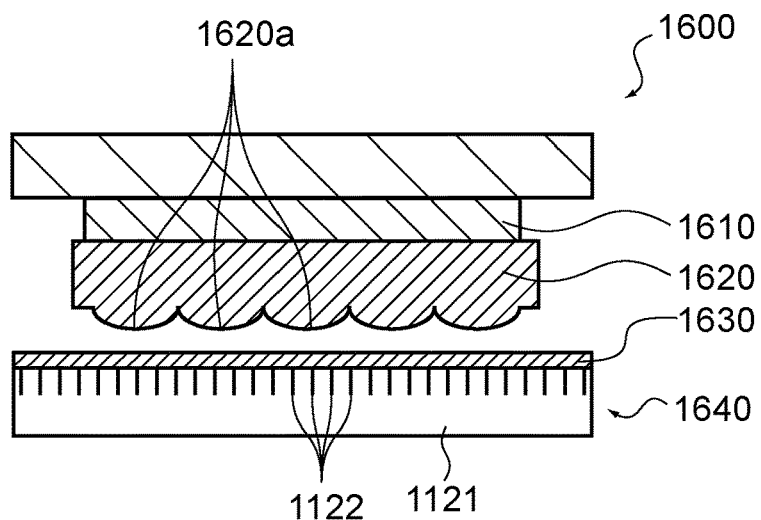
FIG. 70 A cross-sectional view of the light receiving unit of the blood flow measurement apparatus.

In addition, the polarization filter may be combined with a louver filter. FIG. 70 is a schematic diagram showing a light receiving unit 1600 including a polarization filter and a louver filter. As shown in the figure, the light receiving unit 1600 includes a measurement light receiving element 1610, a lens array 1620, a polarization filter 1630, and a louver-type privacy filter (hereinafter, referred to as louver filter) 1640.

The measurement light receiving element 1610 can have the same configuration as the measurement light receiving element 161 described in the first embodiment.

The lens array 1620 serves as an incident angle limiting unit. The lens array 1620 is constituted by an optical member and is a lens array in which a plurality of lenses 1620*a* is arranged.

The polarization filter 1630 is a filter that attenuates a component of light having a polarization direction that is a specific direction. As shown in FIG. 70, it is disposed between a louver filter 1640 and the lens array 1620. In this case, the polarization filter is configured to be incorporated in a part of the incident angle limiting unit. Further, the polarization filter 1630 may be disposed between the louver filter 1640 and the measurement target (living body).

The louver filter 1640 is disposed between the lens array 1620 and the living body and has the same configuration as the louver filter 1120.

The polarization filter 1630 can be installed with S-polarized light (large wristwatch-type device or the like) for the purpose of reducing power consumption under favorable conditions or can be installed with P-polarized light for the purpose of resistance to high external light conditions (wristband of thin design or the like).

Figure 71:
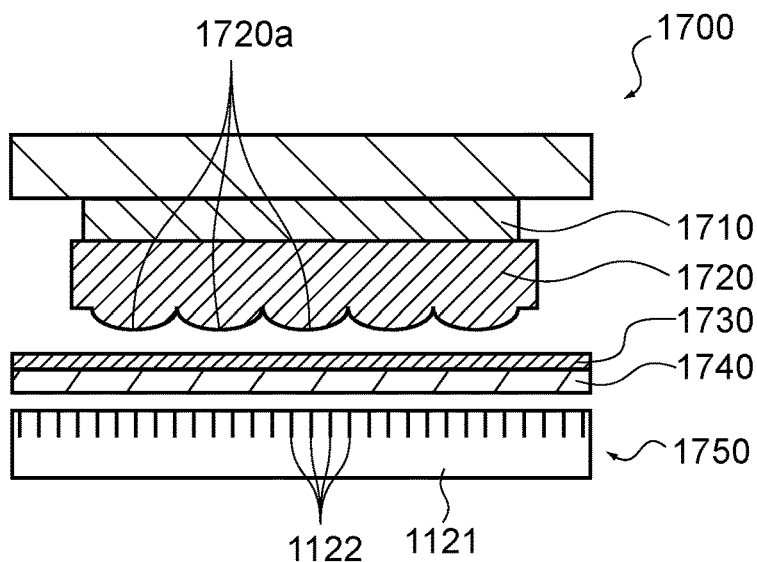
FIG. 71 A cross-sectional view of the light receiving unit of the blood flow measurement apparatus.

In addition, the polarization filter may be combined with a louver-type privacy filter and a liquid crystal plate. FIG. 71 is a schematic diagram showing a light receiving unit 1700 including a polarization filter, a louver-type privacy filter, and a liquid crystal plate. As shown in the figure, the light receiving unit 1700 includes a measurement light receiving element 1710, a lens array 1720, a polarization filter 1730, a liquid crystal plate 1740, and a louver-type privacy filter (hereinafter, referred to as louver filter) 1750.

The measurement light receiving element 1710 can have the same configuration as the measurement light receiving element 161 described in the first embodiment.

The lens array 1720 serves as an incident angle limiting unit. The lens array 1720 is constituted by an optical member and is a lens array in which a plurality of lenses 1720*a* is arranged.

The polarization filter 1730 is a filter that attenuates a component of light having a polarization direction that is a specific direction. As shown in FIG. 71, it is disposed between the lens array 1720 and the liquid crystal plate 1740.

The liquid crystal plate 1740 has a polarization direction which is rotated by 90 degrees between a state in which a voltage is applied and a state in which a voltage is not applied. The liquid crystal plate 1740 is disposed between the polarization filter 1730 and a louver filter 1750.

The louver filter 1750 is disposed between the liquid crystal plate 1740 and the living body and has the same configuration as the louver filter 1120.

The polarization filter 1730 can be disposed in a direction in which the S-polarized light passes in a state in which no voltage is applied to the liquid crystal plate 1740. Accordingly, under a favorable condition with less ambient light, the S-polarized light can be used to reduce the power consumption. In a condition in which there is a lot of ambient light, the P-polarized light can be used by applying a voltage to the liquid crystal plate 1740 to enhance the external light resistance.

(Regarding Polarization Direction of Laser Light)

When a laser light source having linearly polarized light is used in the light emitting unit of the blood flow measurement apparatus according to each of the above-mentioned embodiments, it is favorable to set the polarization direction in a predetermined direction. It should be noted that the light receiving unit may include the polarized filter as described above or does not need to include the polarization filter.

Figure 72:
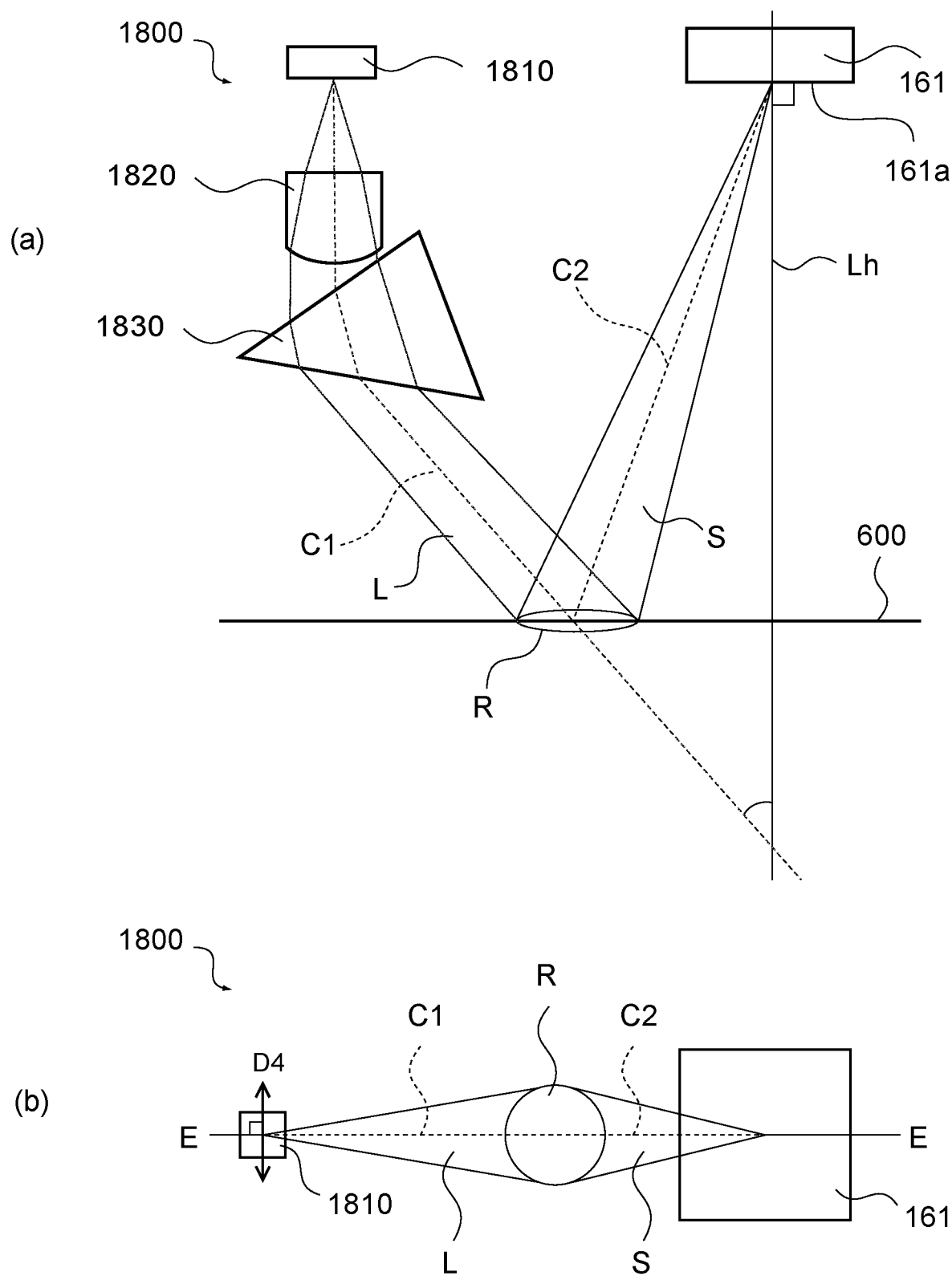
FIG. 72 A schematic diagram of the light emitting unit and the light receiving unit of the blood flow measurement apparatus.

FIG. 72 is a schematic diagram showing an optical path of the laser light L in a light emitting unit 1800 where the laser beam has a specific polarization direction. FIG. 72(*a*) is a side view. FIG. 72(*b*) is a plan view. As shown in the figure, the light emitting unit 1800 includes a laser light source 1810, a lens 1820, and a prism 1830.

The laser light source 1810 can have the same configuration as the laser light source 151 described in the first embodiment. More favorably, the laser light source 1810 is configured to emit laser light having a predetermined direction described below as the polarization direction.

The lens 1820 collimates the incident laser light and makes it incident on the prism 1830. The prism 1830 refracts the incident laser light and tilts its path.

The laser light L emitted from the prism 1830 is incident on the living body 600 to form a spot R. The scattered light S emitted from the spot R is received by the measurement light receiving element 161. It should be noted that in the figure, the incident angle limiting unit (see FIG. 18) is not shown.

As shown in FIG. 72(a), when a straight line perpendicular to a light receiving surface 161a of the measurement light receiving element 161 is defined as a perpendicular line Lh, a configuration in which an optical axis C1 of the laser light L emitted from the prism 1830 is inclined with respect to the perpendicular line Lh is employed. It should be noted that the configuration in which the laser light L is inclined is not limited to the one shown here. The details will be described later.

Further, as shown in FIG. 72(b), the optical axis of the scattered light S received by the measurement light receiving element 161 is defined as an optical axis C2 and the plane formed by the optical axis C1 and the optical axis C2 of the laser light L is defined as a plane E. The light emitting unit 1800 is configured such that the polarization direction of the laser light L is a direction perpendicular to the plane E (in the figure, direction D4).

Figure 73:
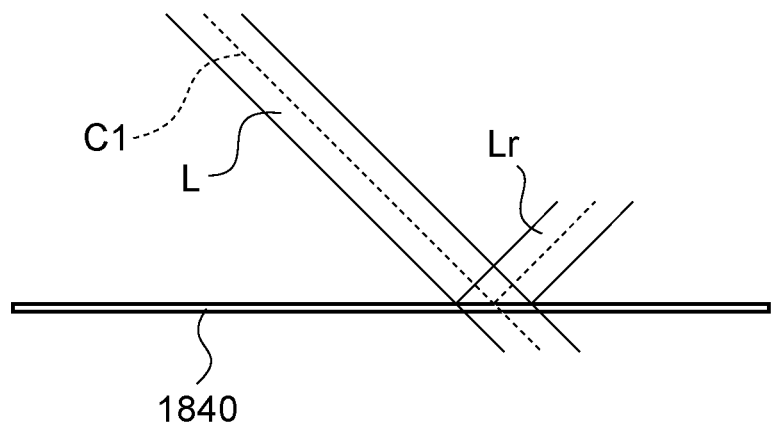
FIG. 73 A schematic diagram of the laser light emitted from the light emitting unit of the blood flow measurement apparatus.
Figure 74:
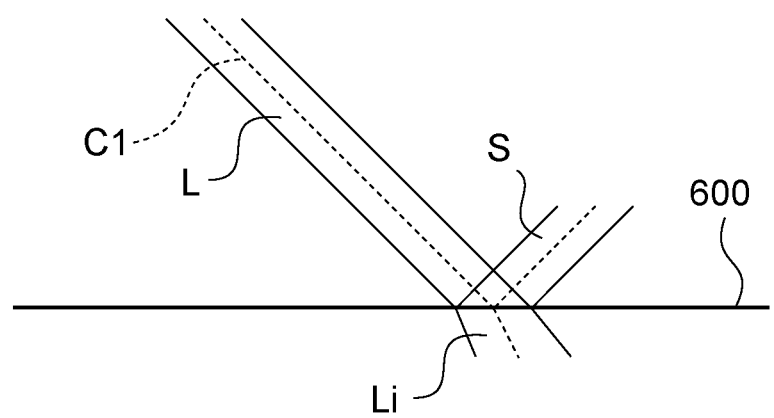
FIG. 74 A schematic diagram of the laser light emitted from the light emitting unit of the blood flow measurement apparatus.
Figure 75:
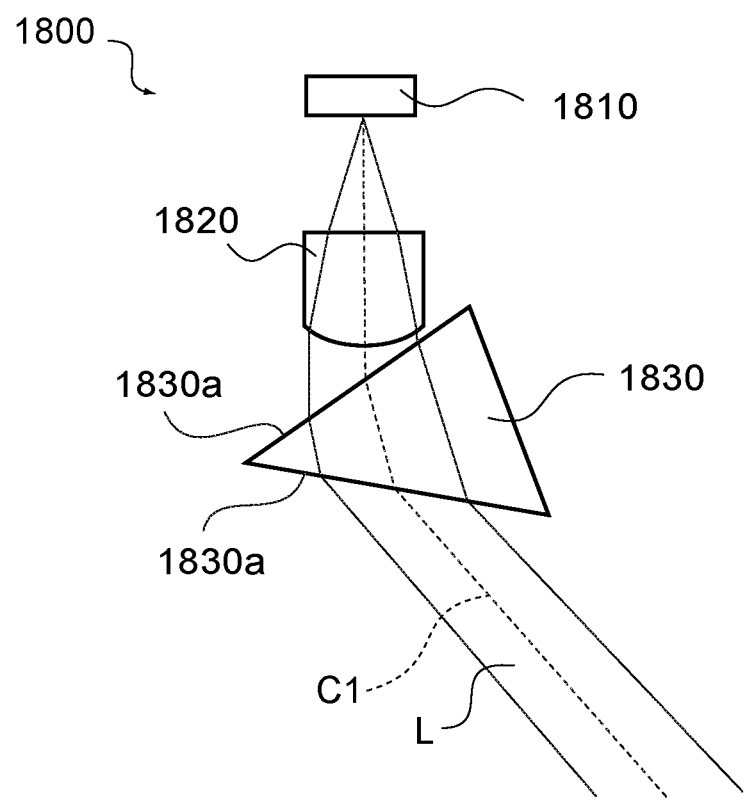
FIG. 75 A schematic diagram of the light emitting unit of the blood flow measurement apparatus.

FIGS. 73 to 75 are schematic diagrams each showing the action of the laser light emitted from the laser light source 1810 having such a configuration.

FIG. 73 shows the laser light L incident on a cover 1840. The cover 1840 is a transparent cover that is attached to the sensor head and covers the light receiving unit and the light emitting unit. As shown in the figure, when the laser light L is incident on the cover 1840, part of the laser light L is reflected by the cover 1840.

The figure shows reflected light Lr reflected by the cover 1840. Since the reflected light Lr is not emitted to the living body, it is favorable that the amount of the reflected light Lr is small.

Here, in a case where the laser light source 1810 has the direction D4 perpendicular to the plane E as the polarization direction as described above, the reflectance is reduced by the cover 1840 and it is possible to reduce the amount of reflected light Lr.

Further, FIG. 74 shows the laser light L incident on the living body 600. The surface (skin) of the living body 600 is rough, but reflected components are more on the front side shown as S. This indicates that the surface (skin) of the living body 600 is rough, but there are many surface components oriented in the normal direction of the surface. Therefore, when the direction D4 perpendicular to the plane E is used as the polarization direction, reflected components are reduced, that is, light (Li in the figure) entering a skin 610 is increased.

In addition, FIG. 75 is a schematic diagram showing an optical path of the laser light L in the light emitting unit 1800 described above. As shown in the same figure, the laser light L is refracted by a refractive surface 1830a of the prism 1830 and travels obliquely.

Here, in a case where the laser light source 1810 sets the direction D4 perpendicular to the plane E as the polarization direction, the reflected light on the refractive surface 1830a decreases and the amount of laser light L reaching the living body can be increased. It should be noted that although the optical system for making the optical axis of laser light L oblique is not limited to that shown in FIG. 75, it is possible to reduce the reflected light at the refracting surface by setting the direction D4 perpendicular to the plane E as the polarization direction as long as the optical path of the laser light L is on the plane E.

(Regarding Incident Direction of Laser Light)

Figure 76:
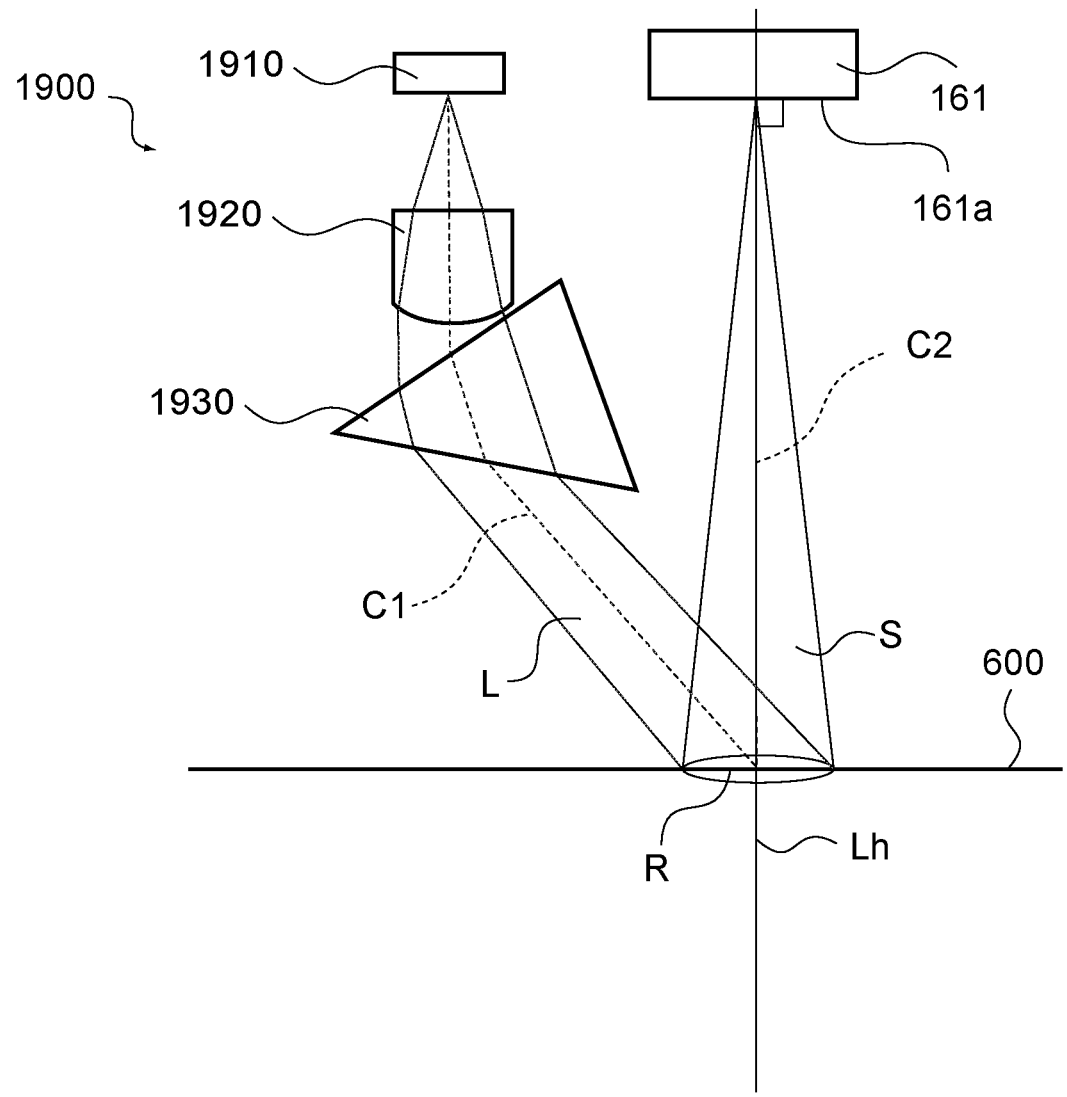
FIG. 76 A schematic diagram of the light emitting unit and the light receiving unit of the blood flow measurement apparatus.

In the light emitting unit of the blood flow measurement apparatus according to each of the above-mentioned embodiments, it is favorable that the incident direction of the laser light is as follows. FIG. 76 is a schematic diagram showing an optical path of the laser light L in a light emitting unit 1900. As shown in the figure, the light emitting unit 1900 includes a laser light source 1910, a lens 1920, and a prism 1930.

The laser light source 1910 can have the same configuration as the laser light source 151 described in the first embodiment. The laser light source 1910 may emit laser light whose polarization direction is a specific direction or may emit laser light whose polarization direction is not defined.

The lens 1920 collimates the incident laser light and makes it incident on the prism 1930. The prism 1930 refracts the incident laser light and tilts its path.

The laser light L emitted from the prism 1930 is incident on the living body 600 to form a spot R. The scattered light S emitted from the spot R is received by the measurement light receiving element 161. It should be noted that in the figure, the incident angle limiting unit (see FIG. 18) is not shown.

As shown in the figure, a straight line perpendicular to the light receiving surface 161a of the measurement light receiving element 161 is defined as a perpendicular line Lh. The light emitting unit 1900 is configured such that the optical axis C1 of the laser light L emitted from the lens 1920 is inclined with respect to the perpendicular line Lh and the optical axis C1 crosses the perpendicular line Lh on the surface of the living body 600.

Thus, it is possible to improve the utilization efficiency of the laser light L by making the laser light L obliquely incident to form the spot R in front of the measurement light receiving element 161 and combining it with the incident angle limiting unit of the light receiving unit.

Figure 77:
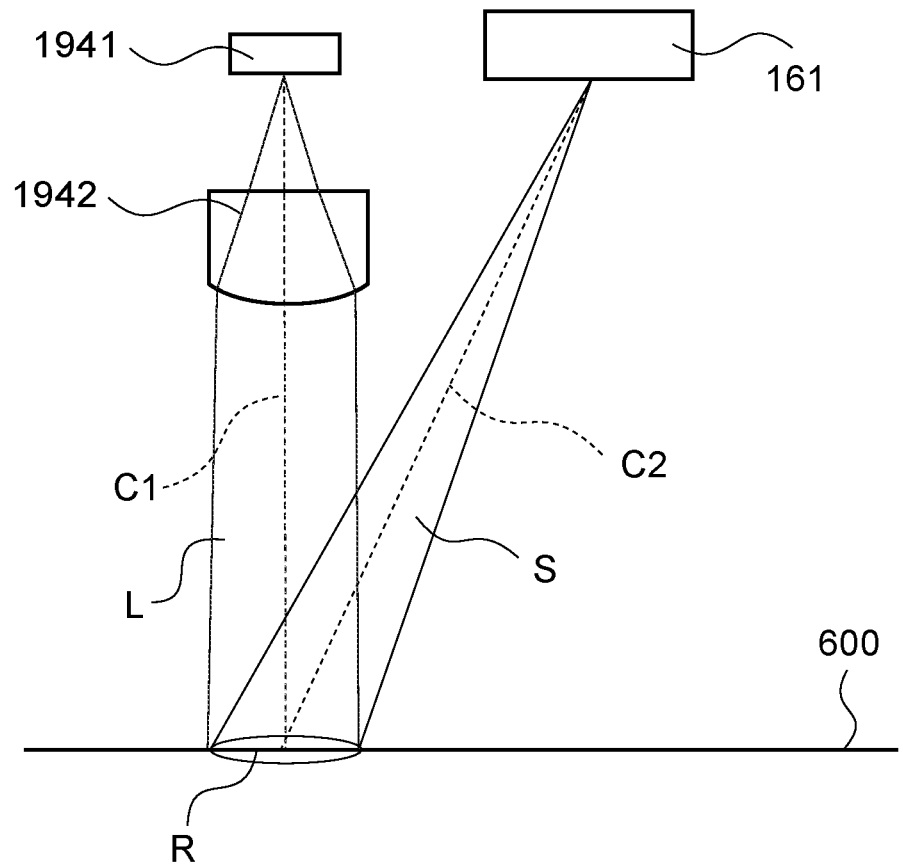
FIG. 77 A schematic diagram of the light emitting unit and the light receiving unit of the blood flow measurement apparatus.

FIG. 77 shows a case where the laser light L is emitted from a laser light source 1941 to the front as a comparative. The laser light L is collimated by a lens 1942 and the irradiation spot R is formed on the surface of the living body 600 in front of the laser light source 1941. The measurement light receiving element 161 obliquely receives the scattered light emitted from the spot R.

With this configuration, the irradiation spot R is formed in front of the laser light source 1941 and the range is spread in the internal scattering, though the spot R is formed away from the measurement light receiving element 161. Light is scattered on the tissue of the living body 600 in all directions. Therefore, the amount of light reaching the measurement light receiving element 161 is reduced in accordance with the distance-square law. Therefore, it is difficult to improve the utilization efficiency of light. In addition, if the light receiving direction is greatly inclined, a problem in that the aberration is deteriorated arises in a case where the incident angle limiting unit is constituted by a lens, it is difficult to accurately limit the incident angle.

In contrast, as shown in FIG. 76, the irradiation spot R is formed in front of the measurement light receiving element 161 by making the laser light L obliquely incident. Accordingly, the distance between the irradiation spot R and the measurement light receiving element 161 is shortened. Further, even when the laser light source 1910 and the living body 600 are spaced away from each other, the laser light L is collimated by the lens 1920. Therefore, the light intensity does not decrease. In addition, the measurement light receiving element 161 is capable of limiting the incident angle of the scattered light S through the incident angle limiting unit in a direction closer to the front of the measurement light receiving element 161. Therefore, the measurement light receiving element 161 is capable of limiting the incident angle without being affected by deterioration of the aberration of the lens.

(Specific Configuration for Making Laser Light Obliquely Incident)

FIGS. 78 to 85 are schematic diagrams each showing a specific configuration of a light emitting unit 1900 for making the laser light L obliquely incident. In each figure, the light emitting unit 1900 is configured such that the laser light L is emitted from the laser light source 1910, is collimated, and obliquely enters the front of the measurement light receiving element 161. It should be noted that in FIGS. 78 to 81, the light receiving unit shows only the measurement light receiving element 161 and does not show the incident angle limiting unit.

Figure 78:
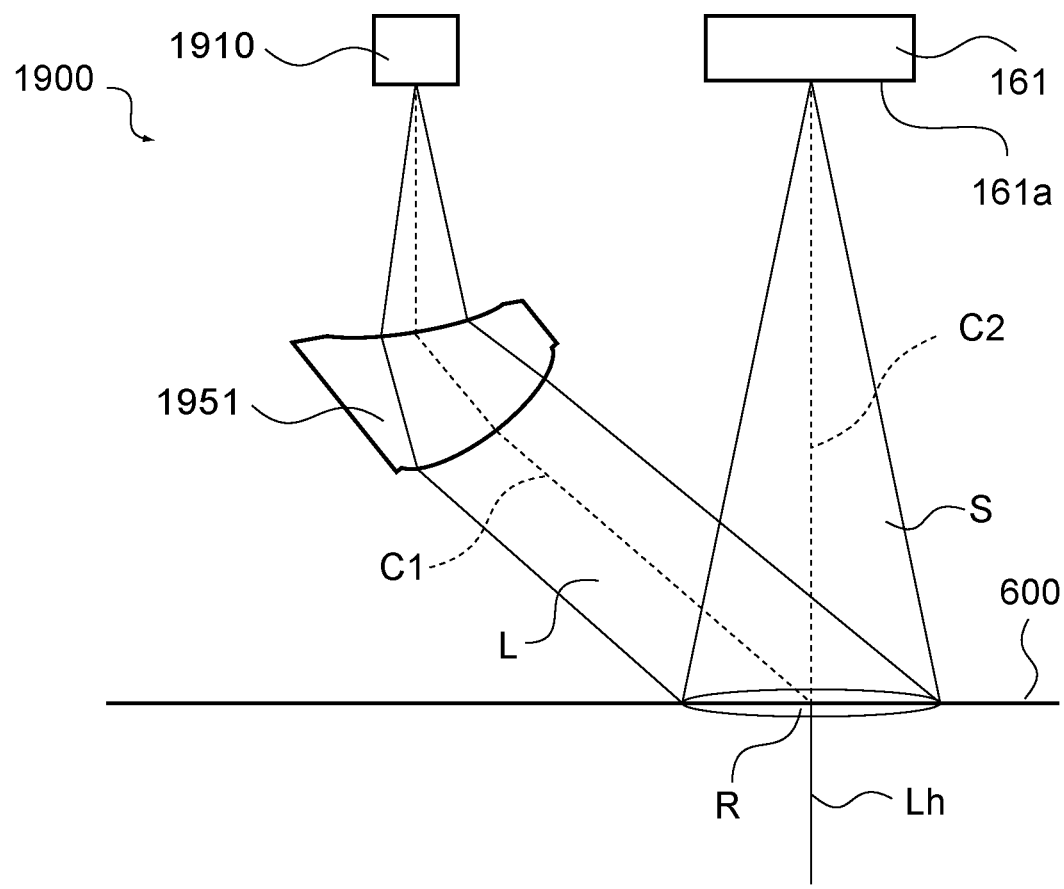
FIG. 78 A schematic diagram of the light emitting unit and the light receiving unit of the blood flow measurement apparatus.

As shown in FIG. 78, the light emitting unit 1900 may include a free-form surface prism 1951. The laser light L emitted from the laser light source 1910 is inclined and collimated by the free-form surface prism 1951.

Figure 79:
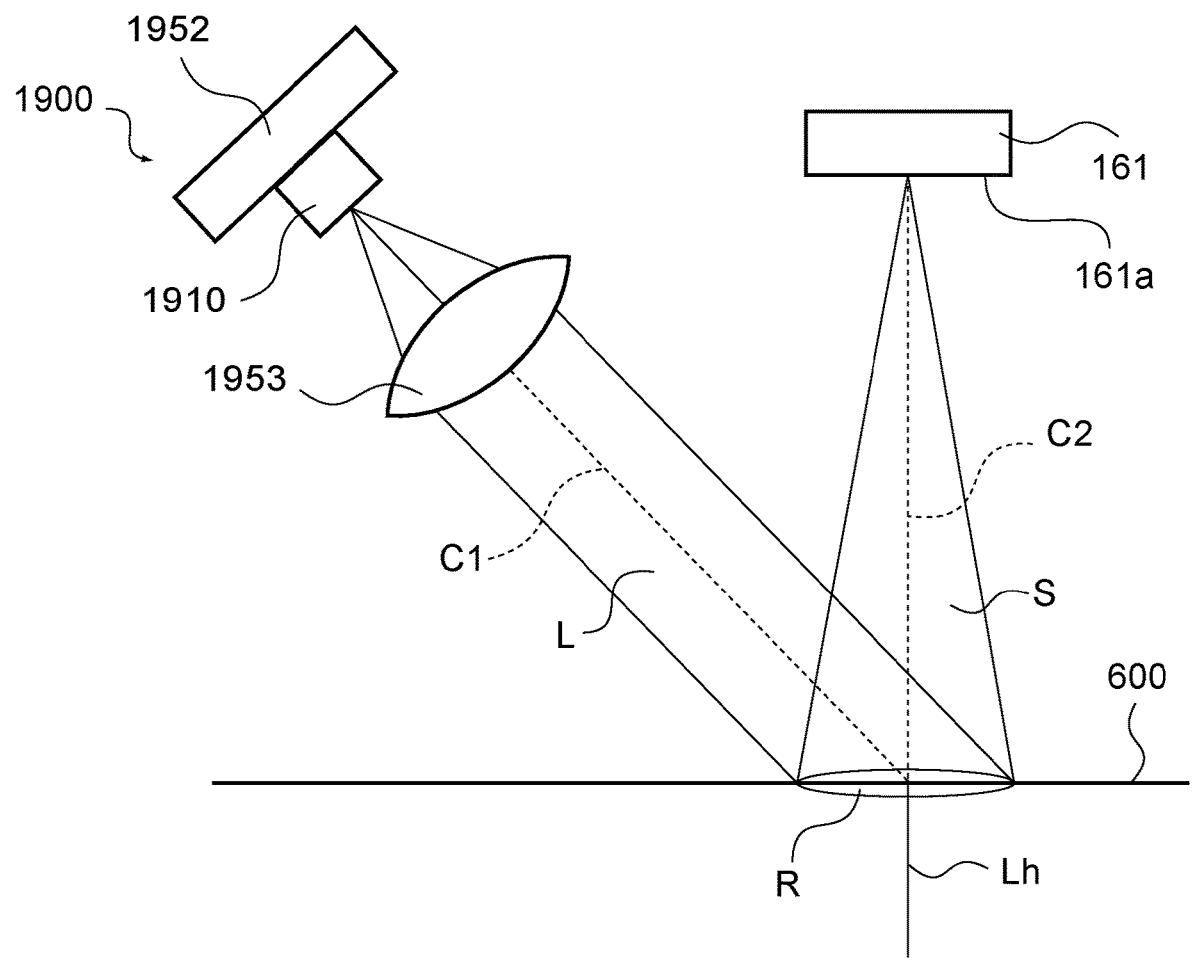
FIG. 79 A schematic diagram of the light emitting unit and the light receiving unit of the blood flow measurement apparatus.

Further, as shown in FIG. 79, the light emitting unit 1900 may include a support member 1952 for tilting the laser light source 1910. The laser light L is emitted from the inclined laser light source 1910 and is collimated by a lens 1953.

Figure 80:
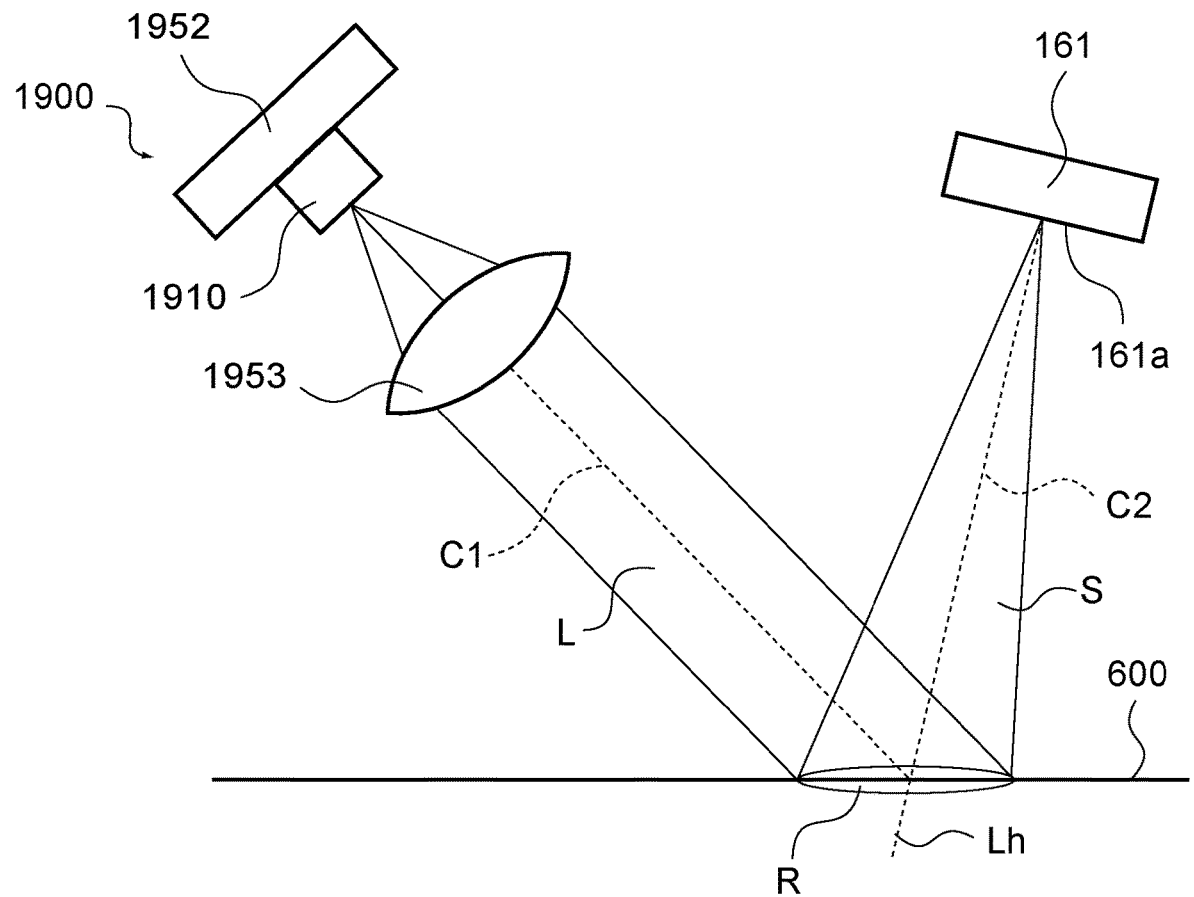
FIG. 80 A schematic diagram of the light emitting unit and the light receiving unit of the blood flow measurement apparatus.

Further, as shown in FIG. 80, the light receiving surface 161a does not need to be parallel to the surface of the living body 600. By arranging the light receiving unit also inclined in this manner, it is possible to reduce an adverse effect caused when light reflected from the light receiving unit enters the living body 600 again.

Figure 89:
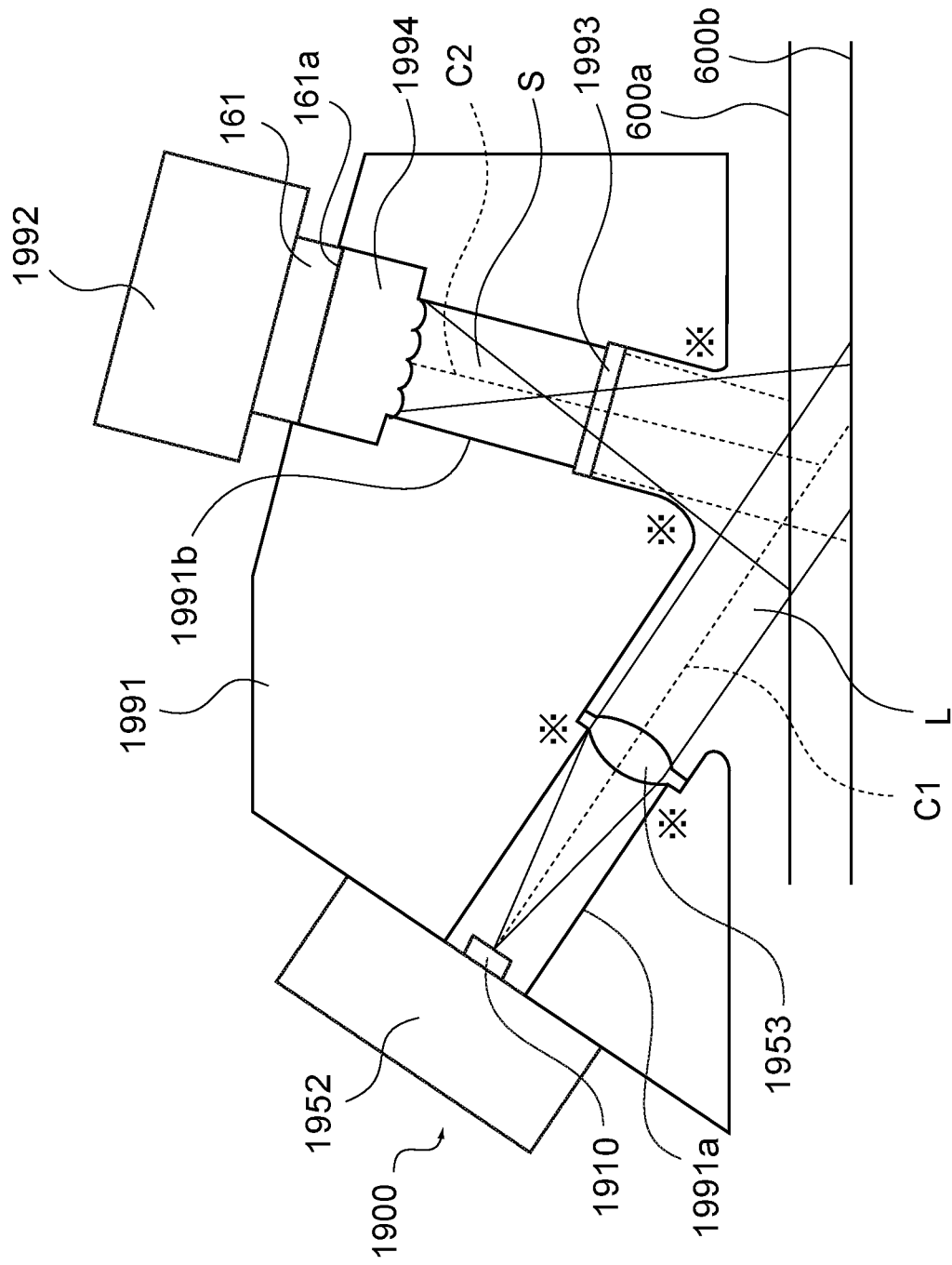
FIG. 89 A schematic diagram of the light emitting unit and the light receiving unit of the blood flow measurement apparatus.

FIG. 89 is a diagram showing a more specific example of the configuration shown in FIG. 80. As shown in the figure, a laser light source 1910 and the measurement light receiving element 161 may be disposed in a light shield 1991 provided with openings 1991a and 1991b through the substrate 1952 and a substrate 1992.

The laser light emitted from the laser light source 1910 travels through the opening 1991a, is collimated by the lens 1953, and enters the living body. The figure shows a living body surface 600a that has approached the sensor head in a relative motion and a living body surface 600b moves away from the sensor head in a relative motion.

The scattered light S emitted from the living body travels through an opening 1991b, passes through a cover 1993, and enters the light receiving unit. A lens array 1994 disposed in front of the measurement light receiving element 161. The incident angle of the light receiving unit is limited by the lens array 1994 and the wall surface of the opening 1991b. Further, if a light shielding mask having the same diameter is provided at a portion indicated by ":X:", an equivalent angle limitation is possible.

With this configuration, the efficiency can be improved by tilting the laser light source 1910. Further, the wall surface of the opening 1991b prevents light beams in the adjacent lenses in the lens array 1994 from mixing with each other. In addition, since the light receiving unit does not include the louvers and the light shield for each lens, the utilization efficiency of light is increased.

Figure 81:
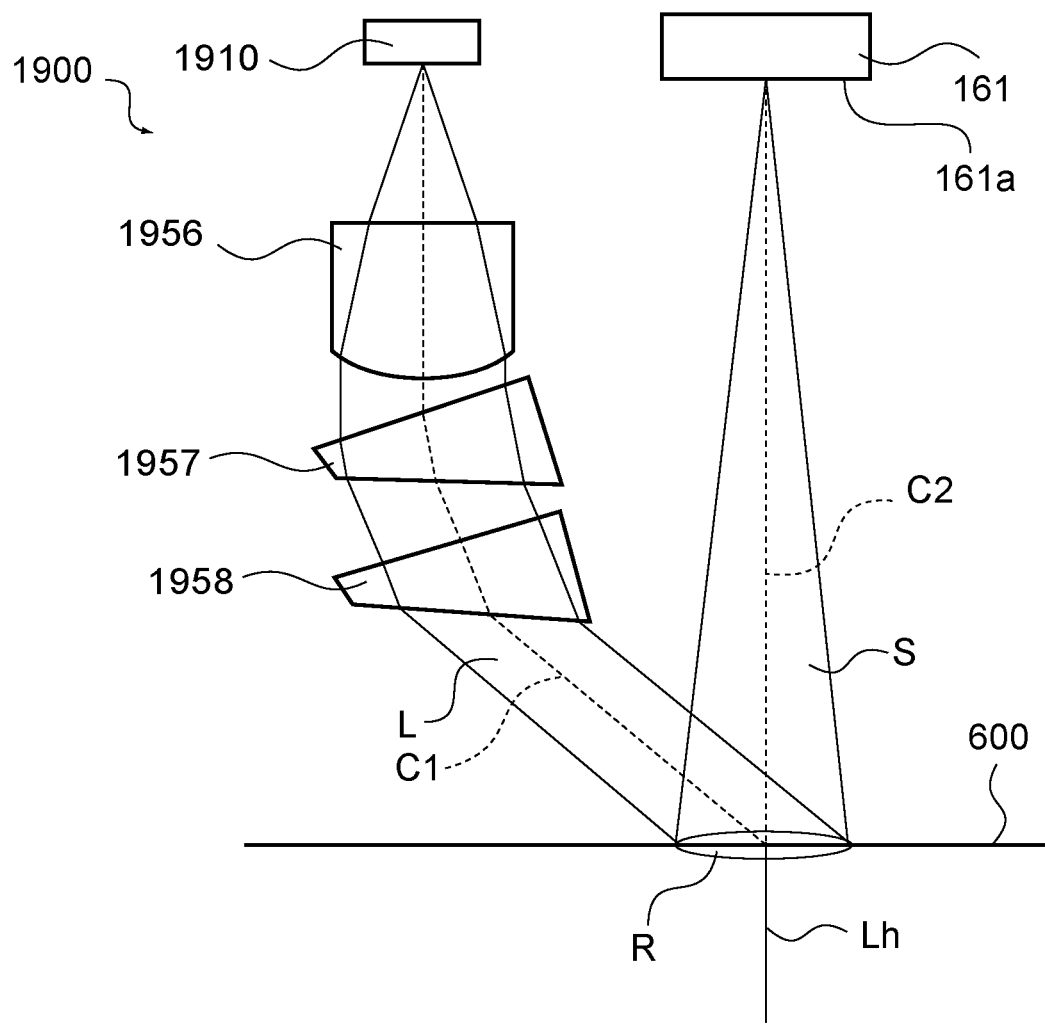
FIG. 81 A schematic diagram of the light emitting unit and the light receiving unit of the blood flow measurement apparatus.
Figure 82:
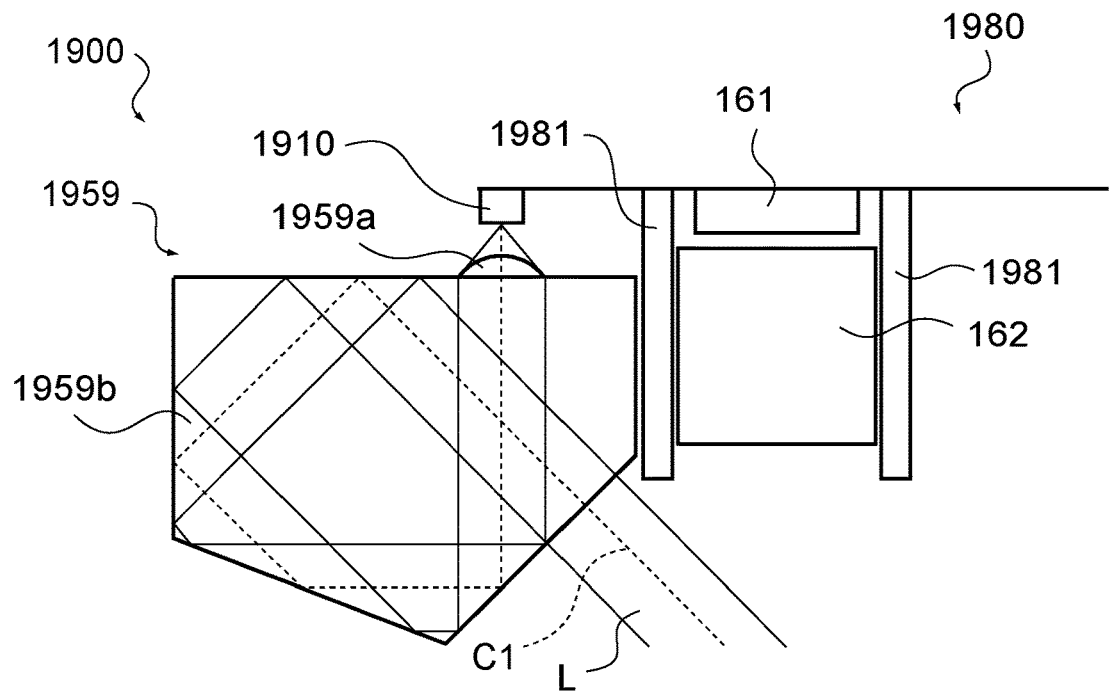
FIG. 82 A schematic diagram of the light emitting unit and the light receiving unit of the blood flow measurement apparatus.

Further, as shown in FIG. 81, the light emitting unit 1900 may include a plurality of divided prisms. The laser light L emitted from the laser light source 1910 is collimated by a lens 1956. The parallelized laser light L is inclined by refraction by a prism 1957 and a prism 1958.

Further, as shown in FIG. 81, the light emitting unit 1900 may include a lens-integrated prism 1959 in which a lens 1959a and a prism 1959b are integrated. The laser light L emitted from the laser light source 1910 is collimated by the lens 1959a. The parallelized laser light L is inclined by refraction by the prism 1959b.

As shown in the figure, the light emitting unit 1900 can be disposed adjacent to the light receiving unit 1980. The light receiving unit 1980 includes the measurement light receiving element 161, the incident angle limiting unit 162, and a light shield 1981. The light shield 1981 prevents light leaking from the lens-integrated prism 1959 from reaching the incident angle limiting unit 162.

Figure 83:
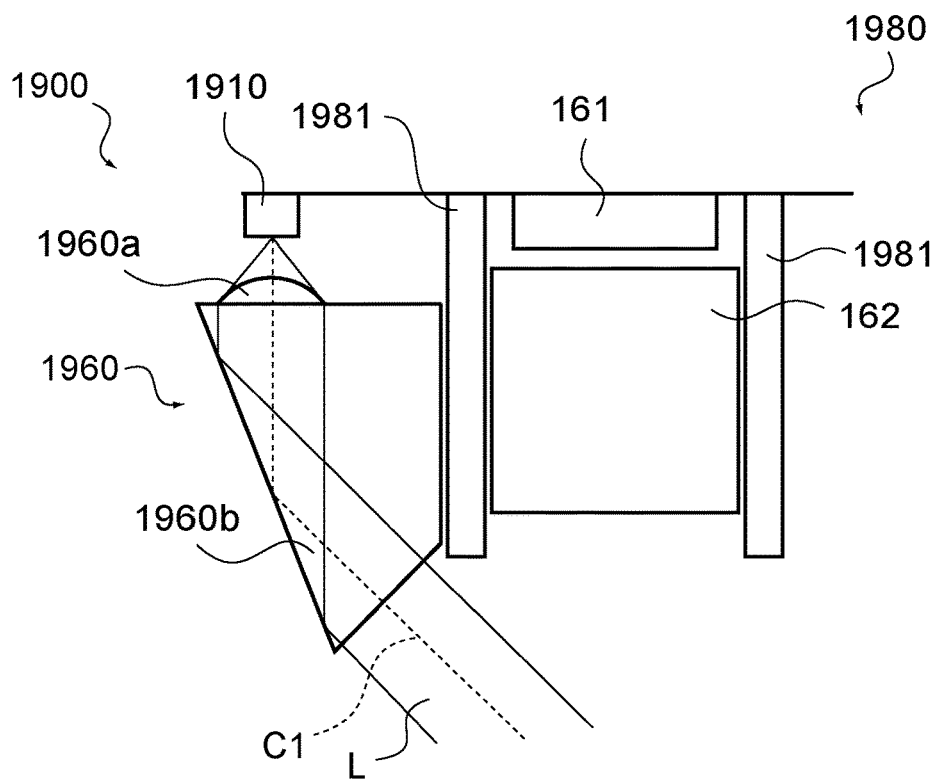
FIG. 83 A schematic diagram of the light emitting unit and the light receiving unit of the blood flow measurement apparatus.

Further, as shown in FIG. 83, the light emitting unit 1900 may include a lens-integrated prism 1960 in which a lens 1960a and a prism 1960b are integrated. The laser light L emitted from the laser light source 1910 is collimated by the lens 1960a. The parallelized laser light L is inclined by refraction by the prism 1960b.

Figure 84:
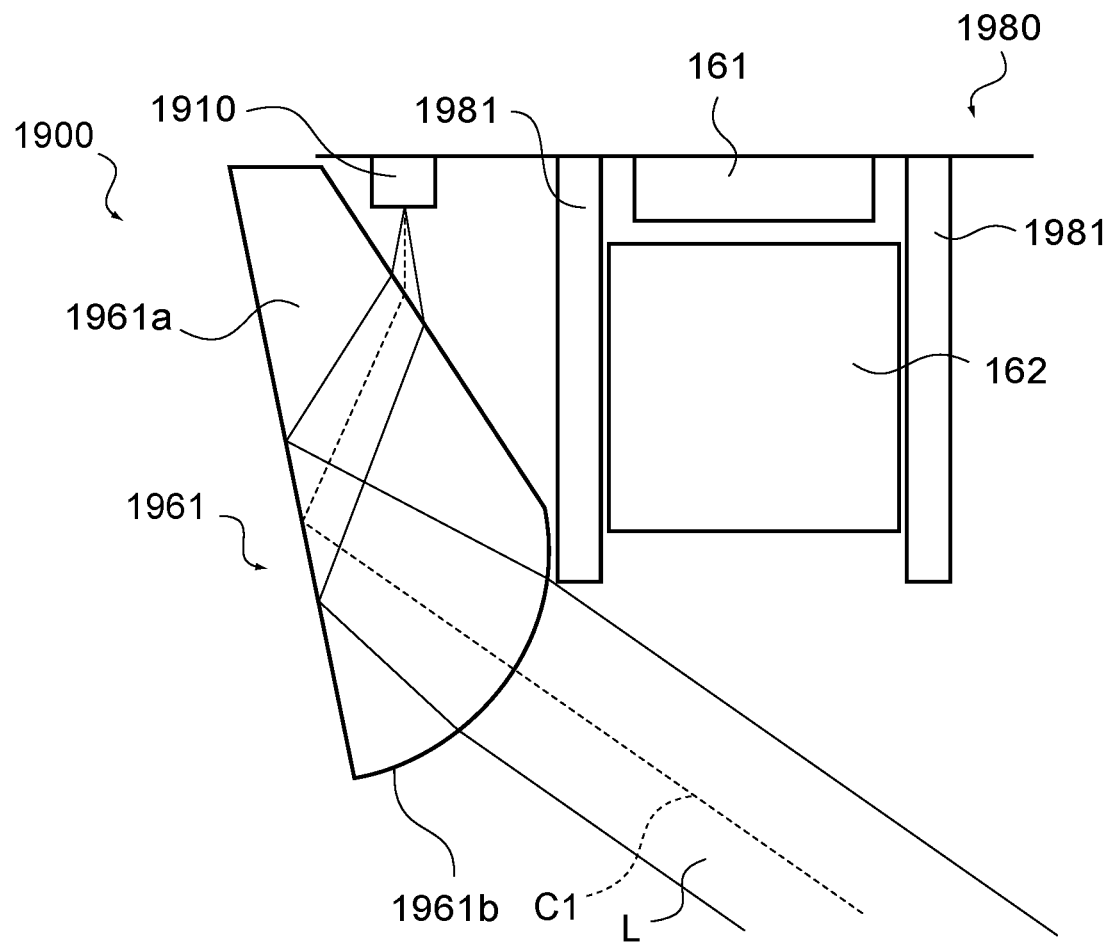
FIG. 84 A schematic diagram of the light emitting unit and the light receiving unit of the blood flow measurement apparatus.

Further, as shown in FIG. 84, the light emitting unit 1900 may include a lens-integrated prism 1961 in which a prism 1961a and a lens 1961b are integrated. The laser light L emitted from the laser light source 1910 is inclined by the prism 1961a and is collimated by the lens 1961b. With this configuration, the amount of reflection when the coherent light is incident on the prism 1961 can be reduced by setting the incident angle on the lens-integrated prism 1961 around the Brewster's angle corresponding to the refractive index of the optical member of the prism 1961.

Further, with any of the above-mentioned configurations, the reflection on the surface of the living body 600 can be reduced by setting the emission angle of light to the living body 600 around the Brewster's angle corresponding to the refractive index of the living body 600. The details thereof will be described later.

As described above, in the light emitting unit 1900, the laser light L can be tilted by various configurations. Further, the light emitting unit 1900 may have a configuration other than that described above as long as it can collimate and tilt the laser light L.

Figure 85:
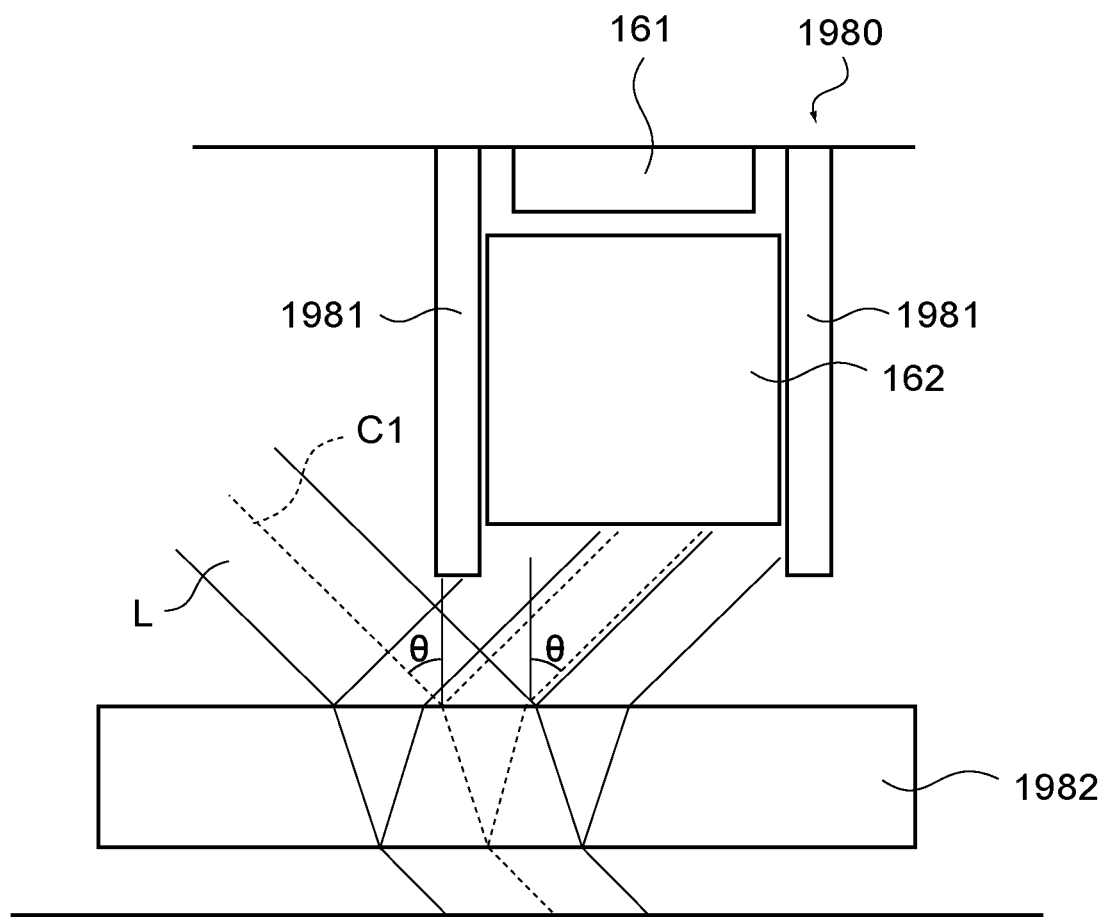
FIG. 85 A schematic diagram of the light receiving unit of the blood flow measurement apparatus.

In addition, in the light emitting unit of the blood flow measurement apparatus according to each of the above-mentioned embodiments, the light receiving unit is favorably configured as follows in a case where the incident direction of laser light is inclined. FIG. 85 is a schematic diagram showing the light receiving unit 1980 and a cover 1982.

As shown in the figure, in a case where the laser light L is reflected in the cover 1982 at an angle θ, the incident angle limiting unit 162 can be configured to shield the incident light at the incident angle θ or more. Accordingly, it is possible to prevent the reflected light by the cover 1982 from reaching the measurement light receiving element 161. It should be noted that in the configuration shown in FIG. 80, the light receiving unit and the living body 600 do not face each other. Therefore, the cover 1982 may be disposed so as not to cover the optical path of the light source light. It is possible to prevent the light at the angle θ from entering the incident angle limiting unit.

(Regarding Advantage in Oblique Incidence of Laser Light)

When the laser light is made incident obliquely as described above and the polarization direction of the laser light L is made perpendicular to the plane E (see FIG. 72), the following advantage occurs.

Figure 86:
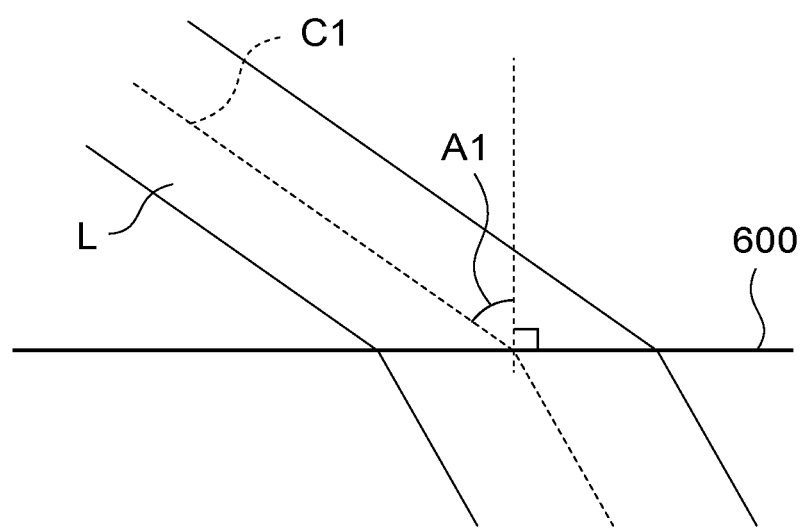
FIG. 86 A schematic diagram of the laser light emitted from the light emitting unit of the blood flow measurement apparatus.

FIG. 86 is a schematic diagram showing the laser light L obliquely incident on the living body 600. It is favorable to set an incident angle A1 in FIG. 86 to be the Brewster's angle corresponding to the refractive index of the surface of the living body 600 (incident angle at which the reflectance of incident light of p-polarized light becomes 0 at the interface between flat surfaces of transparent materials). In a case where the living body 600 is human skin, the refractive index of the skin stratum corneum is known to be approximately 1.5, with a corresponding Brewster's angle of 56.3°. That is, it is favorable to set the incident angle of the laser light L such that A1 takes an angle in the vicinity of 56.3°.

By aligning the polarization directions and utilizing the Brewster's angle, it is possible to minimize the loss of light reflected on the stratum corneum and to maximize the amount of light reaching the target to be observed. It should be noted that at an angle shallower than Brewster's angle (more parallel to the plane), the reflectivity increases rapidly as it becomes further from the Brewster's angle. Therefore, it is favorable to make the light incident at an angle slightly deeper than the Brewster's angle (more perpendicular to the plane) because the resistance to the fabrication tolerance and the like is increased.

Figure 87:
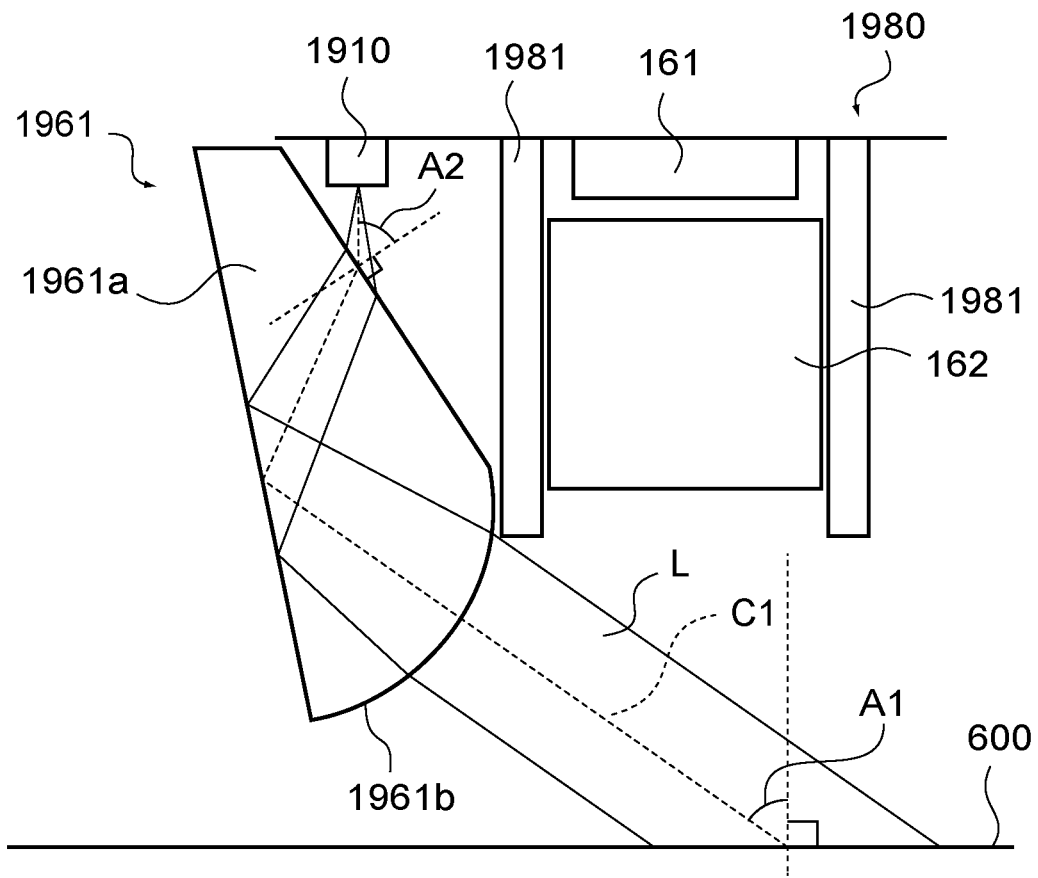
FIG. 87 A schematic diagram of the light emitting unit and the light receiving unit of the blood flow measurement apparatus.

FIG. 87 is an example of a configuration of a light emitting unit 1900 for making light incident on the living body 600 at the Brewster's angle. As shown in the figure, laser light L at a Brewster's angle A2 corresponding to the refractive index of the lens-integrated prism 1961 is configured to be incident on the lens-integrated prism 1961. Accordingly, the laser light L can be made to enter at a Brewster's angle A1.

(Regarding Spot Shape of Laser Light)

When the laser light is made incident on the living body 600 in the light emitting unit of the blood flow measurement apparatus according to each of the above-mentioned embodiments, it is favorable that the irradiation spot R is circular on the surface of the living body 600 as viewed from the measurement light receiving element in terms of the utilization efficiency of light. Therefore, in a case of making the laser light L obliquely incident on the living body 600 as described above, the spot R on the surface of the living body 600 can be made to have a shape close to a circular shape by making the beam shape of the laser light L elliptical.

Figure 88:
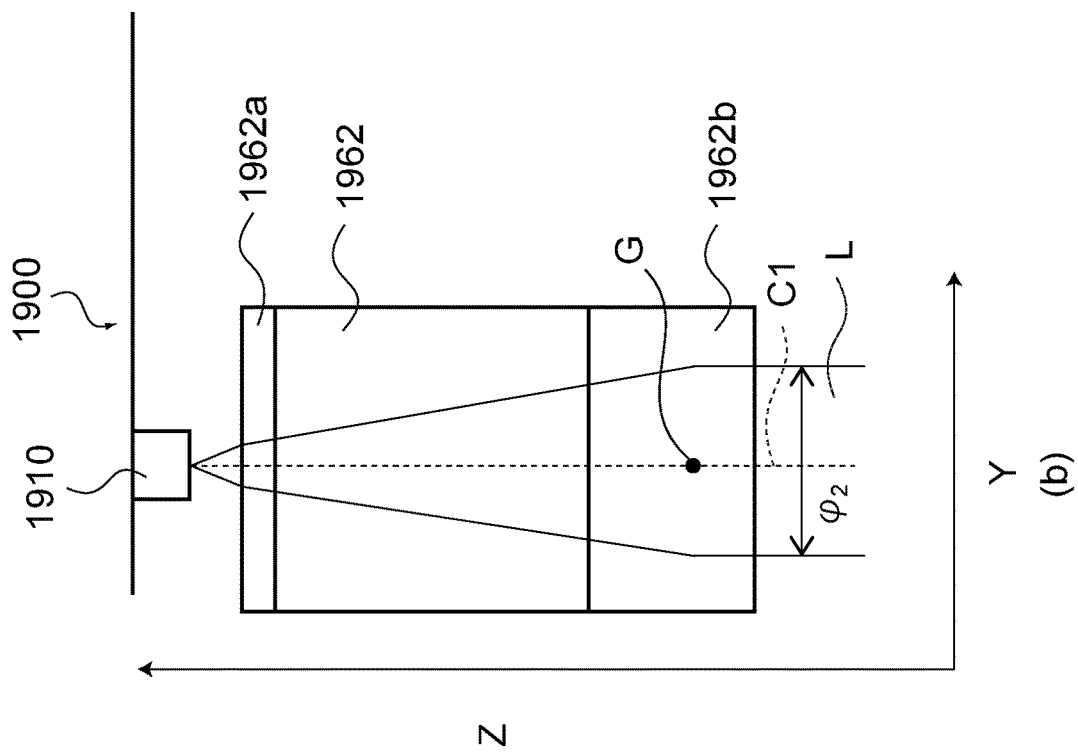
FIG. 88 A schematic diagram of the light emitting unit of the blood flow measurement apparatus.
Figure 88:
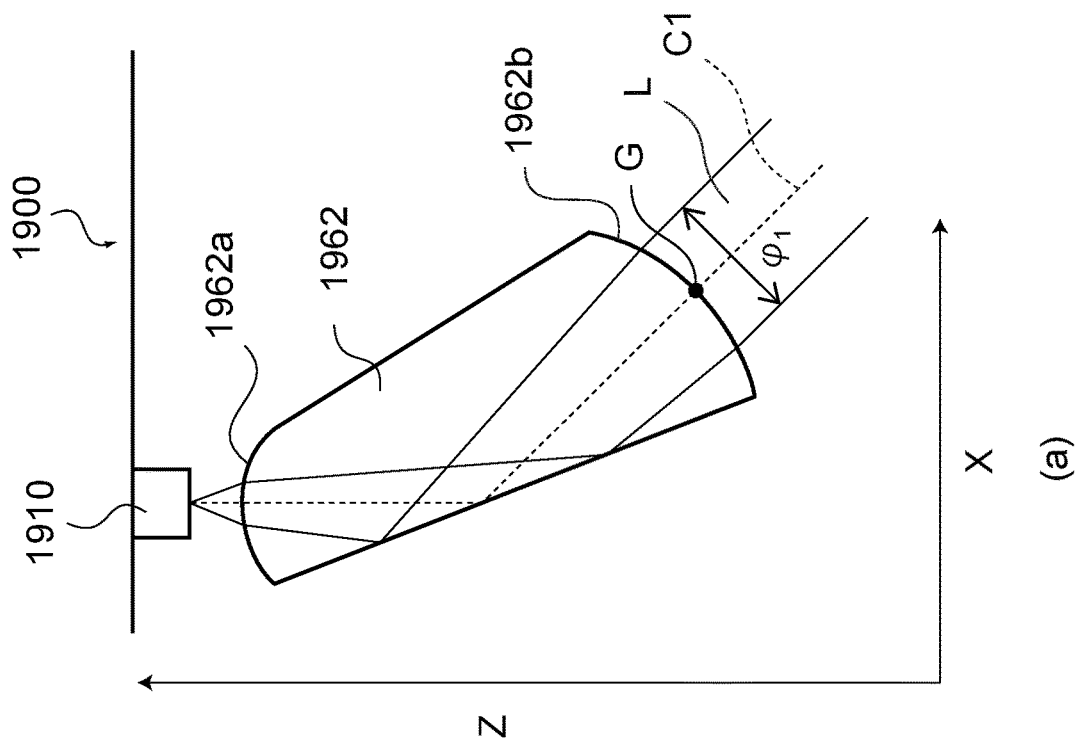

FIG. 88 is a schematic diagram showing a configuration of a light emitting unit 1900 for making the spot R circular on the surface of the living body 600. FIG. 88(*a*) is a diagram viewed in the Y direction. FIG. 88(*b*) is a diagram viewed in the X direction. It should be noted that X-Z plane coincides with the plane E (see FIG. 72).

As shown in the figure, the light emitting unit 1900 includes a prism 1962. The prism 1962 has a cylindrical lens 1962*a* and an aspherical lens 1962*b*. Further, the starting point on the optical axis of the laser light L emitted from the prism 1962 as a point G.

As shown in FIG. 88(*a*), as viewed in the Y direction, only by the amount of reduction in the emission angle of the laser light L in the cylindrical lens 1962*a*, a beam diameter $\phi_1$ of the laser light L in the aspherical lens 1962*b* is reduced.

Further, as shown in FIG. 88(*b*), as viewed in the X direction, the beam diameter $\phi_2$ of the laser light L increases with respect to the X direction because the cylindrical lens 1962*a* has no lens effects. Accordingly, it is possible to shape the laser light L into a large elliptical beam shape having a smaller diameter in the X direction at the point G and a larger diameter in the Y direction and form a circular irradiation spot shape in front of the measurement light receiving element.

(Application Examples of Present Technology)

In each of the above-mentioned embodiments, in the present embodiment, the blood flow measurement apparatus for detecting a motion of a red blood cell flowing in blood flow has been described. In addition to the blood flow, the present technology can be used for measurement of moving particles as long as those causes the laser Doppler effect. Accordingly, it is possible to realize a scattered light signal measurement apparatus capable of eliminating noise caused by the relative motion between the sensor and the measurement target.

In this case, the blood flow-related information calculation unit described in each of the above-mentioned embodiments functions as a particle velocity information calculation unit that calculates particle velocity information which is information regarding a particle velocity. The noise cancellation unit is capable of cancelling noise caused by the relative motion between the sensor and the measurement target on the basis of the particle velocity information.

It should be noted that the present technology may also take the following configurations.

(1) A scattered light signal measurement apparatus, including:

a light receiving element that receives scattered light obtained when coherent light emitted to a measurement target is scattered by the measurement target; and an incident angle limiting unit that limits an incident angle of the scattered light that is incident on a single point of the light receiving element to be equal to or smaller than a predetermined angle and controls the single light receiving element to increase an aperture ratio.

(2) The scattered light signal measurement apparatus according to (1), in which the incident angle limiting unit limits a light beam diameter of the scattered light that is incident on the single point of the light receiving element to be smaller than an entire light beam diameter that is incident on the light receiving element.

(3) The scattered light signal measurement apparatus according to (2), in which the incident angle limiting unit concentrates the scattered light at a different point of the light receiving element in accordance with an incident angle.

(4) The scattered light signal measurement apparatus according to (3), in which the incident angle limiting unit is a lens array in which a plurality of lenses is arranged.

(5) The scattered light signal measurement apparatus according to (4), in which the light receiving element is at least one, and the plurality of lenses concentrates scattered light at an incident angle limited by each of a plurality of lenses to the single light receiving element.

(6) The scattered light signal measurement apparatus according to (3) or (4), in which the incident angle limiting unit is a lens, further including a light shield that prevents mixing of light incident on the lens and light incident on a portion other than the lens.

(7) The scattered light signal measurement apparatus according to (2), in which the light receiving element is at least one, and the incident angle limiting unit that sets a plurality of pin holes with respect to the single light receiving element, limits the incident angle of the scattered light that is incident on the single point of the light receiving element to be equal to or smaller than the predetermined angle, and concentrates scattered light having an amount larger than an amount of scattered light, which is concentrated by a single pin hole, to the light receiving element.

(8) The scattered light signal measurement apparatus according to any one of (1) to (9), further including:
a coherent light source that emits the coherent light; and
an irradiation light control unit that controls an irradiation diameter of the coherent light emitted from the coherent light source.

(9) The scattered light signal measurement apparatus according to (8), in which
the irradiation light control unit makes the coherent light collimated, the coherent light being emitted from the light source.

(10) The scattered light signal measurement apparatus according to (9), in which
the irradiation diameter is 0.5 mm or more and 2 mm or less.

(11) The scattered light signal measurement apparatus according to any one of (1) to (10), further including:
a first coherent light source that emits first coherent light having a first wavelength range to the measurement target; and
a second coherent light source that emits second coherent light having a second wavelength range different from the first wavelength range to the measurement target.

(12) The scattered light signal measurement apparatus according to any one of (1) to (10), further including:
a coherent light source that emits the coherent light to the measurement target;
a reflector that reflects part of the coherent light emitted from the coherent light source; and
a light receiving element that receives the coherent light reflected by the reflector.

(13) The scattered light signal measurement apparatus according to any one of (1) to (10), further including
a light receiving element array in which a plurality of light receiving elements is arranged.

(14) The scattered light signal measurement apparatus according to any one of (1) to (13), in which
the incident angle limiting unit includes one louver layer or a plurality of louver layers,
the louver layer includes a plurality of louvers extending in parallel to each other, and
in a case of including the plurality of louver layers, the incident angle limiting unit is an optical path limiting filter in which directions in which the respective louvers of the layers extend cross each other.

(15) The scattered light signal measurement apparatus according to (14), in which
the incident angle limiting unit is a lens array in which a plurality of lenses is arranged, and
the louver has a height that enables mixing of light passing through the filter between adjacent lenses of the plurality of lenses to be prevented.

(16) The scattered light signal measurement apparatus according to any one of (1) to (15), further including
a polarization filter disposed in any optical path between the measurement target and the light receiving element.

(17) The scattered light signal measurement apparatus according to (16), in which
the polarization filter permits light having a polarization direction in a direction perpendicular to a plane formed by an optical axis of the coherent light and an optical axis of the scattered light to pass therethrough.

(18) The scattered light signal measurement apparatus according to any one of (1) to (17), in which
the coherent light source and the irradiation light control unit make the coherent light incident on the measurement target in a direction inclined with respect to an optical path of scattered light travelling toward the light receiving surface from the measurement target.

(19) The scattered light signal measurement apparatus according to (18), in which
the irradiation light control unit shapes the coherent light into an elliptical shape and emits the shaped coherent light such that an irradiation spot of the coherent light at the measurement target has a circular shape.

(20) The scattered light signal measurement apparatus according to any one of (1) to (19), in which
the coherent light source emits coherent light having a polarization direction in a direction perpendicular to a plane formed by an optical axis of the coherent light and an optical axis of the scattered light.

(21) The scattered light signal measurement apparatus according to any one of (1) to (19), in which
the coherent light source emits coherent light having a polarization direction in a direction parallel to a plane formed by an optical axis of the coherent light and an optical axis of the scattered light.

(22) An information processing apparatus, including:
a light receiving element that receives scattered light obtained when coherent light emitted to a measurement target is scattered by the measurement target;
an incident angle limiting unit that limits an incident angle of the scattered light that is incident on a single point of the light receiving element to be equal to or smaller than a predetermined angle and controls the single light receiving element to increase an aperture ratio; and
a particle velocity information calculation unit that calculates particle velocity information that is information regarding velocity of a particle inside the measurement target on the basis of a signal output from the light receiving element.

(23) The information processing apparatus according to (22), further including
a noise cancellation unit that cancels noise caused by a relative motion between the sensor and the measurement target from the particle velocity information on the basis of two signals respectively generated from two types of light different in optical characteristic.

(24) The information processing apparatus according to (23), in which
the noise cancellation unit cancels the noise on the basis of a first signal generated by first coherent light being scattered by the measurement target and received by the light receiving element and a second signal generated by second coherent light different in wavelength range from the first coherent light being scattered by the measurement target and received by the light receiving element.

(25) The information processing apparatus according to (23), in which
the noise cancellation unit cancels the noise on the basis of a first signal generated by the coherent light being scattered by the measurement target and received by the light receiving element and a second signal generated by light being received by the light receiving element, the light including scattered light obtained when the coherent light is scattered by the measurement target and the coherent light.

(26) The information processing apparatus according to (22), further including
a noise cancellation unit that detects a relative motion between the sensor and the measurement target on the basis of an output of a light receiving element array in which a plurality of light receiving elements provided in the sensor is arranged, and cancels noise caused by the relative motion between the sensor and the measurement target on the basis of the particle velocity information.

(27) The information processing apparatus according to any one of (22) to (26), in which
the measurement target is blood, and
the particle velocity information calculation unit calculates blood flow velocity information that is information regarding velocity of a red blood cell inside the measurement target.

(28) The information processing apparatus according to any one of (22) to (27), in which
the information processing apparatus includes a wearable device.

REFERENCE SIGNS LIST 100, 200, 300, 400 blood flow measurement apparatus
110, 210, 310, 410 sensor head
111, 211, 311, 411, 1800, 1900 light emitting unit
112112, 312, 313, 412, 1100, 1200, 1300, 1400, 1500, 1600, 1700 light receiving unit
151, 251, 252, 351, 451, 1810, 1910 laser light source
161, 261, 361, 461, 1210, 1310, 1410, 1510, 1610, 1710 measurement light receiving element
162, 165, 168, 171, 262, 362, 364, 462 incident angle limiting unit
163, 164 light shield
352 reflector
363 reflected light receiving element
463 light receiving element array
1120, 1230 louver filter
1320 louver align lens array
1630, 1730 polarization filter

The invention claimed is:

1. A scattered light signal measurement apparatus, comprising:
a coherent light source configured to emit coherent light to a measurement target containing scatterers;
an irradiation light control unit including a plurality of lenses configured to magnify and collimate the coherent light emitted from the coherent light source;
a light receiving element including at least one photodiode configured to receive scattered light obtained when the coherent light emitted to the measurement target is scattered by the scatterers contained in the measurement target; and
an incident angle limiting unit including at least one lens and a plurality of light shields,
wherein the incident angle limiting unit is configured to limit an incident angle of the scattered light that is incident on a single point of the light receiving element to be equal to or smaller than a predetermined angle, and
control the light receiving element to increase an aperture ratio,
wherein each light shield of the plurality of light shields includes a plate-like member made of a material configured to prevent transmission of light having a wavelength of the scattered light, each plate-like member having a surface that extends in parallel to other light shields in a corresponding layer of the plurality of light shields,
wherein a first layer of the plurality of light shields includes a plurality of plate-like members extending in a first direction,
wherein a second layer of the plurality of light shields includes a plurality of plate-like members extending in a second direction different from the first direction, and
wherein the coherent light source includes a laser configured to emit the coherent light.

2. The scattered light signal measurement apparatus according to claim 1,
wherein the incident angle limiting unit is further configured to limit a light beam diameter of the scattered light that is incident on the single point of the light receiving element to be smaller than an entire light beam diameter that is incident on the light receiving element.

3. The scattered light signal measurement apparatus according to claim 2,
wherein the incident angle limiting unit is further configured to concentrate the scattered light at a different point of the light receiving element in accordance with the incident angle.

4. The scattered light signal measurement apparatus according to claim 3,
wherein the incident angle limiting unit includes a lens array in which a plurality of lenses is arranged.

5. The scattered light signal measurement apparatus according to claim 4,
wherein the plurality of lenses concentrates scattered light at the incident angle limited by each of the plurality of lenses to the light receiving element.

6. The scattered light signal measurement apparatus according to claim 3,
wherein the plurality of light shields are configured to prevent mixing of light incident on the at least one lens and light incident on each portion of the incident angle limiting unit other than the at least one lens, and
wherein the plurality of light shields are disposed between the at least one lens of the incident angle limiting unit and the at least one photodiode of the light receiving element.

7. The scattered light signal measurement apparatus according to claim 2,
wherein the incident angle limiting unit is further configured to
set a plurality of pin holes with respect to the light receiving element,
limit the incident angle of the scattered light that is incident from each pin hole on the single point of the light receiving element to be equal to or smaller than the predetermined angle, and
concentrate scattered light having an amount larger than an amount of scattered light, which is concentrated by a single pin hole, to the light receiving element.

8. The scattered light signal measurement apparatus according to claim 1,
wherein the irradiation light control unit includes an optical member including glass configured to control an irradiation diameter of the coherent light emitted from the coherent light source.

9. The scattered light signal measurement apparatus according to claim 8,
wherein the irradiation diameter is 0.5 mm or more and 2 mm or less.

10. The scattered light signal measurement apparatus according to claim 1, further comprising:
a first coherent light source including at least one first laser configured to emit first coherent light having a first wavelength range to the measurement target; and a second coherent light source including at least one second laser configured to emit second coherent light having a second wavelength range different from the first wavelength range to the measurement target.

11. The scattered light signal measurement apparatus according to claim 1, further comprising:
a light receiving element array in which a plurality of photodiodes is arranged.

12. The scattered light signal measurement apparatus according to claim 1,
wherein the incident angle limiting unit includes a single louver layer, and
wherein the single louver layer includes a plurality of louvers extending in parallel to each other.

13. The scattered light signal measurement apparatus according to claim 1, further comprising:
at least one polarization filter disposed in at least one optical path between the measurement target and the light receiving element.

14. The scattered light signal measurement apparatus according to claim 8,
wherein the coherent light source and the irradiation light control unit are further configured to make the coherent light incident on the measurement target in a direction inclined with respect to an optical path of scattered light travelling toward a surface of the light receiving element from the measurement target.

15. The scattered light signal measurement apparatus according to claim 14,
wherein the irradiation light control unit is further configured to
shape the coherent light into an elliptical shape, and
emit the shaped coherent light such that an irradiation spot of the coherent light at the measurement target has a circular shape.

16. The scattered light signal measurement apparatus according to claim 1,
wherein the incident angle limiting unit includes a plurality of louver layers,
wherein each louver layer includes a plurality of louvers extending in parallel to each other, and
wherein the incident angle limiting unit is an optical path limiting filter in which directions in which respective louvers of each louver layer of the plurality of louver layers extend across each other.

17. The scattered light signal measurement apparatus according to claim 1,
wherein the laser is a vertical cavity surface emitting laser.

* * * * *